US011279930B2

(12) United States Patent
Khvorova et al.

(10) Patent No.: US 11,279,930 B2
(45) Date of Patent: Mar. 22, 2022

(54) O-METHYL RICH FULLY STABILIZED OLIGONUCLEOTIDES

(71) Applicant: UNIVERSITY OF MASSACHUSETTS, Boston, MA (US)

(72) Inventors: Anastasia Khvorova, Westborough, MA (US); Julia Alterman, Worcester, MA (US); Sarah Davis, Boston, MA (US); Anton Turanov, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 16/550,076

(22) Filed: Aug. 23, 2019

(65) Prior Publication Data

US 2020/0087663 A1 Mar. 19, 2020

Related U.S. Application Data

(60) Provisional application No. 62/721,993, filed on Aug. 23, 2018.

(51) Int. Cl.
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/321* (2013.01); *C12N 2310/322* (2013.01); *C12N 2310/52* (2013.01)

(58) Field of Classification Search
None
See application file for complete search history.

(56) References Cited

U.S. PATENT DOCUMENTS

| 5,858,988 | A | 1/1999 | Wang |
|---|---|---|---|
| 6,291,438 | B1 | 9/2001 | Wang |
| 6,312,900 | B1 | 11/2001 | Dean et al. |
| 7,750,144 | B2 | 7/2010 | Zamore et al. |
| 7,834,171 | B2 | 11/2010 | Leake et al. |
| 8,304,530 | B2 | 11/2012 | Zamore et al. |
| 8,309,704 | B2 | 11/2012 | Zamore et al. |
| 8,309,705 | B2 | 11/2012 | Zamore et al. |
| 8,329,892 | B2 | 12/2012 | Zamore et al. |
| 8,877,439 | B2* | 11/2014 | Butora ................ C12N 15/113 435/6.1 |
| 9,809,817 | B2 | 11/2017 | Khvorova et al. |
| 9,862,350 | B2 | 1/2018 | Guerrero et al. |
| 10,435,688 | B2 | 10/2019 | Khvorova et al. |
| 10,478,503 | B2 | 11/2019 | Khvorova et al. |
| 10,519,451 | B2 | 12/2019 | Khvorova et al. |
| 2003/0143732 | A1 | 7/2003 | Fosnaugh et al. |
| 2008/0119427 | A1 | 5/2008 | Bhat et al. |
| 2011/0263680 | A1* | 10/2011 | Khvorova ............... A61P 21/00 514/44 A |
| 2013/0178513 | A1 | 7/2013 | Dobie et al. |
| 2013/0196434 | A1 | 8/2013 | Maier et al. |
| 2014/0288148 | A1 | 9/2014 | Beigelman et al. |
| 2015/0247142 | A1* | 9/2015 | Esau .................... C12N 15/113 536/24.5 |
| 2016/0319278 | A1 | 11/2016 | Khvorova et al. |
| 2017/0043024 | A1 | 2/2017 | Khvorova et al. |
| 2019/0002880 | A1* | 1/2019 | Woolf ............... C12N 15/1137 |
| 2020/0095580 | A1* | 3/2020 | Hauptmann ........... C07H 21/02 |
| 2021/0115442 | A1* | 4/2021 | Khvorova .......... C12N 15/1138 |

FOREIGN PATENT DOCUMENTS

| WO | WO-2016028649 A1 * | 2/2016 | .............. A61P 43/00 |
|---|---|---|---|
| WO | WO 2017/062862 A2 | 4/2017 | |
| WO | WO 2018/031933 A2 | 2/2018 | |

OTHER PUBLICATIONS

Foster et al., "Advanced siRNA Designs Further Improve In Vivo Performance of GalNAc-siRNA Conjugates", Molecular Therapy, vol. 26, No. 3, pp. 709-717, Mar. 2018.

International Search Report and Written Opinion in related PCT Application No. PCT/US2019/048027 dated Nov. 15, 2019 (21 pages).

* cited by examiner

*Primary Examiner* — Brian Whiteman

(74) *Attorney, Agent, or Firm* — Lathrop GPM LLP; James H. Velema, Esq.; Michael Spellberg, Esq.

(57) ABSTRACT

Novel oligonucleotides that are fully chemically stabilized are provided. Methods of using oligonucleotides that are fully chemically stabilized are also provided.

29 Claims, 28 Drawing Sheets

Specification includes a Sequence Listing.

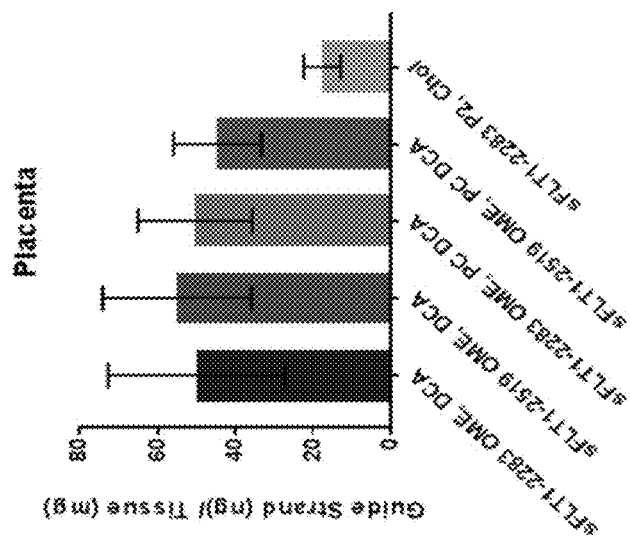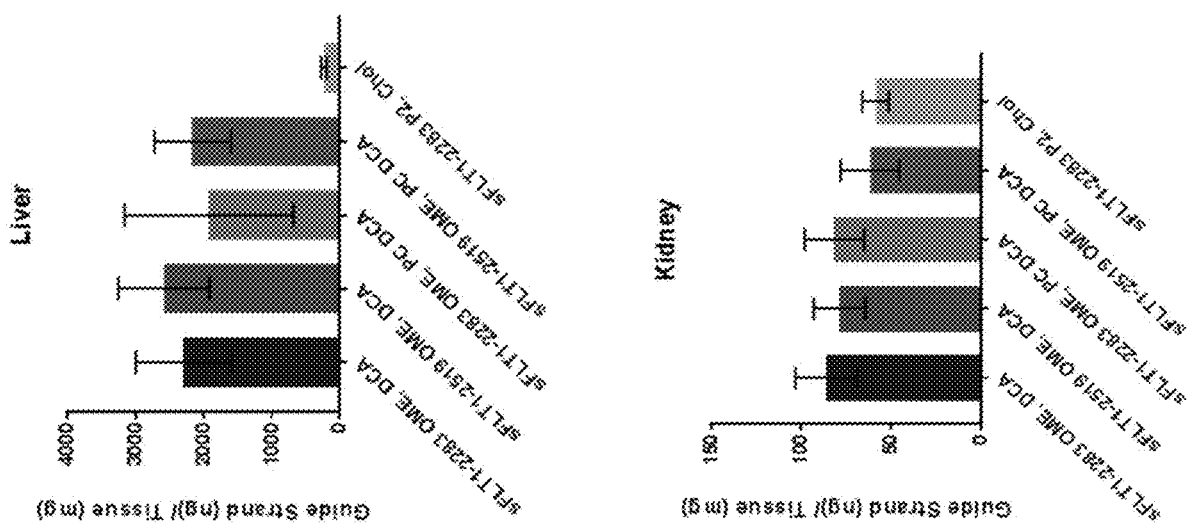
FIG. 6A
FIG. 6B
FIG. 6C

FIG. 12A

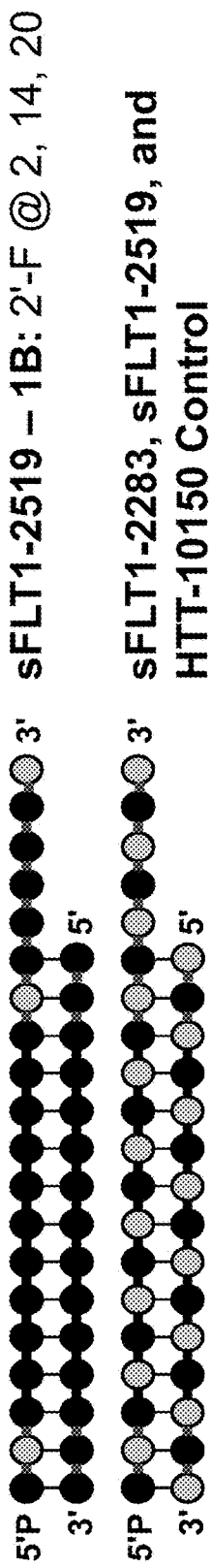

sFLT1-2283, sFLT1-2519, and HTT-10150 siRNA chemical patterns:

sFLT1-2519 – 1B: 2'-F @ 2, 14, 20 sFLT1-2283, sFLT1-2519, and HTT-10150 Control sFLT1-2283 and sFLT1-2519 siRNA Low Phosphorothioate (PS) content:
*Same as above, except 2 instead of 7 PS on the guide strand 3' end*

- ● 2'-O-methyl
- ◐ 2'-fluoro
- ✕ phosphorothioate
- ■ phosphodiester

Chemical conjugates included in study:

*PC-Docosanoic acid (PC-DCA)*

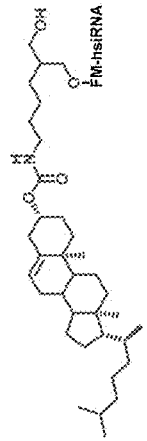

*Cholesterol (Chol)* siRNA guide strand 5' ends:

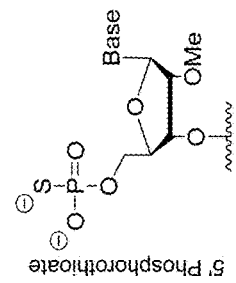

5' Phosphorothioate

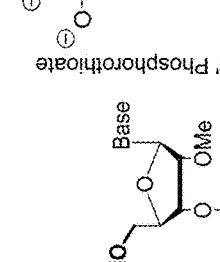

5'-Hydroxyl

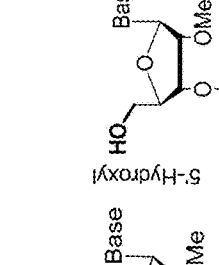

5' Vinyl Phosphonate

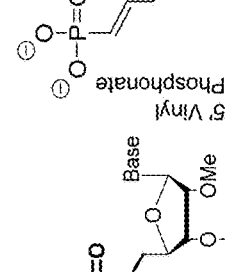

5' Phosphate

O-METHYL RICH FULLY STABILIZED OLIGONUCLEOTIDES

CROSS REFERENCE TO RELATED APPLICATION

This application claims the benefit of U.S. Provisional Patent Application Ser. No. 62/721,993, filed Aug. 23, 2018, which is herein incorporated by reference in its entirety.

STATEMENT REGARDING FEDERALLY FUNDED RESEARCH

This invention was made with government support under Grant numbers NS104022, HD086111 and OD020012 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Dec. 9, 2019, is named UM9-232-616107_SL.txt and is 56,255 bytes in size.

TECHNICAL FIELD

This disclosure relates to novel oligonucleotides useful for RNA silencing, e.g., RNA interference (RNAi), consisting of fully chemically-modified nucleotides. The chemically-modified nucleotides and linkers are patterned to achieve unexpectedly high efficacy, uptake and tissue distribution.

BACKGROUND

Oligonucleotides comprising chemically-modified ribonucleotides (e.g., 2'-fluoro and 2'-methoxy modifications) and/or chemically-modified linkers (e.g., a phosphorothioate modification) are known to exhibit increased nuclease resistance relative to the corresponding unmodified oligonucleotides, while maintaining the ability to promote RNAi. See, e.g., Fosnaugh, et al. (U.S. Publication No. 2003/0143732). Oligonucleotides comprising alternating chemically-modified nucleotides are known. See, e.g., Bhat et al. (U.S. Publication No. 2008/0119427). Hydrophobic modification of therapeutic RNA (e.g., siRNA) is known. See, e.g., Khvorova, et al. (PCT/US2009/005247).

There remains a need for self-delivering oligonucleotides that are characterized by efficient RNA-Induced Silencing Complex (RISC) entry, minimum immune response and off-target effects, efficient cellular uptake without formulation and efficient and specific tissue distribution.

SUMMARY

The present invention is based on the discovery of chemically-modified oligonucleotides that can function as new class of oligonucleotide therapeutics. Surprisingly, it was discovered that nearly fully 2'-O-methyl modified, asymmetric siRNAs having non-2'-O-methyl modifications (e.g., 2'-fluoro modifications, 2'-H modifications, 2'-OH moiety or the like) at positions 2 and 14 from the 5' end of the antisense strand provided unexpected improvements in efficacy properties. This modification pattern can be used to increase efficacy of a variety of oligonucleotide therapeutics including, but not limited to, asymmetric siRNAs, symmetric siRNAs, antisense oligonucleotides (ASOs), microRNAs (miRNAs), miRNA inhibitors, splice switching, phosphorodiamidate morpholino oligomers (PMOs), peptide nucleic acids (PNAs) and the like.

Accordingly, in one aspect the invention provides an oligonucleotide comprising at least 14 contiguous nucleotides, a 5' end and a 3' end; and at least 85% 2'-O-methyl nucleotide modifications; wherein the nucleotides at positions 2 and 14 from the 5' end of the oligonucleotide comprise a non-2'-O-methyl modification.

In certain embodiments, the oligonucleotide comprises an antisense oligonucleotide (ASO).

In certain embodiments, the oligonucleotide comprises perfect or less than perfect complementarity to a target.

In certain embodiments, the target comprises mammalian or viral mRNA.

In certain embodiments, the nucleotide at position 20 from the 5' end of the oligonucleotide comprises a non-2'-O-methyl modification.

In certain embodiments, one or more nucleotides at positions 1-7 from the 3' end of the oligonucleotide are connected to adjacent nucleotides via phosphorothioate linkages In certain embodiments, the nucleotides at positions 1-6 from the 3' end or 1-7 from the 3' end of the oligonucleotide are connected to adjacent nucleotides via phosphorothioate linkages.

In certain embodiments, the nucleotides at positions 2 and 14 from the 5' end of the oligonucleotide comprise a 2'-F modification or 2'-H modification, or a 2'-OH moiety.

In certain embodiments, the nucleotides at positions 2 and 14 from the 5' end of the oligonucleotide comprise a 2'-F modification.

In certain embodiments, the nucleotides at positions 2 and 14 from the 5' end of the oligonucleotide comprise a 2'-H modification.

In certain embodiments, the nucleotides at positions 2 and 14 from the 5' end of the oligonucleotide comprise a 2'-OH moiety.

In certain embodiments, the oligonucleotide comprises at least 90% 2'-O-methyl modified nucleotides.

In certain embodiments, the oligonucleotide further comprises a complementary second oligonucleotide comprising at least 13 contiguous nucleotides, and a 5' end and a 3' end.

In certain embodiments, the second oligonucleotide comprises at least 80% 2'-O-methyl modified nucleotides. In certain embodiments, the second oligonucleotide comprises at least 90% 2'-O-methyl modified nucleotides. In certain embodiments, the second oligonucleotide comprises 100% 2'-O-methyl modified nucleotides.

In certain embodiments, one or more of the nucleotides at positions 7, 9, 10, and 11 from the 3' end of the second oligonucleotide comprise a non-2'-O-methyl modification.

In certain embodiments, one or more of the nucleotides at positions 7, 10, and 11 from the 3' end of the second oligonucleotide comprise a non-2'-O-methyl modification.

In certain embodiments, the nucleotides at positions 7, 10, and 11 from the 3' end of the second oligonucleotide comprise a non-2'-O-methyl modification.

In certain embodiments, the nucleotides at positions 1 and 2 from the 3' end of second oligonucleotide are connected to adjacent nucleotides via phosphorothioate linkages.

In certain embodiments, the nucleotides at positions 1 and 2 from the 3' end of second oligonucleotide, and the nucleotides at positions 1 and 2 from the 5' end of second oligonucleotide, are connected to adjacent nucleotides via phosphorothioate linkages.

In certain embodiments, the second oligonucleotide comprises a hydrophobic molecule at the 3' end of the second oligonucleotide.

In certain embodiments, the oligonucleotide comprises between 15 and 22 contiguous nucleotides. In certain embodiments, the oligonucleotide comprises 20 contiguous nucleotides. In certain embodiments, the oligonucleotide comprises 22 contiguous nucleotides.

In certain embodiments, the second oligonucleotide comprises between 15 and 20 contiguous nucleotides. In certain embodiments, the second oligonucleotide comprises 15 contiguous nucleotides. In certain embodiments, the second oligonucleotide comprises 18 contiguous nucleotides. In certain embodiments, the second oligonucleotide comprises 20 contiguous nucleotides.

In certain embodiments, the second oligonucleotide comprises one or more nucleotide mismatches between the first oligonucleotide and the second oligonucleotide. In certain embodiments, the one or more nucleotide mismatches are present at positions 2, 6, and 12 from the 5' end of the second oligonucleotide. In certain embodiments, the nucleotide mismatches are present at positions 2, 6, and 12 from the 5' end of the second oligonucleotide.

In one aspect, the invention provides an oligonucleotide pharmaceutical composition comprising one or more oligonucleotides described above, and a pharmaceutically acceptable carrier.

In one aspect, the invention provides a method of treating or managing a disease or disorder comprising administering to a subject in need of such treatment or management a therapeutically effective amount of the pharmaceutical composition above.

In one aspect, the invention provides a double-stranded nucleic acid structure comprising an antisense strand and a sense strand, wherein the antisense strand comprises at least 14 contiguous nucleotides, a 5' end and a 3' end; the sense strand comprises at least 13 contiguous nucleotides, a 5' end and a 3' end, and has complementarity to the antisense strand; the antisense strand comprises at least 85% 2'-O-methyl modifications; and the nucleotides at positions 2 and 14 from the 5' end of the antisense strand comprise a non-2'-O-methyl modification.

In certain embodiments, the antisense strand comprises perfect or less than perfect complementarity to the target.

In certain embodiments, the target comprises mammalian or viral mRNA.

In certain embodiments, the nucleotide at position 20 from the 5' end of the antisense strand comprises a non-2'-O-methyl modification.

In certain embodiments, one or more nucleotides at positions 1-7 from the 3' end of the antisense strand are connected to adjacent nucleotides via phosphorothioate linkages.

In certain embodiments, the nucleotides at positions 1-6 from the 3' end or 1-7 from the 3' end of the antisense strand are connected to adjacent nucleotides via phosphorothioate linkages.

In certain embodiments, the nucleotides at positions 2 and 14 from the 5' end of the antisense strand comprise a 2'-F modification or 2'-H modification, or a 2'-OH moiety.

In certain embodiments, the nucleotides at positions 2 and 14 from the 5' end of the antisense strand comprise a 2'-F modification. In certain embodiments, the nucleotides at positions 2 and 14 from the 5' end of the antisense strand comprise a 2'-H modification. In certain embodiments, the nucleotides at positions 2 and 14 from the 5' end of the antisense strand comprise a 2'-OH moiety.

In certain embodiments, the antisense strand comprises at least 90% 2'-O-methyl modified nucleotides.

In certain embodiments, the sense strand comprises at least 80% 2'-O-methyl modified nucleotides. In certain embodiments, the sense strand comprises at least 90% 2'-O-methyl modified nucleotides. In certain embodiments, the sense strand comprises 100% 2'-O-methyl modified nucleotides.

In certain embodiments, one or more nucleotides at positions 7, 9, 10, and 11 from the 3' end of the sense strand comprise a non-2'-O-methyl modification or moiety. In certain embodiments, the nucleotides at positions 7, 9, 10, and 11 from the 3' end of the sense strand comprise a non-2'-O-methyl modification or moiety. In certain embodiments, the nucleotides at positions 7, 10, and 11 from the 3' end of the sense strand comprise a non-2'-O-methyl modification.

In certain embodiments, the nucleotides at positions 1 and 2 from the 3' end of sense strand are connected to adjacent nucleotides via phosphorothioate linkages. In certain embodiments, the nucleotides at positions 1 and 2 from the 3' end of sense strand, and the nucleotides at positions 1 and 2 from the 5' end of sense strand, are connected to adjacent nucleotides via phosphorothioate linkages. In certain embodiments, the sense strand comprises a hydrophobic molecule at the 3' end of the sense strand.

In certain embodiments, the antisense strand comprises between 15 and 22 contiguous nucleotides. In certain embodiments, the antisense strand comprises 20 contiguous nucleotides. In certain embodiments, the antisense strand comprises 22 contiguous nucleotides.

In certain embodiments, the sense strand comprises between 15 and 20 contiguous nucleotides. In certain embodiments, the sense strand comprises 15 contiguous nucleotides. In certain embodiments, the sense strand comprises 18 contiguous nucleotides. In certain embodiments, the sense strand comprises 20 contiguous nucleotides.

In certain embodiments, the sense strand comprises one or more nucleotide mismatches between the antisense strand and the sense strand. In certain embodiments, the one or more nucleotide mismatches are present at positions 2, 6, and 12 from the 5' end of sense strand. In certain embodiments, the nucleotide mismatches are present at positions 2, 6, and 12 from the 5' end of the sense strand. In certain embodiments, the antisense strand comprises a 5' phosphate, a 5'-alkyl phosphonate, or a 5' alkylene phosphonate. In certain embodiments, the antisense strand comprises a 5' vinyl phosphonate.

In certain embodiments, the double-stranded nucleic acid comprises 4-16 phosphorothioate linkages. In certain embodiments, the double-stranded nucleic acid comprises 8-13 phosphorothioate linkages.

In certain embodiments, the double-stranded nucleic acid comprises a double-stranded region of 15 base pairs to 20 base pairs. In certain embodiments, the double-stranded nucleic acid comprises a double-stranded region of 15 base pairs. In certain embodiments, the double-stranded nucleic acid comprises a double-stranded region of 18 base pairs. In certain embodiments, the double-stranded nucleic acid comprises a double-stranded region of 20 base pairs.

In another aspect, the invention provides a double-stranded nucleic acid structure comprising an antisense strand and a sense strand, wherein the antisense strand comprises at least 14 contiguous nucleotides, and a 5' end and a 3' end; the sense strand comprises at least 13 contiguous nucleotides, a 5' end and a 3' end, and has complementarity to the antisense strand; the antisense strand comprises at least 85% 2'-O-methyl modifications; the nucleotides at positions 2 and 14 from the 5' end of the first oligonucleotide are modified with 2'-F; the sense strand comprises 100% 2'-O-methyl modifications; and the nucleotides at positions 1-6 from the 3' end, or positions 1-7 from the 3' end, of the antisense strand are connected to adjacent nucleotides via phosphorothioate linkages.

In another aspect, the invention provides a pharmaceutical composition comprising one or more double-stranded, chemically-modified nucleic acids described above, and a pharmaceutically acceptable carrier.

In another aspect, the invention provides a method of treating or managing a disease or disorder comprising administering to a subject in need of such treatment or management a therapeutically effective amount of the pharmaceutical composition above.

In another aspect, the invention provides a branched oligonucleotide compound capable of mediating RNA silencing in a cell, comprising two or more double-stranded nucleic acids, wherein the nucleic acids (N) are connected to one another by one or more moieties selected from a linker (L), a spacer (S) and optionally a branching point (B), wherein each double-stranded nucleic acid comprises an antisense strand and a sense strand, wherein each antisense strand comprises at least 14 contiguous nucleotides, a 5' end and a 3' end, and at least one antisense strand comprises at least 85% 2'-O-methyl modifications; wherein the nucleotides at positions 2 and 14 from the 5' end of the at least one antisense strand comprise a non-2'-O-methyl modification; and wherein one or more nucleotides at positions 1-7 from the 3' end of at least one antisense strand are connected to adjacent nucleotides via phosphorothioate linkages.

In certain embodiments, each antisense strand comprises at least 85% 2'-O-methyl modifications; the nucleotides at positions 2 and 14 from the 5' end of each antisense strand comprise a non-2'-O-methyl modification; and/or one or more nucleotides at positions 1-7 from the 3' end of each antisense strand are connected to adjacent nucleotides via phosphorothioate linkages.

In certain embodiments, the nucleotides at positions 1 and 2 from the 5' end of the sense and antisense strands are connected to adjacent nucleotides via phosphorothioate linkages.

In certain embodiments, each double-stranded nucleic acid is independently connected to a linker, spacer or branching point at the 3' end or at the 5' end of the sense strand or the antisense strand.

In certain embodiments, the compound further comprises a hydrophobic moiety attached to the terminal 5' position of the branched oligonucleotide compound.

In certain embodiments, the hydrophobic moiety comprises an alkyl, alkenyl, or aryl moiety; a vitamin or cholesterol derivative; a lipophilic amino acid; or a combination thereof.

In certain embodiments, each linker is independently selected from an ethylene glycol chain, an alkyl chain, a peptide, RNA, DNA, a phosphate, a phosphonate, a phosphoramidate, an ester, an amide, a triazole, or combinations thereof; wherein any carbon or oxygen atom of the linker is optionally replaced with a nitrogen atom, bears a hydroxyl substituent, or bears an oxo substituent.

In certain embodiments, the nucleotide at position 20 from the 5' end of the antisense strand comprises a non-2'-O-methyl modification.

In certain embodiments, the nucleotides at position 7, 10, and 11 from the 3' end of the sense strand comprise a non-2'-O-methyl modification or moiety.

In certain embodiments, the non-2'-O-methyl modification comprises a 2'-F modification or 2'-H modification, or 2'-OH moiety. In certain embodiments, the non-2'-O-methyl modification comprises a 2'-F modification. In certain embodiments, the non-2'-O-methyl modification comprises a 2'-H modification. In certain embodiments, the non-2'-O-methyl modification comprises a 2'-OH moiety.

In certain embodiments, the antisense strand comprises at least 90% 2'-O-methyl modified nucleotides.

In certain embodiments, the sense strand comprises at least 80% 2'-O-methyl modified nucleotides. In certain embodiments, the sense strand comprises at least 90% 2'-O-methyl modified nucleotides. In certain embodiments, the sense strand comprises 100% 2'-O-methyl modified nucleotides. In certain embodiments, the antisense strand comprises 15, 16, 17, 18, 19, 20, 21, or 22 contiguous nucleotides. In certain embodiments, sense strand comprises 15, 16, 17, 18, 19, or 20 contiguous nucleotides.

BRIEF DESCRIPTION OF THE DRAWINGS

FIG. 1 schematically depicts Pattern 1A to Pattern 1F, each lacking a 2'-OMe modification at positions 2 and 14 of the guide (antisense) strand. Pattern 1B, Pattern 1D, and Pattern 1F also lack a 2'-OMe modification at the 3' terminal nucleotide of the guide strand. Pattern 1A and Pattern 1B depict an siRNA with a 20-nucleotide guide strand and a 15-nucleotide passenger (sense) strand. Pattern 1C and Pattern 1D depict an siRNA with a 20-nucleotide guide strand and a 18-nucleotide passenger (sense) strand. Pattern 1E and Pattern 1F depict an siRNA with a 22-nucleotide guide strand and a 20-nucleotide passenger (sense) strand.

FIG. 4A shows HeLa cells and FIG. 4B shows melanoma cells that were treated with O-methyl-rich and control siRNAs at the concentrations shown for 72 hours. FIG. 4C schematically depicts F2, 14 siRNA (circles), F2, 4, 5, 6, 8, 14 siRNA (squares) and control siRNA (triangles). mRNA was measured using Promega Dual-Glo® Luciferase (FIG. 4A) or Affymetrix Quantigene 2.0 (FIG. 4B) Assay System. Data was normalized to control reporter (FIG. 4A) housekeeping gene (HPRT) (FIG. 4B) and graphed as a % of untreated control.

FIG. 5A shows HeLa cells and FIG. 5B shows melanoma cells that were treated with O-methyl-rich and control siRNAs at the concentrations shown for 72 hours. mRNA was measured using Promega Dual-Glo® Luciferase (FIG. 5A) or Affymetrix Quantigene 2.0 (FIG. 5B) Assay System. Data was normalized to control reporter (FIG. 5A) housekeeping gene (HPRT) (FIG. 5B) and graphed as a % of untreated control.

FIG. 6A-FIG. 6C depict that O-methyl-rich DCA and PC DCA compounds show increased or similar AS accumulation in the liver (A), kidney (B), and placenta (C) compared to P2 cholesterol, despite ½ dosing. CD1 pregnant mice were treated with O-methyl rich and P2 siRNAs at concentrations shown, and tissues were harvested at indicated times. siRNA guide strands were measured in tissues using a peptide nucleic acid (PNA) hybridization assay. sFLT1-2283 O-methyl-rich: 20 mg/kg*, 120-hour dose; sFLT1-2519 O-methyl-rich: 20 mg/kg*, 120-hour dose. sFLT1-2283 P2: 20 mg/kg**, 120-hour dose. *40 mg/kg was the total dose of sFLT1-X siRNA (20 mg/kg sFLT1-2283+20 mg/kg sFLT1-2519a on E14). **20 mg/kg was the total dose of sFLT1-2283 siRNA (10 mg/kg sFLT1-2283 on E14+10 mg/kg sFLT1-2283 on E15).

FIG. 9A shows HeLa cells and FIG. 9B shows WM-115 cells that were treated with Pattern 1A and control siRNAs at the concentrations shown for 72 hours. mRNA was measured using Promega Dual-Glo® Luciferase (FIG. 9A) or Affymetrix Quantigene 2.0 (FIG. 9B) Assay System. Data was normalized to control reporter (fLuc) (FIG. 9A) or a housekeeping gene (HPRT) (FIG. 9B) and graphed as a % of untreated control.

FIG. 10A shows HeLa cells and FIG. 10B shows WM-115 cells that were treated with Pattern 1A and control siRNAs at the concentrations shown for 72 hours. mRNA was measured using Promega Dual-Glo® Luciferase (FIG. 10A) or Affymetrix Quantigene 2.0 (FIG. 10B) Assay System. Data was normalized to control reporter (fLuc) (FIG. 10A) or a housekeeping gene (HPRT) (FIG. 10B) and graphed as a % of untreated control.

FIG. 11A depicts the Pattern 1A and control schematics.

FIG. 11B depicts the increased guide strand accumulation in the liver, kidney, and placenta compared to a control. CD1 pregnant mice were treated with Pattern 1A or control siRNAs at concentrations shown, and tissues were harvested at indicated times. siRNA guide strands were measured in tissues using a peptide nucleic acid (PNA) hybridization assay. sFLT1-2283 O-methyl-rich: 20 mg/kg*, 120-hour dose; sFLT1-2283 control: 20 mg/kg**, 120-hour dose. *40 mg/kg was the total dose of sFLT1-X siRNA (20 mg/kg sFLT1-2283+20 mg/kg sFLT1-2519a on E14). **20 mg/kg was the total dose of sFLT1-2283 siRNA (10 mg/kg sFLT1-2283 on E14+10 mg/kg sFLT1-2283 on E15).

FIG. 11C depicts the increased guide strand accumulation in the placenta compared to a control. The conditions are the same as FIG. 11B, except the sFLT1-2283 control was dosed at 10 mg/kg**, 120-hour dose.

FIG. 11D depicts the increased guide strand accumulation in the liver and similar guide strand accumulation in the placenta compared to a control. The conditions are the same as FIG. 11B, except HTT-10150 DCA and PC-DCA controls were used; 20 mg/kg**, 48-hour dose.

FIG. 12A-FIG. 12B depict that Pattern 1B PC DCA siRNAs show increased guide strand accumulation in the placenta compared to a control pattern with a cholesterol or PC DCA conjugate, despite ½ dosing.

FIG. 12A depicts the Pattern 1B and control schematics.

FIG. 12B depicts the increased guide strand accumulation in the placenta compared to a control. CD1 pregnant mice were treated with Pattern 1B or control siRNAs and tissues were harvested. siRNA guide strands were measured in tissues using a peptide nucleic acid (PNA) hybridization assay. sFLT1-2519 O-methyl-rich: 20 mg/kg*, 120-hour dose; sFLT1-2283 control: 20 mg/kg**, 120-hour dose; HTT-10150 control PC DCA: 20 mg/kg, 48-hour dose. *40 mg/kg was the total dose of sFLT1-X siRNA (20 mg/kg sFLT1-2283+20 mg/kg sFLT1-2519a on E14). **20 mg/kg was the total dose of sFLT1-2283 siRNA (10 mg/kg sFLT1-2283 on E14+10 mg/kg sFLT1-2283 on E15).

FIG. 13A, FIG. 13C, and FIG. 13D shows HeLa cells and FIG. 13B shows WM-115 cells that were treated with siRNAs that contain between 50-55% 2'-OMe content in the guide strand at the concentrations shown for 72 hours. FIG. 13D compares an siRNA with a 20-nucleotide antisense strand to a siRNA with a 21-nucleotide antisense strand. mRNA was measured using Promega Dual-Glo® Luciferase or Affymetrix Quantigene 2.0 Assay System. Data was normalized to control reporter (fLuc) or a housekeeping gene (HPRT) and graphed as a % of untreated control.

DETAILED DESCRIPTION

Figure 1:
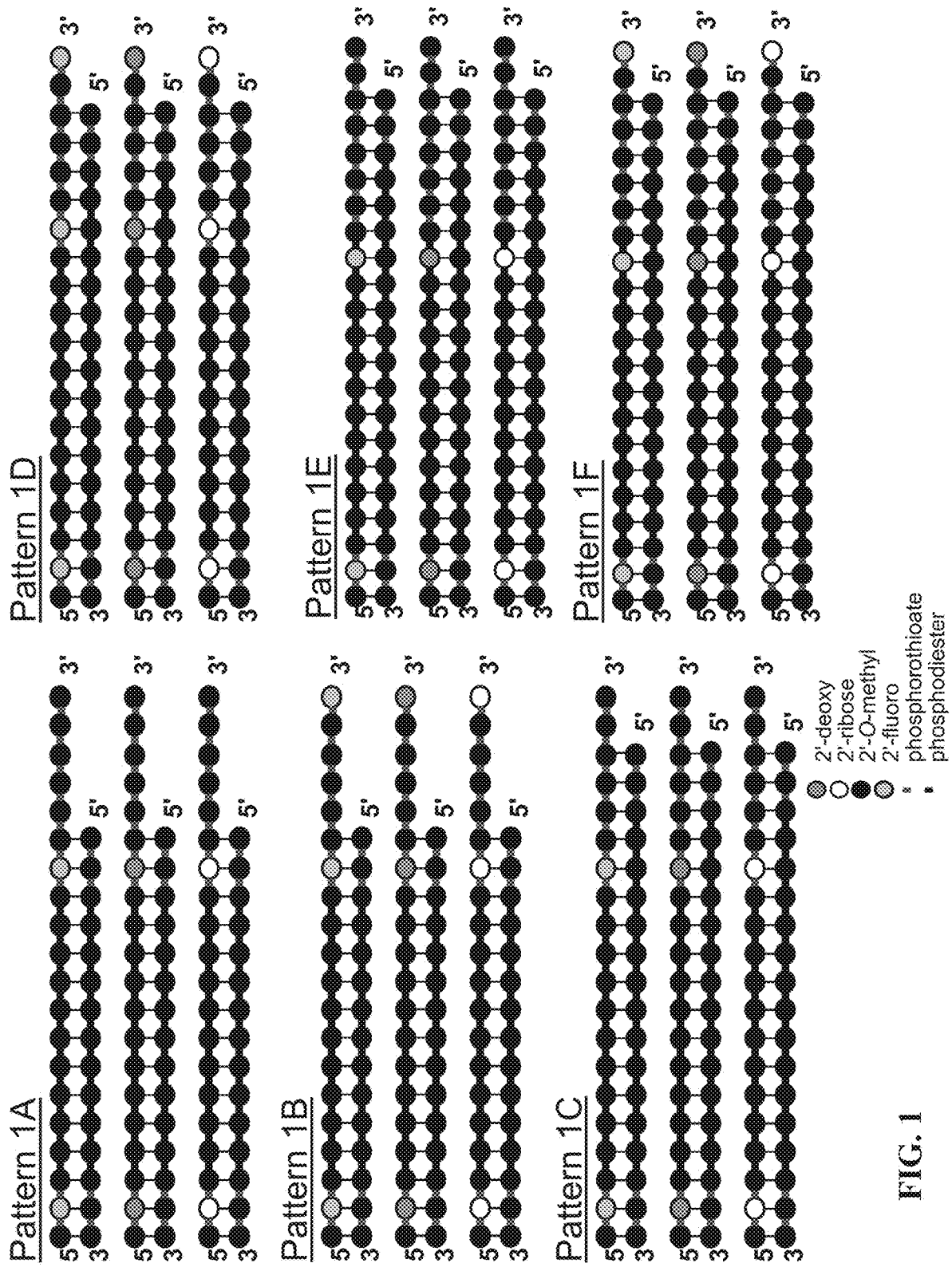
FIG. 1 schematically depicts a fully chemically stabilized siRNA pattern (Pattern 1) containing two 2'-fluoro modification at positions 2 and 14 of the guide (antisense) strand according to certain exemplary embodiments (top). 2'-fluoro-free configurations where positions 2 and 14 are modified with ribose (middle) and DNA (bottom) are also depicted.

Provided herein are oligonucleotides comprising a novel chemical configuration that is fully chemically stabilized and contains only two non-2'-O-methyl modifications (e.g., 2'-fluoro modifications) at positions 2 and 14 of the antisense strand (FIG. 1). Without intending to be bound by scientific theory, positions 2 and 14 of the antisense strand form direct contacts with AGO2. Unexpectedly, it was discovered that this chemical configuration was fully functional in the context of mRNA silencing. In addition, 2'-fluoro-free configurations where positions 2 and 14 are modified with ribose and/or DNA were also discovered. The use of the novel oligonucleotides described herein will not only enhance the duration of efficacy in vivo, but also reduce concerns about the toxicity of oligonucleotides comprising a high percentage of 2'-fluoro modifications.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included," is not limiting. As used herein, unless otherwise stated, the singular forms "a," "an," and "the" include plural reference. Thus, for example, a reference to "a protein" includes a plurality of protein molecules.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The term "complementary" refers to the relationship between nucleotides exhibiting Watson-Crick base pairing, or to oligonucleotides that hybridize via Watson-Crick base pairing to form a double-stranded nucleic acid. The term "complementarity" refers to the state of an oligonucleotide (e.g., a sense strand or an antisense strand) that is partially or completely complementary to another oligonucleotide. Oligonucleotides described herein as having complementarity to a second oligonucleotide may be 100% (perfect complementarity), >95%, >90%, >85%, >80%, >75%, >70%, >65%, >60%, >55% or >50% complementary to the second oligonucleotide. Accordingly, oligonucleotides described herein as having less than 100% complementarity to a second oligonucleotide have less than perfect complementarity.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base cytosine (e.g., cytidine or a chemically-modified derivative thereof).

As used herein, the term "3' end" refers to the end of a nucleic acid that contains an unmodified hydroxyl group at the 3' carbon of its ribose ring. The 3' end can be covalently linked to another molecule, such as hydrophobic molecule or another nucleic acid (e.g., via a linker).

As used herein, the term "5' end" refers to the end of a nucleic acid that contains a phosphate group attached to the 5' carbon of its ribose ring. The 5' end can be further modified by a hydrophobic, phosphonate, linker, alkylene, or alkenyl moiety.

As used herein, the term "nucleoside" refers to a molecule made up of a heterocyclic base and its sugar.

As used herein, the term "nucleotide" refers to a nucleoside typically having a phosphate or phosphorothioate group on its 3' or 5' sugar hydroxyl group.

An RNAi agent, e.g., an siRNA, having a strand which is "sequence sufficiently complementary to a target mRNA sequence to direct target-specific RNA interference (RNAi)" means that the strand has a sequence sufficient to trigger the destruction of the target mRNA by RNAi.

As used herein, the term "isolated RNA" (e.g., "isolated siRNA," "isolated siRNA" or "isolated siRNA precursor") refers to an RNA molecule that is substantially free of other cellular material, or culture medium when produced by recombinant techniques, or substantially free of chemical precursors or other chemicals when chemically synthesized.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence, e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

As used herein, the term "siRNA" refers to small interfering RNAs that induce the RNA interference (RNAi) pathway. siRNA molecules can vary in length (generally between 15-30 basepairs) and contain varying degrees of complementarity to their target mRNA. The term "siRNA" includes duplexes of two separate strands, as well as single strands that can form hairpin structures comprising a duplex region.

As used herein, the term "antisense strand" refers to the strand of an siRNA duplex that contains some degree of complementarity to a target gene or mRNA and contains complementarity to the sense strand of the siRNA duplex. The nucleotide positions of the antisense strand may be referenced from the 5' end of the antisense strand or the 3' end of the antisense strand. For example, positions 2 and 14 from the 5' end of the antisense strand correspond to the $2^{nd}$ and $14^{th}$ nucleotides when counted from the 5' end of the antisense strand.

As used herein, the term "sense strand" refers to the strand of an siRNA duplex that contains complementarity to the antisense strand of the siRNA duplex. The nucleotide positions of the sense strand may be referenced from the 5' end of the sense strand or the 3' end of the sense strand. For example, positions 7, 10, and 11 from the 3' end of the sense strand correspond to the $7^{th}$, $10^{th}$, and $11^{th}$ nucleotides when counted from the 3' end of the sense strand. In some cases, where the sense strand comprises a 3' single-stranded overhang region, positions described herein in reference to the 3' end, are in reference to the 3' end of the double-stranded region of the sense strand.

As used herein, the term "overhang" or "tail" refers to 3, 4, 5, 6, 7, 8, 9, 10, 11, 12, 13, 14, 15, 16, 17, 18, 19, 20 or more sequential nucleotides at the 3' end of one or both of the sense strand and the antisense strand that are single-stranded, i.e., are not base paired to (i.e., do not form a duplex with) the other strand of the siRNA duplex.

As used herein, the term "antisense oligonucleotide" or "ASO" refers to a nucleic acid (e.g., an RNA), having sufficient sequence complementarity to a target an RNA (e.g., a SNP-containing mRNA or a SNP-containing pre-mRNA) in order to block a region of a target RNA in an effective manner, e.g., in a manner effective to inhibit translation of a target mRNA and/or splicing of a target pre-mRNA. An antisense oligonucleotide having a "sequence sufficiently complementary to a target RNA" means that the antisense agent has a sequence sufficient to mask a binding site for a protein that would otherwise modulate splicing and/or that the antisense agent has a sequence sufficient to mask a binding site for a ribosome and/or that the antisense agent has a sequence sufficient to alter the three-dimensional structure of the targeted RNA to prevent splicing and/or translation.

In certain exemplary embodiments, an siRNA of the invention is asymmetric. In certain exemplary embodiments, an siRNA of the invention is symmetric.

In certain exemplary embodiments, an siRNA of the invention comprises a duplex region of between about 8-20 nucleotides or nucleotide analogs in length, between about 10-18 nucleotides or nucleotide analogs in length, between about 12-16 nucleotides or nucleotide analogs in length, or between about 13-15 nucleotides or nucleotide analogs in length (e.g., a duplex region of about 8, 9, 10, 11, 12, 13, 14, 15, 16, 17, 18, 19 or 20 base pairs). In certain exemplary embodiments, an siRNA of the invention comprises a duplex region of 13-25 base pairs. In certain exemplary embodiments, an siRNA of the invention comprises a duplex region of 15-20 base pairs. In certain exemplary embodiments, an siRNA of the invention comprises a duplex region of 15 base pairs.

In certain exemplary embodiments, an siRNA of the invention comprises one or two overhangs. In certain embodiments, each overhang of the siRNA comprises at least about 3, about 4, about 5, about 6, about 7, about 8, about 9, or about 10 sequential nucleotides. In certain embodiments, each overhang of the siRNA of the invention is about 4, about 5, about 6 or about 7 nucleotides in length. In certain embodiments, the sense strand overhang is the same number of nucleotides in length as the antisense strand overhang. In other embodiments, the sense strand overhang has fewer nucleotides than the antisense strand overhang. In other embodiments, the antisense strand overhang has fewer nucleotides than the sense strand overhang. In certain embodiments, each nucleotide in an overhang region is conjugated to its adjacent nucleotide via a phosphorothioate linkage.

In certain exemplary embodiments, an siRNA of the invention comprises a sense strand and/or an antisense strand each independently having a length of, or of about, 10; of, or of about, 15; of, or of about 20; of, or of about, 25; or of, or of about, 30 nucleotides. In particular embodiments, an siRNA of the invention comprises a sense strand and/or an antisense strand each independently having a length of from, or from about, 15 to 25 or about 25 nucleotides. In particular embodiments, an siRNA of the invention comprises a sense strand and an antisense strand that are each independently 20 or about 20 nucleotides in length. In certain embodiments, the sense strand and the antisense strand of an siRNA are the same length. In other embodiments, the sense strand and the antisense strand of an siRNA are different lengths.

In certain exemplary embodiments, an siRNA of the invention comprises an antisense strand having a length of greater than 15 nucleotides and comprising or consisting of at least 85% 2'-O-methyl modified nucleotides, and a sense strand having a length that is shorter than the antisense strand, wherein the length of the sense strand is at least about 8, 9, 10, 11, 12, 13, 14, 15, 16, 17, 18, 19, or 20 nucleotides. In particular embodiments, an siRNA of the invention comprises an antisense strand having a length of about 16, 17, 18, 19, 20, 21, 22, 23, 24, or 25 nucleotides. In particular embodiments, an siRNA of the invention comprises an antisense strand having at least 85% 2'-O-methyl modified nucleotides and a length of from about 18 to about 25 nucleotides, and a sense strand having a length of from about 13 to about 20 nucleotides. In particular embodiments, an siRNA of the invention comprises an antisense strand that is about 20 nucleotides in length and a sense strand that is about 15 nucleotides in length. In particular embodiments, an siRNA of the invention comprises an antisense strand that is about 20 nucleotides in length and a sense strand that is about 18 nucleotides in length.

In particular embodiments, an siRNA of the invention comprises an antisense strand that is about 22 nucleotides in length and a sense strand that is about 20 nucleotides in length.

As used herein, the terms "chemically modified nucleotide" or "nucleotide analog" or "altered nucleotide" or "modified nucleotide" refer to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; 0- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group (2'-hydroxy) may be replaced by a group selected from H (2'-deoxy), OR, R, F (2'-fluro), Cl, Br, I, SH, SR, $NH_2$, NHR, $NR_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

As used herein, the term "metabolically stabilized" refers to RNA molecules that contain 2'-ribose modifications to replace native 2'-hydroxyl groups with 2'-O-methyl groups or 2'-fluoro groups. Similarly, the term "stabilized" refers to RNA molecules that contain a 2'-ribose modification to replace 2'-hydroxyl groups with a 2'-O-methyl or a group that is not 2'-O-methyl and not 2-hydroxyl. The term "fully stabilized" or "fully modified" refers to RNA molecules that contain a 2'-modification at each position, and are typically at least 85% 2'-O-methyl modified. In certain embodiments, fully stabilized RNA molecules may contain 1, 2, or 3 non-2'-O-methyl modified nucleotides such as 2'-F or 2'-H modified nucleotides. The term "nearly fully stabilized" or "nearly fully modified" refers to RNA molecules that contain 1, 2, or 3 positions that do not have a 2'-modification, and are typically at least 85% 2'-O-methyl modified. Oligonucleotides described herein can be stabilized, metabolically stabilized, nearly fully stabilized, and/or fully stabilized.

In particular embodiments, the duplex region of an siRNA comprises one or two 2'-fluoro modifications and/or at least about 86%, at least about 87%, at least about 88%, at least about 89%, at least about 90%, at least about 91%, at least about 92%, at least about 93% or at least about 94% 2'-methoxy (2'-O-methyl) modifications. In certain exemplary embodiments, the antisense strand comprises two 2'-fluoro modifications and at least about 90%, at least about 91%, at least about 92%, at least about 93% or at least about 94% 2'-methoxy modifications. In certain exemplary embodiments, the sense strand comprises at least about 91%, at least about 92%, at least about 93%, at least about 94%, at least about 95%, at least about 96%, at least about 97%, at least about 98%, at least about 99% or about 100% 2'-methoxy modifications. In certain exemplary embodiments, a single-stranded oligonucleotide is provided that comprises two 2'-fluoro modifications and at least about 90%, at least about 91%, at least about 92%, at least about 93% or at least about 94% 2'-methoxy modifications.

In a particularly exemplary embodiment, an oligonucleotide is provided that comprises a 2'-fluoro modification at the nucleotide at each of positions 2 and 14 from the 5' end, and a 2'-methoxy modification at each other nucleotide position. In certain exemplary embodiments, an antisense strand is provided that comprises three 2'-fluoro modifications and at least about 85% non-2'-fluoro modifications (e.g., at least about 85% 2'-methoxy modifications). In certain exemplary embodiments, an antisense strand is provided that comprises two or three non-2'-O-methyl modifications (2'-F, 2'-H, or 2'-OH) and at least about 85% 2'-methoxy modifications.

As used herein, the term "phosphorothioate" refers to the phosphate group of a nucleotide that is modified by substituting one or more of the oxygens of the phosphate group with sulfur. A phosphorothioate further comprises a cationic counter-ion (e.g., sodium, potassium, calcium, magnesium or the like). The term "phosphorothioated nucleotide" refers to a nucleotide having one or two phosphorothioate linkages to another nucleotide. In certain embodiments, the single-stranded tails of the siRNAs of the invention comprise or consist of phosphorothioated nucleotides. In certain embodiments, double stranded oligonucleotides described herein comprise 1, 2, 3, 4, or 5 phosphorothioated nucleotides in the double-stranded region. In certain embodiments, double stranded oligonucleotides described herein comprise 1, 2, 3, 4, or 5 phosphorothioated nucleotides in the double-stranded region and one or more single-stranded tails that comprise or consist of phosphorothioated nucleotides.

Figure 3:
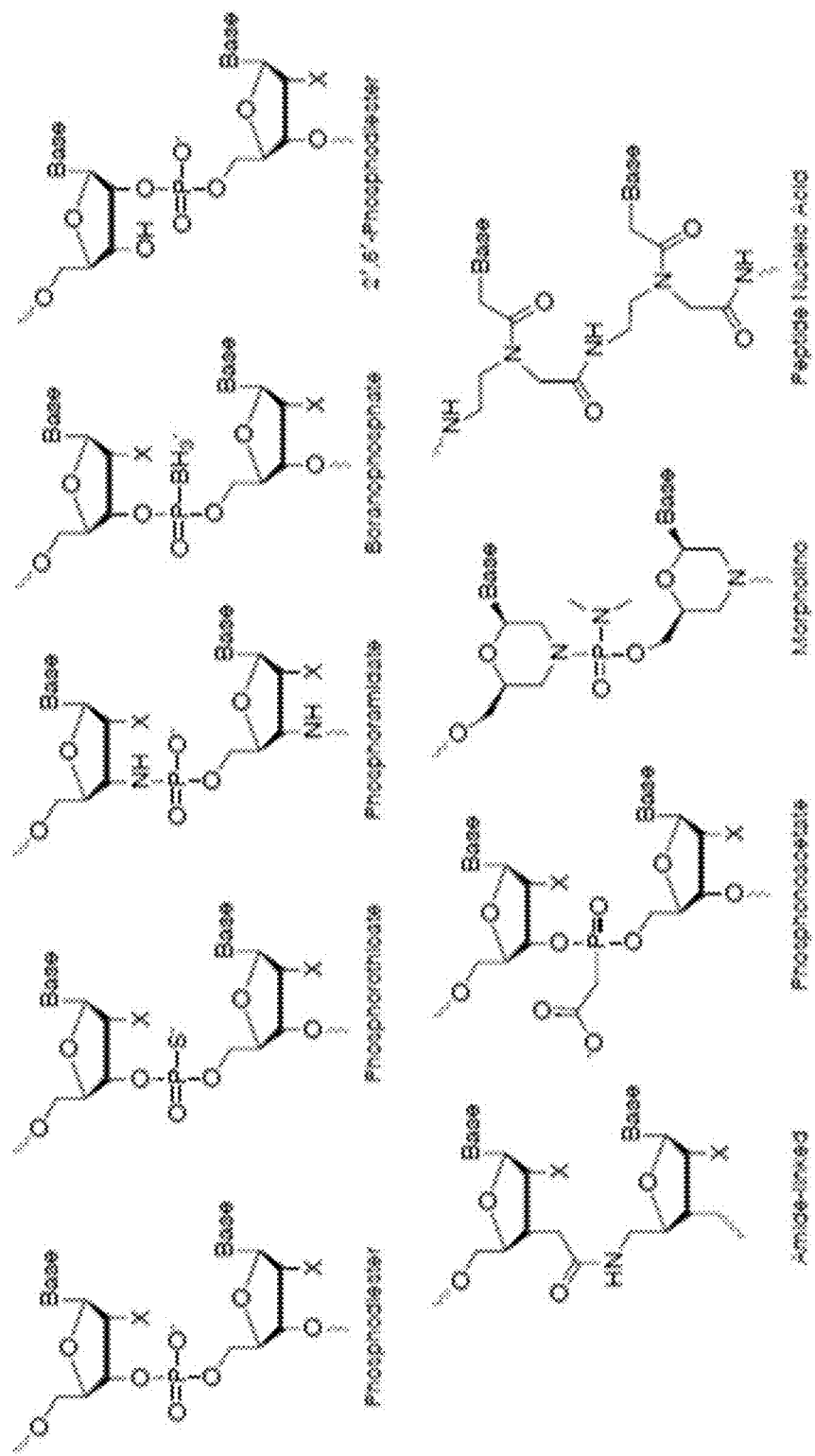
FIG. 3 depicts oligonucleotide backbone linkages according to certain exemplary embodiments.

In some embodiments, the compounds, oligonucleotides and nucleic acids described herein may be modified to comprise one or more internucleotide linkages provided in FIG. 3. In particular embodiments, the compounds, oligonucleotides and nucleic acids described herein comprise one or more internucleotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

As used herein, the term "lipid formulation" may refer to liposomal formulations, e.g., wherein liposomes are used to form aggregates with nucleic acids in order to promote penetration of the nucleic acids into a cell. Without being bound by theory, liposomes are useful for penetration into a cell because the phospholipid bilayer readily merges with the phospholipid bilayer of the cell membrane, thereby allowing the nucleic acids to penetrate the cell.

siRNA Pattern 1

Pattern 1 and exemplary Pattern 1A to Pattern 1F embodiments are reproduced below, where "mN" is a 2'-O-methyl modified nucleotide, "xN" is a non-2'-O-methyl modified nucleotide, such as a 2'-fluoro modified nucleotide or a 2'-deoxy modified nucleotide, "#" is a phosphorothioate backbone modification, and "N" is a nucleotide selected from A, U, G, or C:

```
Pattern 1
Antisense 5' to 3'
                                           (SEQ ID NO: 1)
(mN) (xN) (mN) (mN) (mN) (mN) (mN) (mN) (mN) (mN) (mN) (mN)
(mN) (xN) (mN) (mN) (mN) (mN) (mN) (mN)

Sense 5' to 3'
                                           (SEQ ID NO: 2)
(mN) (mN) (mN) (mN) (mN) (mN) (mN) (mN) (mN) (mN) (mN) (mN)
(mN) (mN) (mN)
```

In certain embodiments, Pattern 1 above may comprise an antisense strand of 20 to 22 nucleotides, where the antisense strand is extended from the 3' end with 2'-O-methyl modified nucleotides. A 20-nucloetide antisense strand is represented above. In certain embodiments, Pattern 1 above may comprise a sense strand of 15 to 20 nucleotides, where the sense strand is extended from the 3' end with 2'-O-methyl modified nucleotides. A 15-nucloetide sense strand is represented above. In certain embodiments, the antisense strand above may comprise one or more phosphorothioate linkages, #, at the 5' and/or 3' end. In certain embodiments, the sense strand above may comprise one or more phosphorothioate linkages, #, at the 5' and/or 3' end. In certain embodiments, the 5' terminal nucleotide of the antisense strand may comprise a 5' vinyl phosphonate, a 5' OH, or a 5' phosphorothioate (5' PS). In certain embodiments, the 3' terminal nucleotide of the antisense strand may comprise a non-2'-O-methyl modified nucleotide. In further embodiments, the siRNA of Pattern 1 may be in a branched siRNA structure, comprising two or more linked Pattern 1 siRNAs. In a particular embodiment, the Pattern 1 siRNA is a di-branched Pattern 1 siRNA comprising two Pattern 1 siRNAs with a linker connecting the two siRNAs via the 3' end of the sense strand.

Exemplary Pattern 1 embodiments (Pattern 1A, 1B, 1C, 1D, 1E, and 1F), are shown below:

```
Pattern 1A
Antisense 5' to 3' (20 nucleotides)
                                             (SEQ ID NO: 3)
(mN)#(xN)#(mN)(mN)(mN)(mN)(mN)(mN)(mN)(mN)
(mN)(mN)#(xN)#(mN)#(mN)#(mN)#(mN)#(mN)#(mN)

Sense 5' to 3' (15 nucleotides)
                                             (SEQ ID NO: 4)
(mN)#(mN)#(mN)(mN)(mN)(mN)(mN)(mN)(mN)(mN)
(mN)(mN)#(mN)#(mN)

Pattern 1B
Antisense 5' to 3' (20 nucleotides)
                                             (SEQ ID NO: 5)
(mN)#(xN)#(mN)(mN)(mN)(mN)(mN)(mN)(mN)(mN)
(mN)(mN)#(xN)#(mN)#(mN)#(mN)#(mN)#(mN)#(xN)

Sense 5' to 3' (15 nucleotides)
                                             (SEQ ID NO: 4)
(mN)#(mN)#(mN)(mN)(mN)(mN)(mN)(mN)(mN)(mN)
(mN)(mN)#(mN)#(mN)

Pattern 1C
Antisense 5' to 3' (20 nucleotides)
                                             (SEQ ID NO: 3)
(mN)#(xN)#(mN)(mN)(mN)(mN)(mN)(mN)(mN)(mN)
(mN)(mN)#(xN)#(mN)#(mN)#(mN)#(mN)#(mN)#(mN)

Sense 5' to 3' (18 nucleotides)
                                             (SEQ ID NO: 6)
(mN)#(mN)#(mN)(mN)(mN)(mN)(mN)(mN)(mN)(mN)
(mN)(mN)(mN)(mN)(mN)#(mN)#(mN)

Pattern 1D
Antisense 5' to 3' (20 nucleotides)
                                             (SEQ ID NO: 5)
(mN)#(xN)#(mN)(mN)(mN)(mN)(mN)(mN)(mN)(mN)
(mN)(mN)#(xN)#(mN)#(mN)#(mN)#(mN)#(mN)#(xN)

Sense 5' to 3' (18 nucleotides)
                                             (SEQ ID NO: 6)
(mN)#(mN)#(mN)(mN)(mN)(mN)(mN)(mN)(mN)(mN)
(mN)(mN)(mN)(mN)(mN)#(mN)#(mN)

Pattern 1E
Antisense 5' to 3' (22 nucleotides)
                                             (SEQ ID NO: 7)
(mN)#(xN)#(mN)(mN)(mN)(mN)(mN)(mN)(mN)(mN)
(mN)(mN)(xN)(mN)#(mN)#(mN)#(mN)#(mN)#(mN)#(mN)
(mN)

Sense 5' to 3' (20 nucleotides)
                                             (SEQ ID NO: 8)
(mN)#(mN)#(mN)(mN)(mN)(mN)(mN)(mN)(mN)(mN)
(mN)(mN)(mN)(mN)(mN)(mN)(mN)#(mN)#(mN)

Pattern 1F
Antisense 5' to 3' (22 nucleotides)
                                             (SEQ ID NO: 9)
(mN)#(xN)#(mN)(mN)(mN)(mN)(mN)(mN)(mN)(mN)
(mN)(mN)(xN)(mN)#(mN)#(mN)#(mN)#(mN)#(mN)#(mN)
(xN)

Sense 5' to 3' (20 nucleotides)
                                             (SEQ ID NO: 8)
(mN)#(mN)#(mN)(mN)(mN)(mN)(mN)(mN)(mN)(mN)
(mN)(mN)(mN)(mN)(mN)(mN)(mN)#(mN)#(mN)
``` siRNA Design

In some embodiments, an oligonucleotide molecule of the invention is an siRNA duplex consisting of a sense strand and complementary antisense strand, the antisense strand having sufficient complementary to an mRNA to mediate RNAi. In certain exemplary embodiments, each strand of the siRNA molecule independently has a length from about 10-50 or more nucleotides, i.e., each strand independently comprises 10-50 nucleotides (or nucleotide analogs or combinations of nucleotides and nucleotide analogs). In other exemplary embodiments, the siRNA molecule has a length from about 16-30, e.g., independently 16, 17, 18, 19, 20, 21, 22, 23, 24, 25, 26, 27, 28, 29, or 30 nucleotides in each strand, wherein one of the strands is sufficiently complementary to a target region to mediate RNAi.

In certain exemplary embodiments, the strands are aligned such that there are at least 4, 5, 6, 7, 8, 9, 10 or more bases at the end of one or both the strands do not align (i.e., for which no complementary bases occur in the opposing strand) such that an overhang of 4, 5, 6, 7, 8, 9, 10 or more residues occurs at one of or both ends of the duplex when strands are annealed. In certain exemplary embodiments, the siRNA molecule has a length from about 10-50 or more nucleotides, i.e., each strand independently comprises 10-50 nucleotides (or nucleotide analogs or combinations of nucleotides and nucleotide analogs). In particularly exemplary embodiments, the siRNA molecule independently has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

In other exemplary embodiments, the siRNA molecule has a length from about 15 to about 25, or from about 16 to about 25, or, e.g., independently 15, 16, 17, 18, 19, 20, 21, 22, 23, 24, or 25 nucleotides in each strand, wherein one of the strands is sufficiently complementary to a target region to mediate RNAi. In certain exemplary embodiments, the strands are aligned such that there are at least 4, 5, 6, 7, 8, 9, 10 or more bases at the end of one or both the strands do not align (i.e., for which no complementary bases occur in the opposing strand) such that an overhang of 4, 5, 6, 7, 8, 9, 10 or more residues occurs at one of or both ends of the duplex when strands are annealed.

Generally, siRNAs can be designed by using any method known in the art, for instance, by using the following protocol:

1. The siRNA should be specific for a target sequence. The first strand should be complementary to the target sequence, and the other strand is substantially complementary to the first strand. Exemplary target sequences are selected from the 5' untranslated region (5'-UTR) or an intronic region of a target gene, such as a target gene comprising a mutation. Cleavage of mRNA at these sites should eliminate translation of corresponding mutant protein. Target sequences from other regions of a target gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. In certain exemplary embodiments, the sense strand includes from about 13 to about 20, from about 13 to about 18, from about 13 to about 15, from about 15 to about 20, or from about 15 to about 18 nucleotides, e.g., 13, 14, 15, 16, 17, 18, 19, or 20 nucleotides. In certain embodiments, the sense strand includes about 19 to 25 nucleotides, e.g., 19, 20, 21, 22, 23, 24 or 25 nucleotides. In certain embodiments, the sense strand includes 19, 20 or 21 nucleotides. The skilled artisan will appreciate, however, that siRNAs having a length of less than 19 nucleotides, e.g., a length of 13, 14, 15, 16, 17 or 18 nucleotides, or greater than 25 nucleotides, can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. In certain exemplary embodiments, the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are particularly suitable. Accordingly, in an exemplary embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is particularly suitable. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). An exemplary, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). An exemplary non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the strands of the siRNA are paired in such a way as to have a 3' overhang of 4 to 15, e.g., 4, 5, 6 or 7 nucleotides. In certain embodiments, the antisense or guide strand of the siRNA is longer than the sense strand.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information web site.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)-(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNA should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant target mRNA), the siRNA may be incubated with target cDNA in a *Drosophila*-based in vitro mRNA expression system. Radiolabeled with $^{32}P$, newly synthesized target mRNAs are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Modified Nucleotides

In an embodiment, an oligonucleotide, e.g., an siRNA, comprises one or more chemically-modified nucleotides. In an embodiment, an oligonucleotide consists of chemically-modified nucleotides. In certain exemplary embodiments, >90%, >98%, >97%, >96, %>95%, >90%, >85%, >80%, >75%, >70%, >65%, >60%, >55% or >50% of the oligonucleotide comprises chemically-modified nucleotides. In certain exemplary embodiments, 100% of the oligonucleotide comprises chemically-modified nucleotides.

In an embodiment, the sense strand and the antisense strand of the siRNA each comprises one or more chemically-modified nucleotides. In an embodiment, each nucleotide of the sense strand and the antisense strand is chemically-modified. In an embodiment, the antisense strand comprises 2'-methoxy nucleotides and 2'-fluoro nucleotides. In an embodiment, the sense strand comprises 2'-methoxy nucleotides. In an embodiment, the nucleotides at positions 1 and 2 from the 5' end of the sense and antisense strands are connected to adjacent nucleotides via phosphorothioate linkages. In an embodiment, the nucleotides the 5' end and the 3' end are connected to adjacent nucleotides via phosphorothioate linkages.

Delivery and Distribution

In another aspect, provided herein is a method for selectively delivering a nucleic acid as described herein to a particular organ in a patient, comprising administering to the patient an oligonucleotide as described herein, such that the oligonucleotide is delivered selectively. In one embodiment, the organ is the liver. In another embodiment, the organ is a kidney. In another embodiment, the organ is the spleen. In another embodiment, the organ is the heart. In another embodiment, the organ is the brain. In another embodiment, the organ is the placenta.

The compositions described herein promote simple, efficient, non-toxic delivery of metabolically stabilized oligonucleotides, and promote potent silencing of therapeutic targets in a range of tissues in vivo.

In another aspect, provided herein is a method for selective in vivo delivery of a compound as described herein to a target organ, tissue or cells, comprising administering the compound to a subject.

In an embodiment, the method is at least 50%, at least 60%, at least 70%, at least 80%, at least 90% or at least 99% selective to the target organ, i.e., at least 50%, at least 60%, at least 70%, at least 80%, at least 90% or at least 99% of the oligonucleotide administered to a subject locates to the target organ.

In certain exemplary embodiments, the compound or pharmaceutical composition is administered by intravenous injection, intraperitoneal injection, intracranial injection, intrathecal injection, intrastriatal injection, or intracerebroventricular injection. In a particular embodiment, the compound or pharmaceutical composition is administered by intracerebroventricular injection.

Synthetic oligonucleotides can be delivered into cells by methods known in the art, including cationic liposome transfection and electroporation. To obtain longer term suppression of the target genes and to facilitate delivery under certain circumstances, one or more oligonucleotides can be expressed within cells from recombinant DNA constructs. Such methods for expressing oligonucleotide duplexes, e.g., siRNA duplexes, within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs, such as multiple regions of the gene encoding a target, targeting the same gene or multiple genes, and can be driven, for example, by separate PolIII promoter sites.

Viral-mediated delivery mechanisms can also be used to induce specific silencing of targeted genes through expression of oligonucleotides, for example, by generating recombinant adenoviruses harboring oligonucleotides under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the oligonucleotide results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of oligonucleotide containing solution into animal via the tail vein (Liu et al., 1999, supra; McCaffrey et al., 2002, supra; Lewis et al., 2002. Nanoparticles and liposomes can also be used to deliver oligonucleotides into animals. In certain exemplary embodiments, recombinant adeno-associated viruses (rAAVs) and their associated vectors can be used to deliver one or more siRNAs into cells, e.g., into neural cells (e.g., brain cells) (US Patent Applications 2014/0296486, 2010/0186103, 2008/0269149, 2006/0078542 and 2005/0220766).

In an embodiment, an oligonucleotide provided herein is a double-stranded RNA that comprises one or two or three non 2'-O-methyl-modified nucleotides and comprises an antisense strand that is at least 85% 2'-O-methyl modified. In a particular embodiment, the double-stranded RNA comprises 2'-methoxy-nucleotides and 2'-fluoro-nucleotides. In a particular embodiment, the double-stranded RNA comprises 2'-methoxy-nucleotides and 2'-deoxynucleotides. In a particular embodiment, the double-stranded RNA comprises 2'-methoxy-nucleotides and 2'-OH nucleotides. In a particular embodiment, the double-stranded RNA is fully chemically modified, comprising 2'-methoxy-nucleotides at every position except at positions 2 and 14, and optionally 20, from the 5' end of the antisense strand. In a particular embodiment, the double-stranded RNA is fully chemically modified, comprising, in the antisense strand, 2'-methoxy-nucleotides at every position except at positions 2, 14, and optionally 20 from the 5' end of the antisense strand, and in the sense strand 2'-methyoxy nucleotides at every position. In some cases, positions 2, and 14, and optionally 20, of the antisense strand are 2'-fluoro modified.

In an embodiment, an oligonucleotide provided herein is a double-stranded RNA that comprises one or more nucleotides connected to adjacent nucleotides via phosphorothioate linkages. In a particular embodiment, the nucleotides at positions 1 and 2 from the 5' end of the antisense strand are connected to adjacent nucleotides via phosphorothioate linkages. In a particular embodiment, the nucleotides at positions 1-7 from the 3' end of the antisense strand are connected to adjacent nucleotides via phosphorothioate linkages. In a particular embodiment, the nucleotides at positions 1-8 from the 3' end of the antisense strand are connected to adjacent nucleotides via phosphorothioate linkages. In a particular embodiment, the nucleotides at positions 1, 2 and 3 from the 5' end of the sense strand are connected to adjacent nucleotides via phosphorothioate linkages. In a particular embodiment, the nucleotides at positions 1, 2 and 3 from the 3' end of the sense strand are connected to adjacent nucleotides via phosphorothioate linkages. In a particular embodiment, the nucleotides at positions 1 and 2 from the 5' end of the sense strand are connected to adjacent nucleotides via phosphorothioate linkages. In a particular embodiment, the nucleotides at positions 1 and 2 from the 3' end of the sense strand are connected to adjacent nucleotides via phosphorothioate linkages.

In one embodiment of the double-stranded RNAs provided herein:

(1) the first oligonucleotide is fully chemically modified, comprising 2'-methoxy-nucleotides at every position except at positions 2 and 14, and optionally 20, from the 5' end of the antisense strand;

(2) the second oligonucleotide is fully chemically modified, comprising 2'-methoxy-nucleotides at every position of the sense strand;

(3) the nucleotides of the first oligonucleotide are connected to adjacent nucleotides via phosphodiester or phosphorothioate linkages, wherein the nucleotides at positions 1-2 from the 5' end, and/or at positions 1-8 from the 3' end are connected to adjacent nucleotides via phosphorothioate linkages; and (4) the nucleotides of the second oligonucleotide are connected to adjacent nucleotides via phosphodiester or phosphorothioate linkages, wherein the nucleotides at positions 1, 2 and 3 from the 3' end and/or at positions 1, 2 and 3 from the 3' end, are connected to adjacent nucleotides via phosphorothioate linkages.

In one embodiment of the double-stranded RNAs, the first oligonucleotide has 3-7 more ribonucleotides than the second oligonucleotide.

In one embodiment, the first oligonucleotide is the antisense strand and the second oligonucleotide is the sense strand.

Modified Oligonucleotides

In certain aspects of the invention, an RNA silencing agent (or any portion thereof), e.g., an siRNA, of the invention as described herein may be modified such that the activity of the RNA silencing agent is further improved. For example, the RNA silencing agents described above may be modified with any of the modifications described herein. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the oligonucleotides of the invention may be substituted with a destabilizing nucleotide to enhance single nucleotide target discrimination (see U.S. application Ser. No. 11/698,689, filed Jan. 25, 2007, U.S. Provisional Application No. 60/762,225 filed Jan. 25, 2006, and PCT/US19/46013, filed Aug. 9, 2019, each of which are incorporated herein by reference). Such a modification may be sufficient to abolish the specificity of the oligonucleotide for a non-target mRNA (e.g. wild-type mRNA), without appreciably affecting the specificity of the oligonucleotide for a target mRNA (e.g. gain-of-function mutant mRNA).

In certain exemplary embodiments, the oligonucleotides of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is particularly suitable because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly exemplary embodiments, the universal nucleotide is an inosine residue or a naturally occurring analog thereof.

In certain embodiments, the oligonucleotides of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In certain exemplary embodiments, the destabilizing nucleotide is introduced in the same strand or strand portion that contains the specificity-determining nucleotide.

In certain embodiments, the RNA silencing agents of the invention are modified by the introduction of at least one destabilizing nucleotide within 11 nucleotides from a specificity-determining nucleotide (e.g., within 11 nucleotides from the nucleotide which recognizes the disease-related polymorphism (e.g., a SNP position nucleotide)). For example, the destabilizing nucleotide may be introduced at a position that is within 11, 10, 9, 8, 7, 6, 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g., siRNAs and shRNAs), the destabilizing nucleotide may be introduced in the strand or strand portion that does not contain the specificity-determining nucleotide. In particular exemplary embodiments, the destabilizing nucleotide is introduced in the same strand or strand portion that contains the specificity-determining nucleotide.

In certain embodiments, the RNA silencing agents of the invention are modified by the introduction of a modified intersubunit linkage of Formula 1:

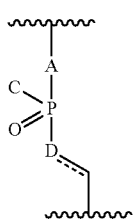

(1)

wherein:

D is selected from the group consisting of O, OCH$_2$, OCH, CH$_2$, and CH;

C is selected from the group consisting of O$^-$, OH, OR$^1$, NW, NH$_2$, S$^-$, and SH;

A is selected from the group consisting of O and CH$_2$;

R$^1$ is a protecting group;

═ is an optional double bond; and the intersubunit is bridging two optionally modified nucleosides.

In an embodiment, when C is O$^-$, either A or D is not O.

In an embodiment, D is CH$_2$.

In an embodiment, D is O.

In an embodiment, D is OCH$_2$.

In another embodiment, the modified intersubunit linkage of Formula VIII is a modified intersubunit linkage of Formula 2:

(2)

In another embodiment, the modified intersubunit linkage of Formula VIII is a modified intersubunit linkage of Formula 3:

(3)

In another embodiment, the modified intersubunit linkage of Formula VIII is a modified intersubunit linkage of Formula 4:

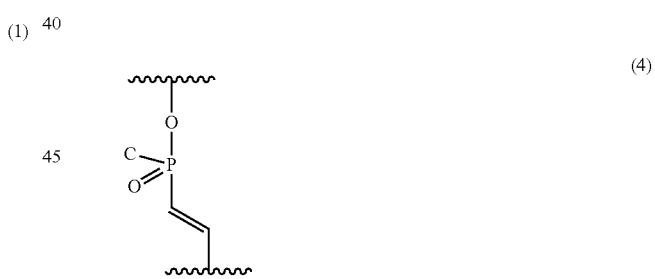

(4)

In another embodiment, the modified intersubunit linkage is a modified intersubunit linkage of Formula 5:

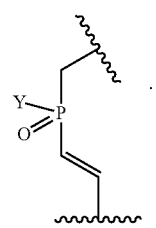

(5)

In another embodiment, the modified intersubunit linkage is a modified intersubunit linkage of Formula 6:

(6)

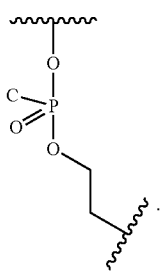

In another embodiment, the modified intersubunit linkage of Formula VII is a modified intersubunit linkage of Formula 7:

(7)

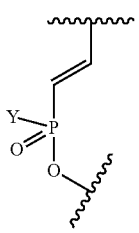

Figure 14:
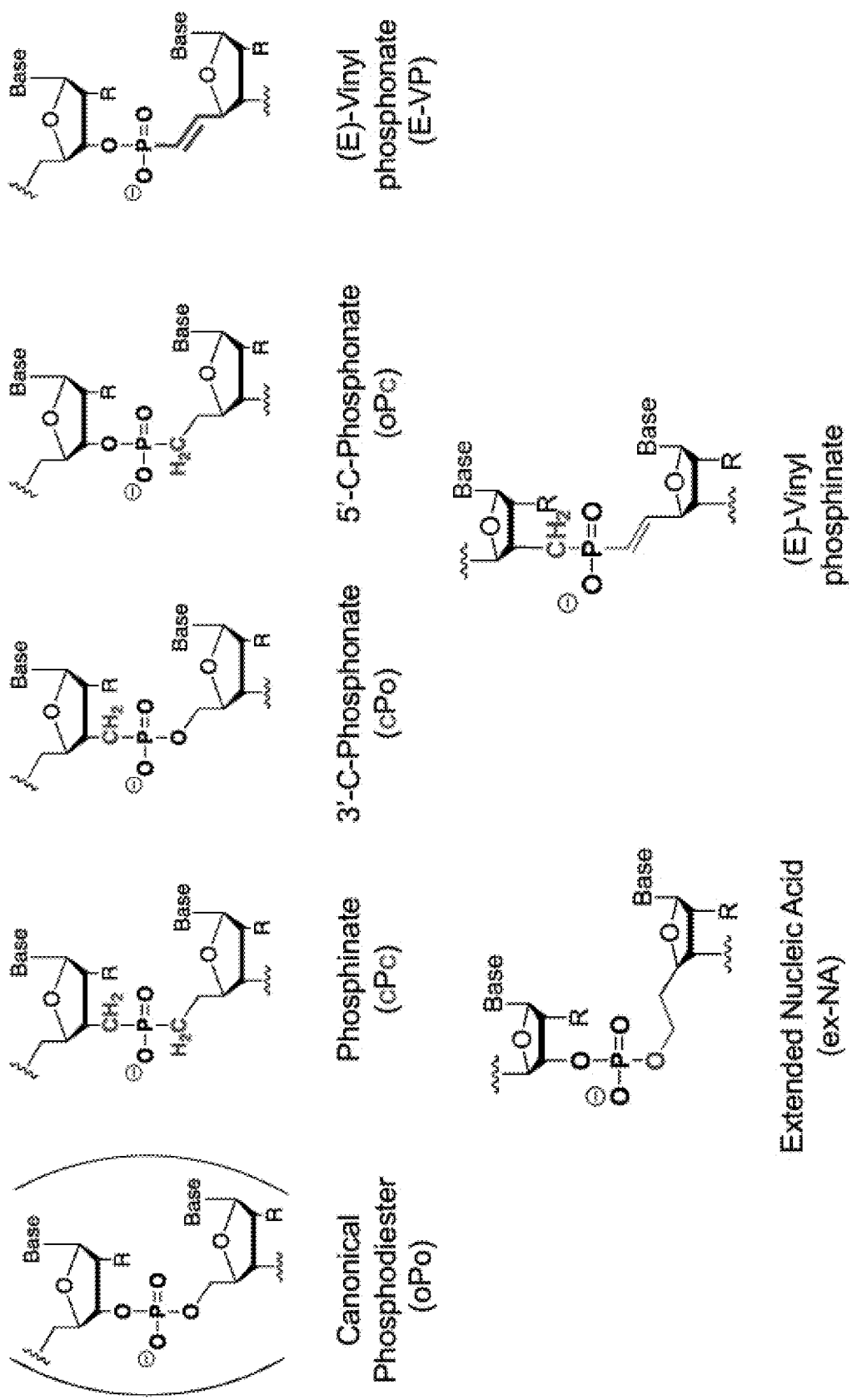
FIG. 14 illustrates example modified intersubunit linkers.

In certain embodiments, the RNA silencing agents of the invention are modified by the introduction of one or more of the intersubunit linkers of FIG. 14. In an exemplary embodiment, an intersubunit linker of FIG. 14 is inserted between the SNP position nucleotide and a nucleotide at a position directly adjacent to and on either side of the SNP position nucleotide of the antisense strand.

In certain embodiments, the RNA silencing agents of the invention are modified by the introduction of one or more vinyl phosphonate (VP) motifs in the intersubunit linker having the following formula:

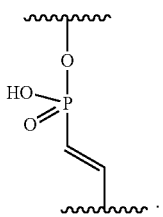

In certain embodiments, a VP motif is inserted at any position(s) of an oligonucleotide, e.g., an RNA. For example, for an oligonucleotide having a length of 20 nucleotides, a VP motif can be inserted at position 1-2, 2-3, 3-4, 4-5, 5-6, 6-7, 7-8, 8-9, 9-10, 10-11, 11-12, 12-13, 13-14, 14-15, 15-16, 16-17, 17-18, 18-19 or 19-20 and at any combinations of these.

In certain exemplary embodiments, a VP motif is inserted at one or more of positions 1-2, 5-6, 6-7, 10-11, 18-19 and/or 19-20 of the antisense strand.

In other exemplary embodiments, a VP motif is inserted at one or more of positions 1-2, 6-7, 10-11 and/or 19-20 of the antisense strand.

In an exemplary embodiment, a VP motif is inserted next to (i.e., between a SNP position nucleotide and a nucleotide at a position directly adjacent to and on either side of) the SNP position nucleotide of the antisense strand. In another exemplary embodiment, a VP motif is inserted next to (i.e., between a MM position nucleotide and a nucleotide at a position directly adjacent to and on either side of) the MM position nucleotide of the antisense strand.

2) Modifications to Enhance Efficacy and Specificity

In certain embodiments, the siRNAs of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., an siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. In particular embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an siRNA of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In certain exemplary embodiments, the mismatched base pair is selected from the group consisting of G:A, C:A, C:U, G:G, A:A, C:C and U:U. In other embodiments, the asymmetry of an siRNA of the invention may be enhanced such that there is at least one wobble base pair, e.g., G:U, between the 5' end of the first or antisense strand and the 3' end of the sense strand portion. In other embodiments, the asymmetry of an RNA silencing agent of the invention may be enhanced such that there is at least one base pair comprising a rare nucleotide, e.g., inosine (I). In certain exemplary embodiments, the base pair is selected from the group consisting of an I:A, I:U and I:C. In yet another embodiment, the asymmetry of an siRNA of the invention may be enhanced such that there is at least one base pair comprising a modified nucleotide. In certain exemplary embodiments, the modified nucleotide is selected from the group consisting of 2-amino-G, 2-amino-A, 2,6-diamino-G, and 2,6-diamino-A.

In certain embodiments, the RNA silencing agents of the invention are altered at one or more intersubunit linkages in an oligonucleotide by the introduction of a VP motif having the following formula:

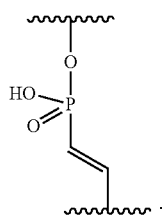

3) RNA Silencing Agents with Enhanced Stability

The RNA silencing agents (e.g., siRNAs) described herein can be further modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In an exemplary aspect, the invention features RNA silencing agents (e.g., siRNAs) that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In an exemplary embodiment of the present invention, the RNA silencing agents (e.g., siRNAs) may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the RNA silencing agent (e.g., siRNA). Particularly, the ends may be stabilized by incorporating modified nucleotide analogues.

In certain embodiments, the RNA silencing agents of the invention are altered at one or more intersubunit linkages in an oligonucleotide by the introduction of a VP motif having the following formula:

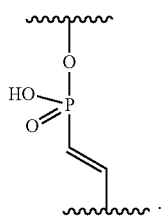

A variety of oligonucleotide types (e.g., gapmers, mixmers, miRNA inhibitors, splice-switching oligonucleotides ("SSOs"), phosphorodiamidate morpholino oligonucleotides ("PMOs"), peptide nucleic acids ("PNAs") and the like) can be used in the oligonucleotides described herein, optionally utilizing various combinations of modifications (e.g., chemical modifications) and/or conjugations described herein and in, e.g., U.S. Ser. No. 15/089,423; U.S. Ser. No. 15/236,051; U.S. Ser. No. 15/419,593; U.S. Ser. No. 15/697, 120 and U.S. Pat. No. 9,809,817; and U.S. Ser. No. 15/814, 350 and U.S. Pat. No. 9,862,350, each of which is incorporated herein by reference in its entirety for all purposes.

Figure 2:
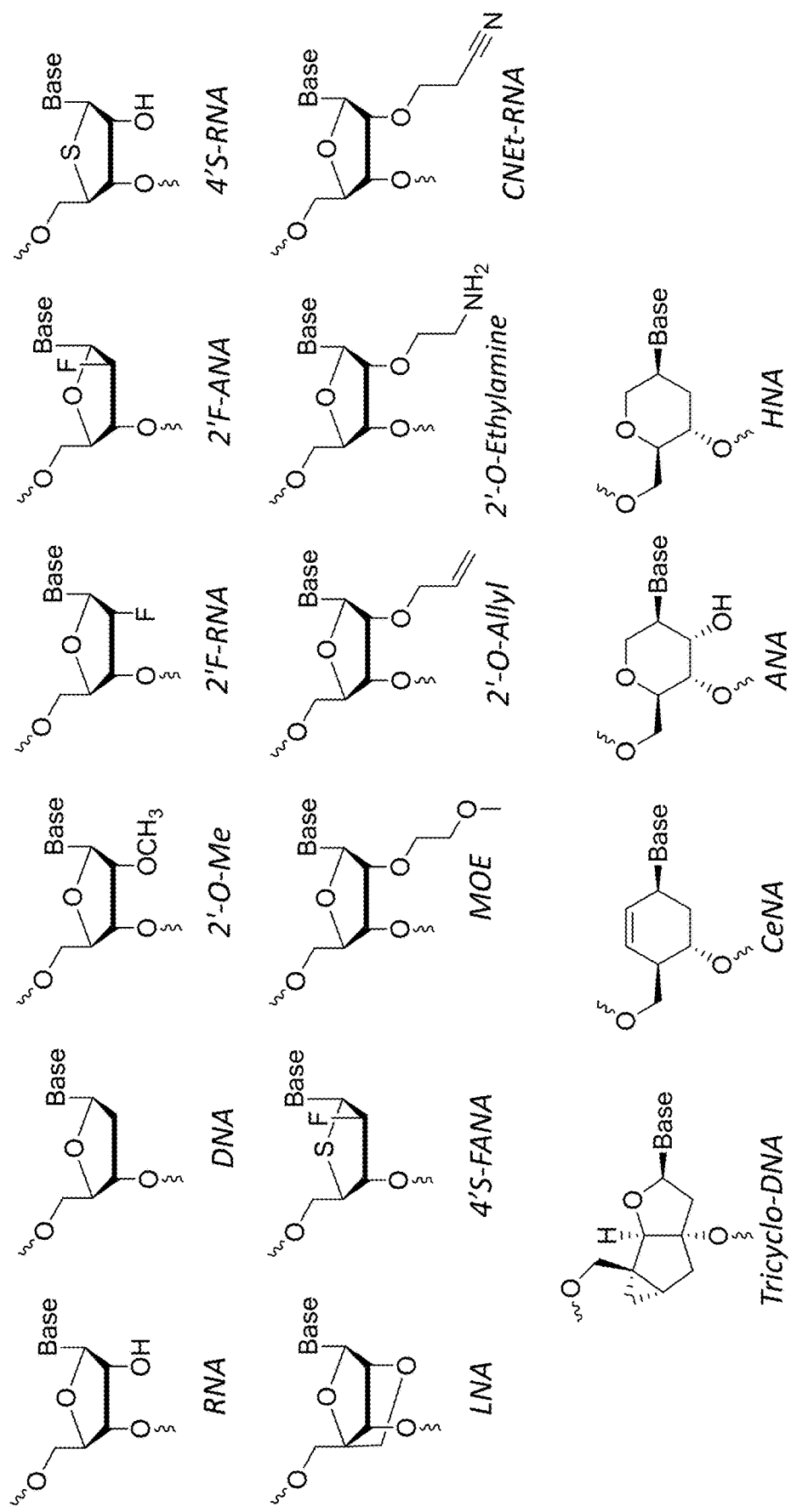
FIG. 2 depicts sugar modifications according to certain exemplary embodiments.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphodiester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I. Examples of suitable sugar modifications according to certain exemplary embodiments are shown at FIG. 2.

In particular embodiments, the modifications are 2'-fluoro, 2'-amino and/or 2'-thio modifications. Particular exemplary modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluorocytidine, and 5-fluoro-uridine. 2'-deoxy-nucleotides and 2'-Ome nucleotides can also be used within modified RNA-silencing agents of the instant invention. Additional modified residues include, deoxy-abasic, inosine, N3-methyl-uridine, N6, N6-dimethyl-adenosine, pseudouridine, purine ribonucleoside and ribavirin. In certain exemplary embodiments, the 2' moiety is a methyl group such that the linking moiety is a 2'-O-methyl oligonucleotide.

In an exemplary embodiment, an RNA silencing agent described herein comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2''-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agents described herein comprise Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also exemplified are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2'-OMe moiety on a U in a sense or antisense strand, but especially on a sense strand, or provision of a 2'-OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (in particular embodiments sequence changes are located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2'-OMe moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents (e.g., siRNAs) described herein may be modified with chemical moieties, for example, to enhance cellular uptake by target cells (e.g., neuronal cells). Thus, the invention includes siRNAs which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, a modification to the RNA silencing agents of the invention comprise a VP motif in one or more intersubunit linkers of an oligonucleotide, wherein the VP motif has the following formula:

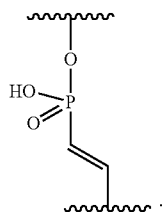

In a particular embodiment, an siRNA is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin D, DHA, DHAg2 (PC DHA), DCA, DCAg2 (PC DCA), EPA, vitamin E, vitamin K, vitamin A, folic acid, or a cationic dye (e.g., Cy3).

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. In certain exemplary embodiments, these are located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., 0-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, typically covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon.

In one aspect, the ligand is a lipid or lipid-based molecule. Such a lipid or lipid-based molecule typically binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. In a particular embodiment, the lipid based ligand binds HSA. However, it is desired that the affinity not be so strong that the HSA-ligand binding cannot be reversed. In another exemplary embodiment, the lipid based ligand binds HSA weakly or not at all.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, typically a helical cell-permeation agent. In certain exemplary embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an alpha-helical agent, which typically has a lipophilic face and a lipophobic face.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

6) Hydrophobic Moieties

In certain embodiments of the RNA silencing agents (e.g., siRNAs) provided herein, the RNA silencing agent is conjugated to one or more hydrophobic moieties (see PCT Pub. No. WO 2018/031933, which is incorporated herein by reference). In an embodiment, the hydrophobic moiety has an affinity for low density lipoprotein and/or intermediate density lipoprotein. In a related embodiment, the hydrophobic moiety is a saturated or unsaturated moiety having fewer than three double bonds.

In another embodiment, the hydrophobic moiety has an affinity for high density lipoprotein. In a related embodiment, the hydrophobic moiety is a polyunsaturated moiety having at three or more double bonds (e.g., having three, four, five, six, seven, eight, nine or ten double bonds). In a particular embodiment, the hydrophobic moiety is a polyunsaturated moiety having three double bonds. In a particular embodiment, the hydrophobic moiety is a polyunsaturated moiety having four double bonds. In a particular embodiment, the hydrophobic moiety is a polyunsaturated moiety having five double bonds. In a particular embodiment, the hydrophobic moiety is a polyunsaturated moiety having six double bonds.

In another embodiment, the hydrophobic moiety is selected from the group consisting of fatty acids, steroids, secosteroids, lipids, gangliosides and nucleoside analogs, and endocannabinoids.

In another embodiment, the hydrophobic moiety is a neuromodulatory lipid, e.g., an endocannabinoid. Non-limiting examples of endocannabinoids include: anandamide, arachidonoylethanolamine, 2-Arachidonyl glyceryl ether (noladin ether), 2-Arachidonyl glyceryl ether (noladin ether), 2-Arachidonoylglycerol, and N-Arachidonoyl dopamine.

In another embodiment, the hydrophobic moiety is an omega-3 fatty acid. Non-limiting examples of omega-3 fatty acids include, but are not limited to: hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, Timnodonic acid), heneicosapentaenoic acid (HPA), docosapentaenoic acid (DPA, clupanodonic acid), docosahexaenoic acid (DHA, cervonic acid), tetracosapentaenoic acid, and tetracosahexaenoic acid (nisinic acid).

In another embodiment, the hydrophobic moiety is an omega-6 fatty acid. Non-limiting examples of omega-6 fatty acids include, but are not limited to: linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (osbond acid), tetracosatetraenoic acid, and tetracosapentaenoic acid.

In another embodiment, the hydrophobic moiety is an omega-9 fatty acid. Non-limiting examples of omega-9 fatty acids include, but are not limited to: oleic acid, eicosenoic acid, Mead acid, erucic acid, and nervonic acid.

In another embodiment, the hydrophobic moiety is a conjugated linolenic acid. Non-limiting examples of conjugated linolenic acids include, but are not limited to: α-calendic acid, β-calendic acid, jacaric acid, α-eleostearic acid, β-eleostearic acid, catalpic acid, and punicic acid.

In another embodiment, the hydrophobic moiety is a saturated fatty acid. Non-limiting examples of saturated fatty acids include, but are not limited to: caprylic acid, capric acid, docosanoic acid, lauric acid, myristic acid, palmitic acid, stearic acid, arachidic acid, behenic acid, lignoceric acid, and cerotic acid.

In another embodiment, the hydrophobic moiety is an acid selected from the group consisting of: rumelenic acid, α-parinaric acid, β-parinaric acid, bosseopentaenoic acid, pinolenic acid, and podocarpic acid.

In another embodiment, the hydrophobic moiety is selected from the group consisting of: docosanoic acid (DCA), docosahexaenoic acid (DHA), and eicosapentaenoic acid (EPA). In a particular embodiment, the hydrophobic moiety is docosanoic acid (DCA). In another particular embodiment, the hydrophobic moiety is DHA. In another particular embodiment, the hydrophobic moiety is EPA.

In another embodiment, the hydrophobic moiety is a secosteroid. In a particular embodiment, the hydrophobic moiety is calciferol. In another embodiment, the hydrophobic moiety is a steroid other than cholesterol.

In a particular embodiment, the hydrophobic moiety is not cholesterol.

In another embodiment, the hydrophobic moiety is an alkyl chain, a vitamin, a peptide, or a bioactive conjugate, including but not limited to: glycosphingolipids, polyunsaturated fatty acids, secosteroids, steroid hormones, or sterol lipids.

In an embodiment, an oligonucleotide provided herein is a double-stranded RNA that comprises one or more chemically-modified nucleotides. In a particular embodiment, the double-stranded RNA comprises 2'-methoxy-nucleotides and 2'-fluoro-nucleotides. In a particular embodiment, the double-stranded RNA comprises 2'-methoxy-nucleotides and 2'-deoxynucleotides. In a particular embodiment, the double-stranded RNA comprises 2'-methoxy-nucleotides and 2'-riboses. In a particular embodiment, the double-stranded RNA is fully chemically modified, comprising 2'-methoxy-nucleotides at every position except at positions 2 and 14 from the 5' end of the antisense strand.

In an embodiment, an oligonucleotide provided herein is a double-stranded RNA that comprises one or more nucleotides connected to adjacent nucleotides via phosphorothioate linkages. In a particular embodiment, the nucleotides at positions 1 and 2 from the 5' end of the antisense strand are connected to adjacent nucleotides via phosphorothioate linkages. In a particular embodiment, the nucleotides at positions 1-8 from the 3' end of the antisense strand are connected to adjacent nucleotides via phosphorothioate linkages. In a particular embodiment, the nucleotides at positions 1, 2 and 3 from the 5' end of the sense strand are connected to adjacent nucleotides via phosphorothioate linkages. In a particular embodiment, the nucleotides at positions 1, 2 and 3 from the 3' end of the sense strand are connected to adjacent nucleotides via phosphorothioate linkages.

In one embodiment of the double-stranded RNAs provided herein:

(1) the first oligonucleotide is fully chemically modified, comprising 2'-methoxy-nucleotides at every position except at positions 2 and 14 from the 5' end of the antisense strand;

(2) is fully chemically modified, comprising 2'-methoxy-nucleotides at every position;

(3) the nucleotides of the first oligonucleotide are connected to adjacent nucleotides via phosphodiester or phosphorothioate linkages, wherein the nucleotides at positions 1-2 from the 5' end, and/or at positions 1-8 from the 3' end are connected to adjacent nucleotides via phosphorothioate linkages; and (4) the nucleotides of the second oligonucleotide are connected to adjacent nucleotides via phosphodiester or phosphorothioate linkages, wherein the nucleotides at positions 1, 2 and 3 from the 3' end and/or at positions 1, 2 and 3 from the 3' end, are connected to adjacent nucleotides via phosphorothioate linkages.

In one embodiment of the double-stranded RNAs, the first oligonucleotide has 3-7 more ribonucleotides than the second oligonucleotide.

In one embodiment, the first oligonucleotide is the antisense strand and the second oligonucleotide is the sense strand.

7) Branched Oligonucleotides

Figure 15:
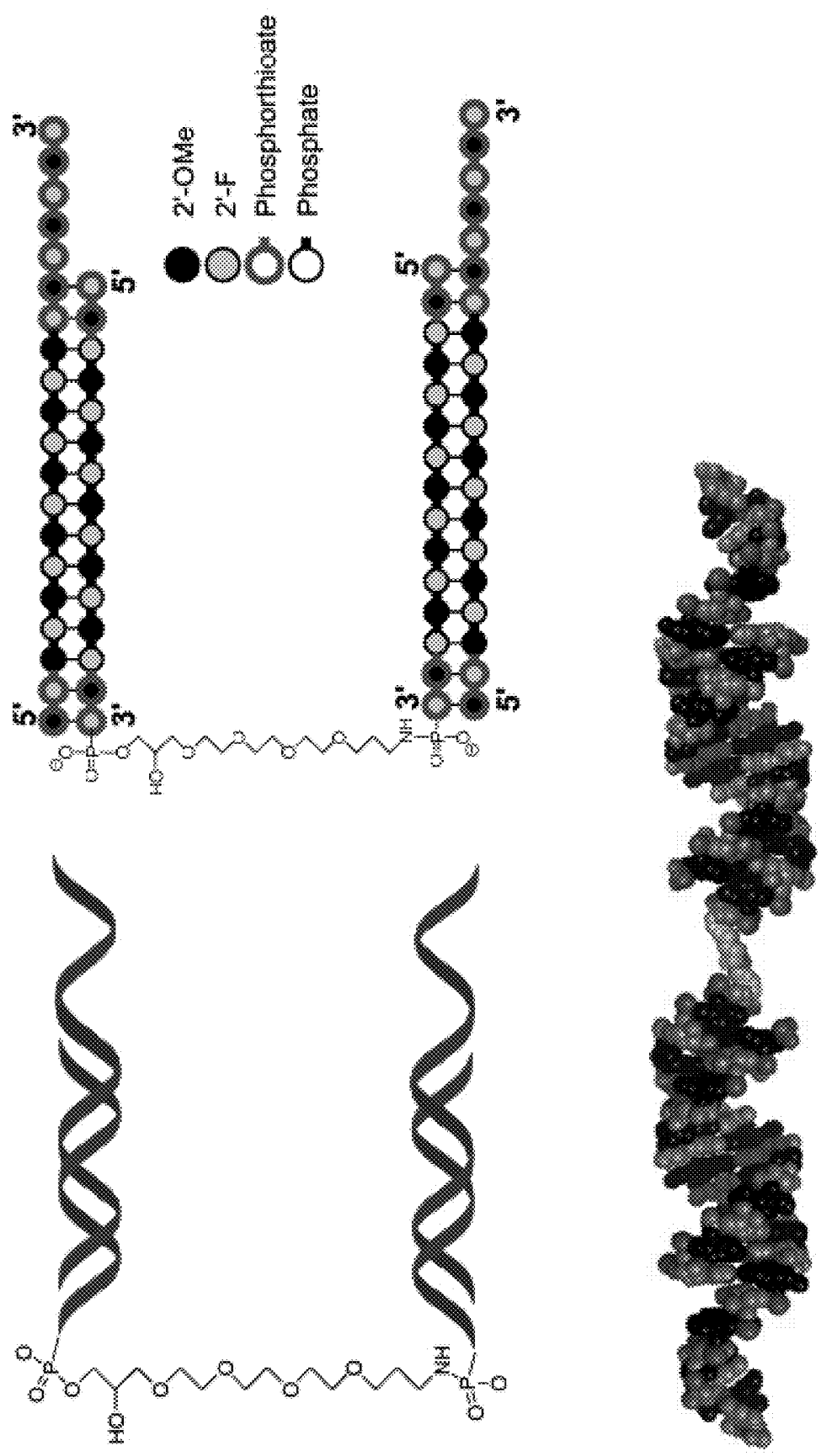
FIG. 15 illustrates an example di-branched siRNA chemical scaffold.
Figure 16:
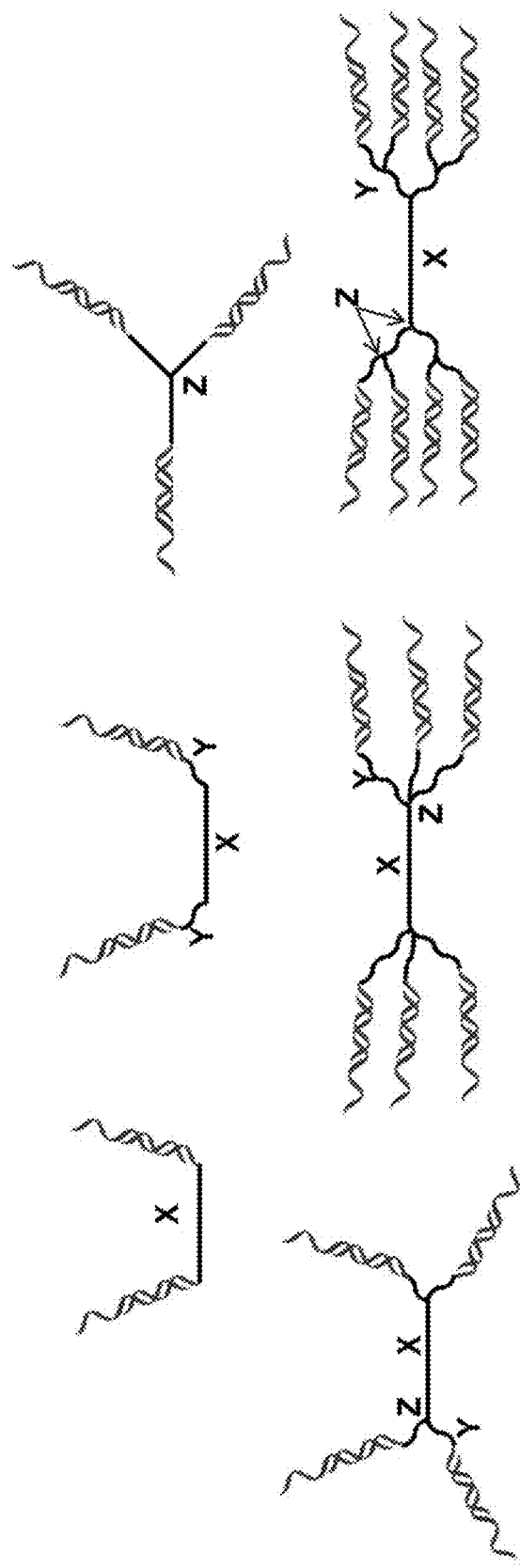
FIG. 16 shows oligonucleotide branching motifs according to certain exemplary embodiments. The double-helices represent oligonucleotides. The combination of different linkers, spacer(s) and branching points allows generation of a wide diversity of branched hsiRNA structures.

Two or more RNA silencing agents as disclosed above, for example oligonucleotide constructs such as siRNAs, may be connected to one another by one or more moieties independently selected from a linker, a spacer and a branching point, thereby forming a branched oligonucleotide containing two or more RNA silencing agents. FIG. 15 illustrates an exemplary di-siRNA di-branched scaffolding for delivering two siRNAs. In representative embodiments, the nucleic acids of the branched oligonucleotide each comprise an antisense strand (or portions thereof), wherein the antisense strand has sufficient complementary to a heterozygous single nucleotide polymorphism to mediate an RNA-mediated silencing mechanism (e.g. RNAi). In other embodiments, there is provided a second type of branched oligonucleotides featuring nucleic acids that comprise a sense strand (or portions thereof) for silencing antisense transcripts, where the sense strand has sufficient complementarity to an antisense transcript to mediate an RNA-mediated silencing mechanism. In further embodiments, there is provided a third type of branched oligonucleotides including nucleic acids of both types, that is, a nucleic acid comprising an antisense strand (or portions thereof) and an oligonucleotide comprising a sense strand (or portions thereof).

In exemplary embodiments, the branched oligonucleotides may have two to eight RNA silencing agents attached through a linker. The linker may be hydrophobic. In a particular embodiment, branched oligonucleotides of the present application have two to three oligonucleotides. In one embodiment, the oligonucleotides independently have substantial chemical stabilization (e.g., at least 40% of the constituent bases are chemically-modified). In a particular embodiment, the oligonucleotides have full chemical stabilization (i.e., all of the constituent bases are chemically-modified). In some embodiments, branched oligonucleotides comprise one or more single-stranded phosphorothioated tails, each independently having two to twenty nucleotides. In a particular embodiment, each single-stranded tail has eight to ten nucleotides.

In certain embodiments, branched oligonucleotides are characterized by three properties: (1) a branched structure, (2) full metabolic stabilization, and (3) the presence of a single-stranded tail comprising phosphorothioate linkers. In a specific embodiment, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Branched oligonucleotides are provided in various structurally diverse embodiments. As shown in FIG. 36, for example, in some embodiments nucleic acids attached at the branching points are single stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature (Tm~37° C.) for fast dissociation upon internalization of the branched structure into the cell.

Figure 17:
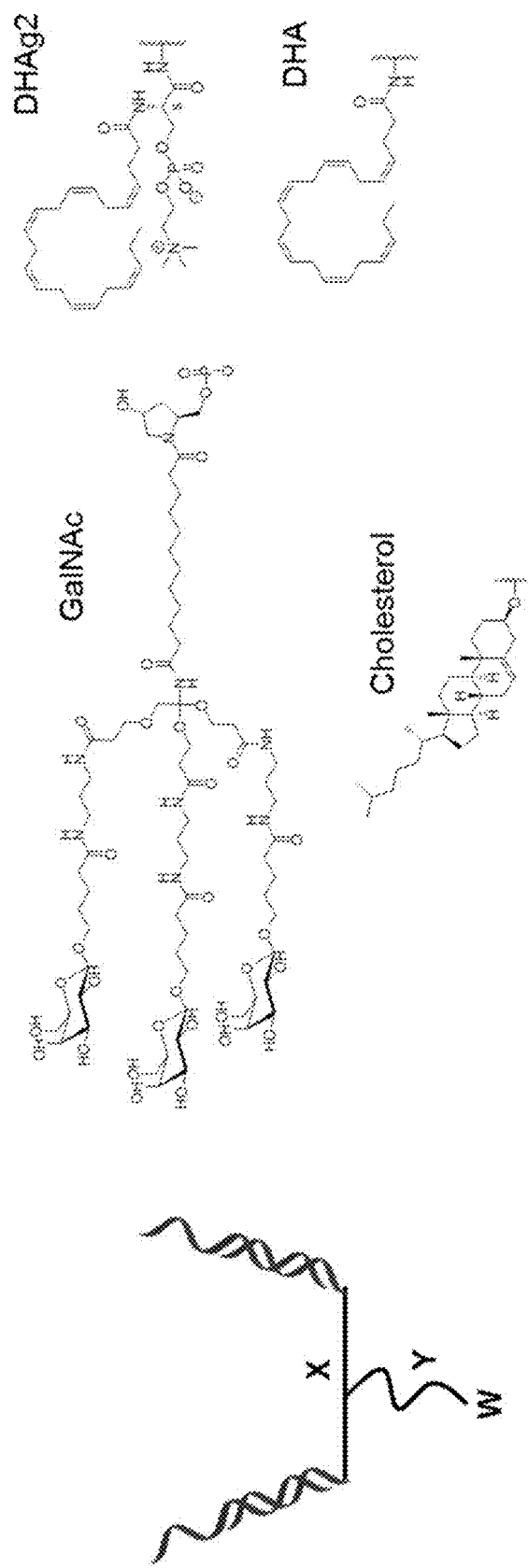
FIG. 17 shows branched oligonucleotides of the invention with conjugated bioactive moieties.

As shown in FIG. 17, Di-siRNA branched oligonucleotides may comprise chemically diverse conjugates. Conjugated bioactive ligands may be used to enhance cellular specificity and to promote membrane association, internalization, and serum protein binding. Examples of bioactive moieties to be used for conjugation include DHAg2, DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, or combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole. In another embodiment, each linker is a structure selected from the formulas of FIG. 17.

In another aspect, provided herein is a branched oligonucleotide compound of formula (I):

L-(N)$_n$     (I)

wherein L is selected from an ethylene glycol chain, an alkyl chain, a peptide, RNA, DNA, a phosphate, a phosphonate, a phosphoramidate, an ester, an amide, a triazole, or combinations thereof, wherein formula (I) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, or combinations thereof; N is an RNA duplex comprising a sense strand and an antisense strand, wherein the antisense strand comprises a region of complementarity which is substantially complementary to a region of a gene comprising an allelic polymorphism, wherein the antisense strand comprises: a single nucleotide polymorphism (SNP) position nucleotide at a position 2 to 7 from the 5' end that is complementary to the allelic polymorphism; and a mismatch (MM) position nucleotide located 2-11 nucleotides from the SNP position nucleotide that is a mismatch with a nucleotide in the gene. In exemplary embodiments, the SNP position nucleotide is at a position 2, 4 or 6 from the 5' end and the mismatch (MM) position nucleotide is located 2-6 nucleotides from the SNP position nucleotide.

The sense strand and antisense strand each independently comprise one or more chemical modifications; and n is 2, 3, 4, 5, 6, 7 or 8.

In an embodiment, the compound of formula (I) has a structure selected from formulas (I-1)-(I-9) of Table 1.

TABLE 1

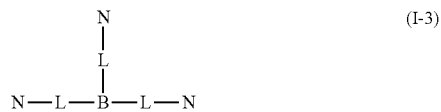

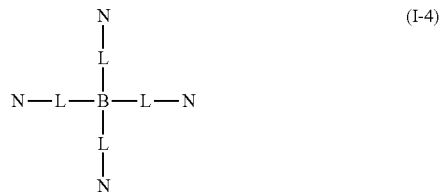

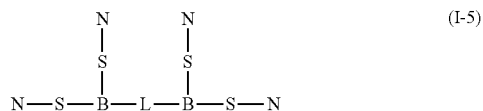

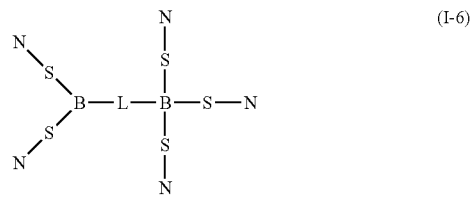

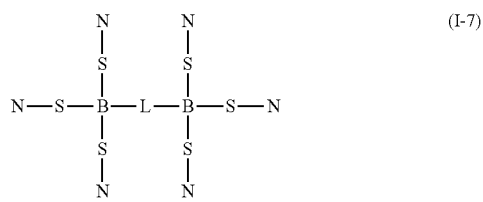

TABLE 1-continued

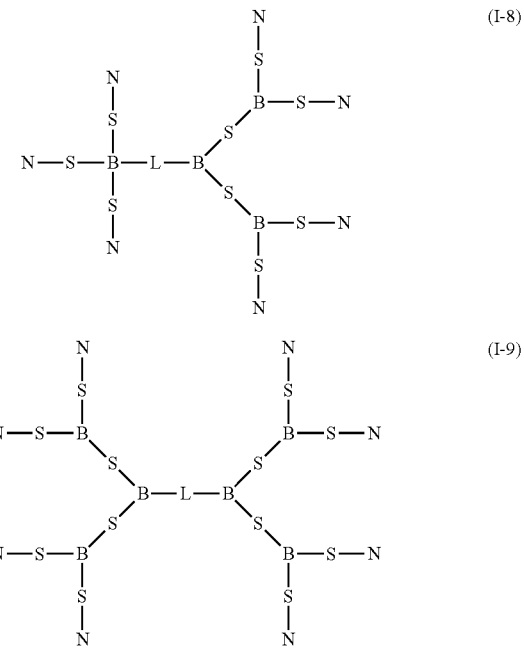

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, or combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole. In another embodiment of the compound of formula (I), each linker is a structure selected from the formulas of FIG. 36.

Figure 18:
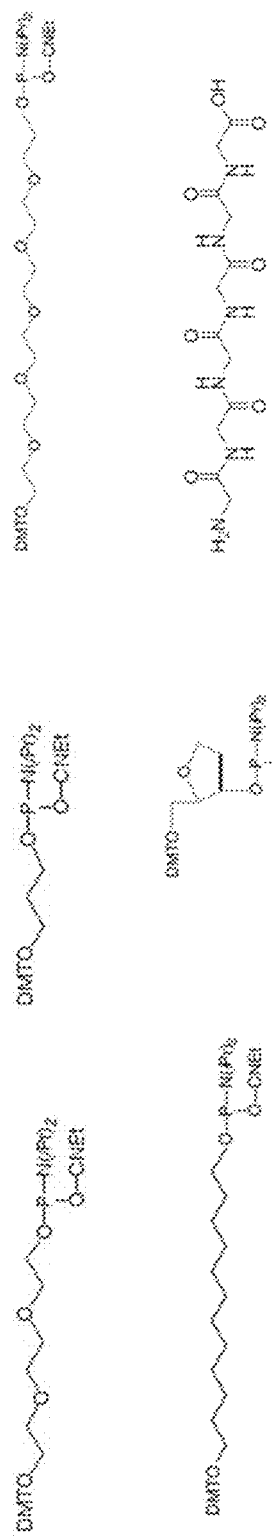
FIG. 18 shows exemplary amidite linkers, spacers and branching moieties.
Figure 18:
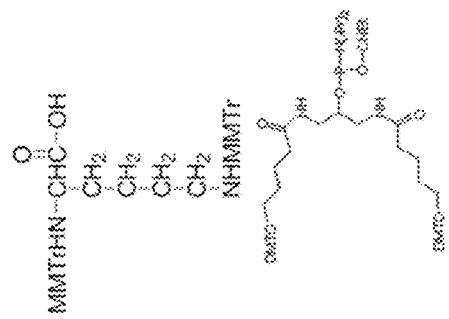
Figure 18:
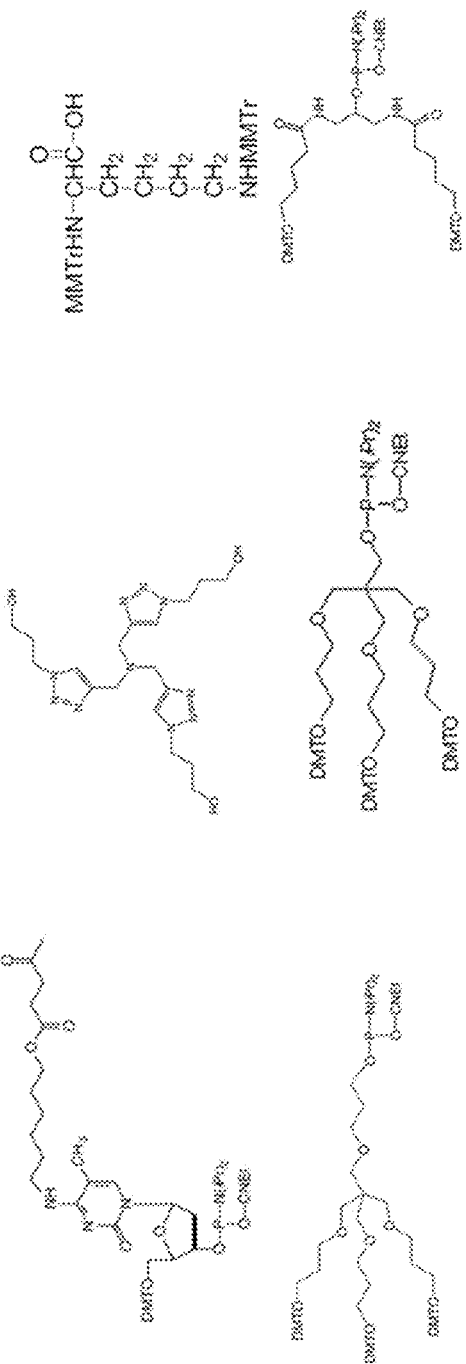

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of FIG. 18.

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In certain embodiments of the compound of formula (I), at least one oligonucleotide (e.g., antisense strand) is fully stabilized or nearly fully stabilized. In certain embodiments of the compound of formula (I), at least one oligonucleotide (e.g., antisense strand) is fully stabilized or nearly fully stabilized. In certain embodiments of the compound of formula (I), at least one oligonucleotide (e.g., antisense strand) comprises at least 85% 2'-O-methyl. In certain embodiments of the compound of formula (I), each nucleic acid comprises at least 85% 2'-O-methyl. In certain embodiments of the compound of formula (I), each nucleic acid comprises at least 90% 2'-O-methyl. In certain embodiments of the compound of formula (I), each nucleic acid comprises at least 85% 2'-O-methyl, wherein at least one, or each, antisense strand comprises a non-2'-O-methyl at positions 2 and 14, and optionally 20, from the 5' end of the antisense strand. In certain embodiments of the compound of formula (I), each nucleic acid comprises at least 85%, 90%, or 95% 2'-O-methyl, wherein at least one, or each, antisense strand comprises a non-2'-O-methyl at positions 2 and 14, and optionally 20, from the 5' end of the antisense strand, and the sense strand is fully 2'-O-methyl modified.

In an embodiment, each antisense strand independently comprises a 5' terminal group R selected from the groups of Table 2:

TABLE 2
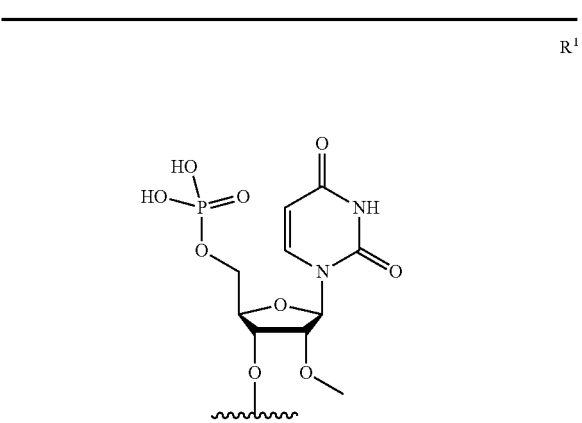
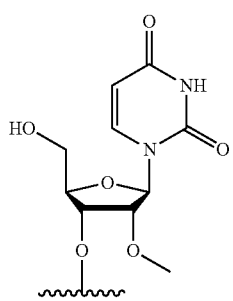
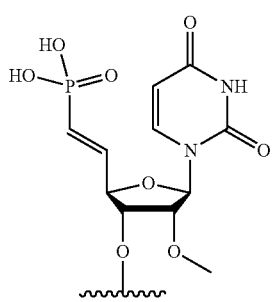
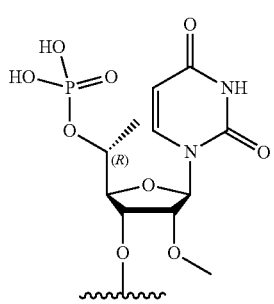
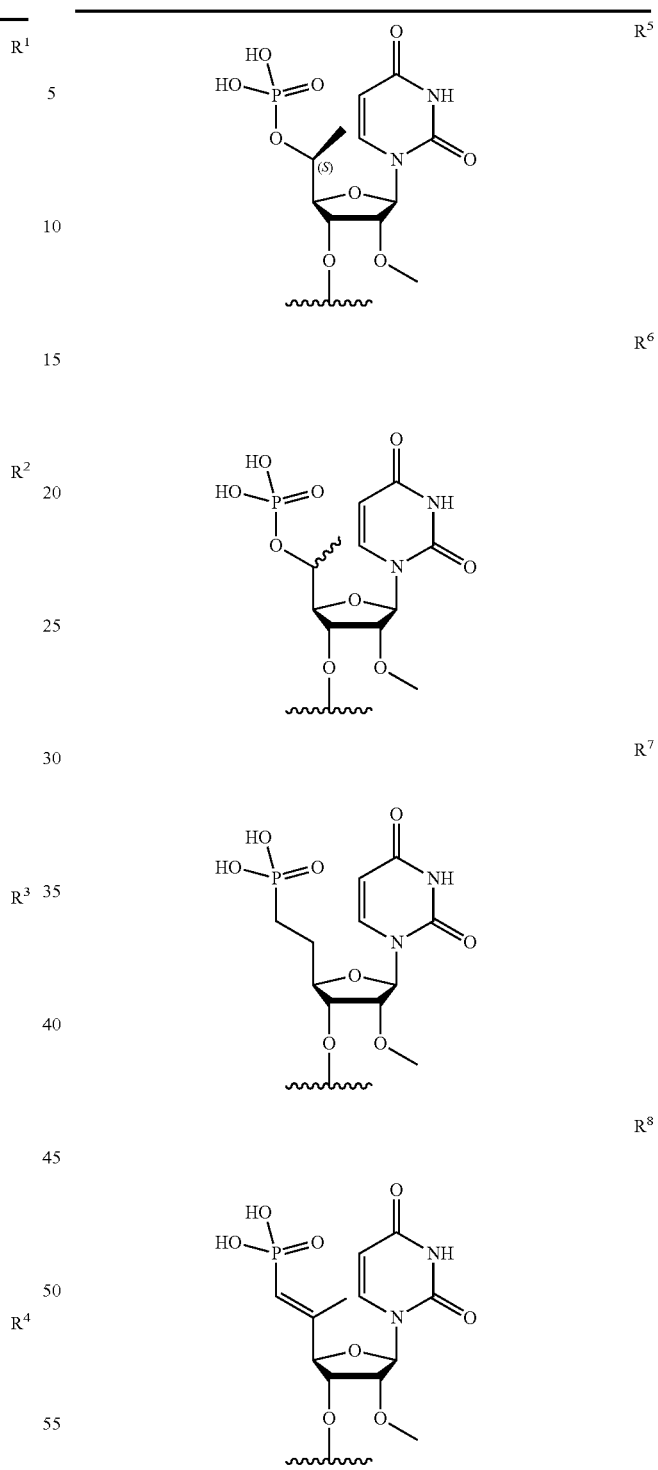
In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.
Structure of Formula (II)
In an embodiment, the compound of formula (I) the structure of formula (II):

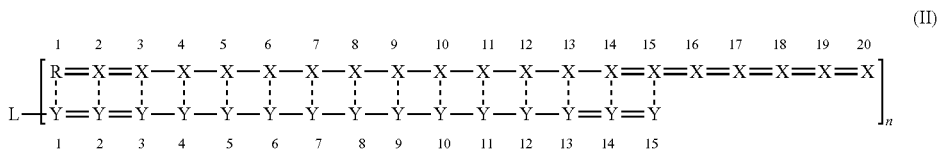
(II)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; ═ represents a phosphorothioate internucleoside linkage; and --- represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, 100%, >95%, >90%, or >85% of X's of the structure of formula (II) are chemically-modified nucleotides.

Structure of Formula (III)

In an embodiment, the compound of formula (I) has the structure of formula (III):

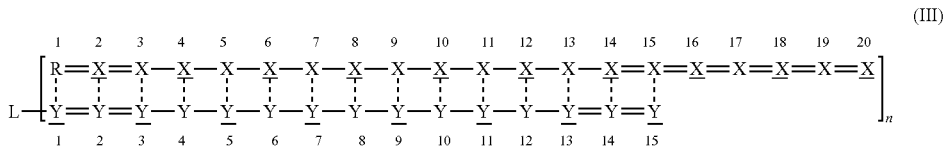
(III)

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

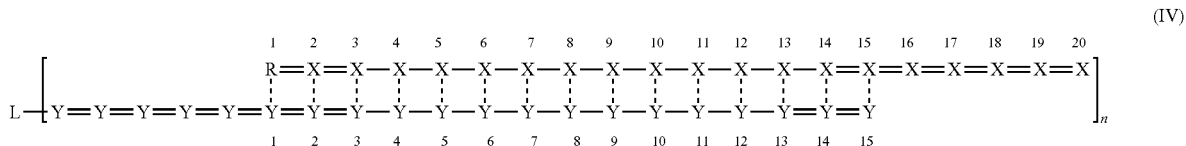
(IV)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; ═ represents a phosphorothioate internucleoside linkage; and --- represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches.

In certain embodiments, 100%, >95%, >90%, or >85% of X's of the structure of formula (IV) are chemically-modified nucleotides.

Structure of Formula (V)

In an embodiment, the compound of formula (I) has the structure of formula (V):

$$L-\left[\begin{array}{c} \underset{1}{R}=\underset{2}{\underline{X}}=\underset{3}{X}-\underset{4}{\underline{X}}-\underset{5}{X}-\underset{6}{\underline{X}}-\underset{7}{X}-\underset{8}{\underline{X}}-\underset{9}{X}-\underset{10}{\underline{X}}-\underset{11}{X}-\underset{12}{\underline{X}}-\underset{13}{\underline{X}}=\underset{14}{X}=\underset{15}{\underline{X}}=\underset{16}{X}=\underset{17}{\underline{X}}=\underset{18}{X}=\underset{19}{\underline{X}}=\underset{20}{X} \\ Y=\underline{Y}=Y=\underline{Y}=Y=\underline{Y}=\underline{Y}=\underline{Y}-Y-\underline{Y}-Y-\underline{Y}-Y-\underline{Y}-Y-\underline{Y}-Y-\underline{Y}=Y=\underline{Y} \\ {1\ \ 2\ \ 3\ \ 4\ \ 5\ \ 6\ \ 7\ \ 8\ \ 9\ \ 10\ \ 11\ \ 12\ \ 13\ \ 14\ \ 15} \end{array}\right]_n \quad (V)$$

wherein $\underline{X}$, for each occurrence, independently, is a nucleotide comprising a 2'-deoxy-2'-fluoro modification; X, for each occurrence, independently, is a nucleotide comprising a 2'-O-methyl modification; $\underline{Y}$, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In an embodiment, the compound of formula (I) has the structure of Formula (Va): which is a L-[siRNA]n, wherein the siRNA comprises an siRNA having any one or more of patterns 1A-F, as described herein. In certain embodiments, each siRNA of Formula (Va) is identical. In certain embodiments, each siRNA of Formula (Va) is not identical.

Variable Linkers

In an embodiment of the compound of formula (I), L has the structure of L1:

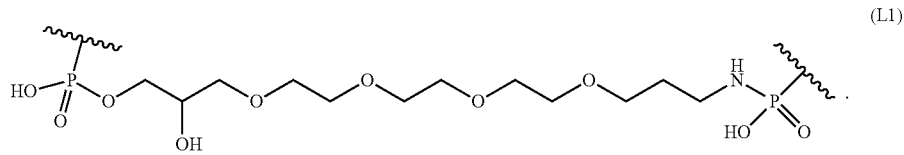 [SMILES: *P(=O)(O)NCCCOCCOCCOCCOCC(O)COP(*)(=O)O]

(L1)

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V) or (Va), L has the structure of L1. In an embodiment of the structure of formula (VI), L has the structure of L1. In an embodiment of the structure of formula (VI), L has the structure of L1.

In an embodiment of the compound of formula (I), L has the structure of L2:

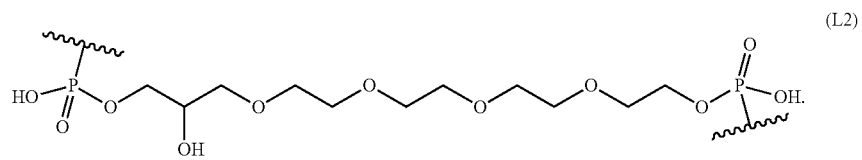 [SMILES: *P(=O)(O)OCCOCCOCCOCCOCC(O)COP(*)(=O)O]

(L2)

In an embodiment of L2, R is $R^3$ and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V) or (Va), L has the structure of L2. In an embodiment of the structure of formula (VI), L has the structure of L2. In an embodiment of the structure of formula (VI), L has the structure of L2.

10) Delivery System

In a further aspect, provided herein is a delivery system for therapeutic nucleic acids having the structure of formula (VI):

$$L\text{-}(cNA)_n \qquad (VI)$$

wherein L is selected from an ethylene glycol chain, an alkyl chain, a peptide, RNA, DNA, a phosphate, a phosphonate, a phosphoramidate, an ester, an amide, a triazole, or combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, or combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides. In certain embodiments, each cNA is fully, or nearly fully, chemically modified at the 2' position and at least 85% 2'-O-methyl modified.

In an embodiment, the compound of formula (VI) has a structure selected from formulas (VI-1)-(VI-9) of Table 3:

TABLE 3

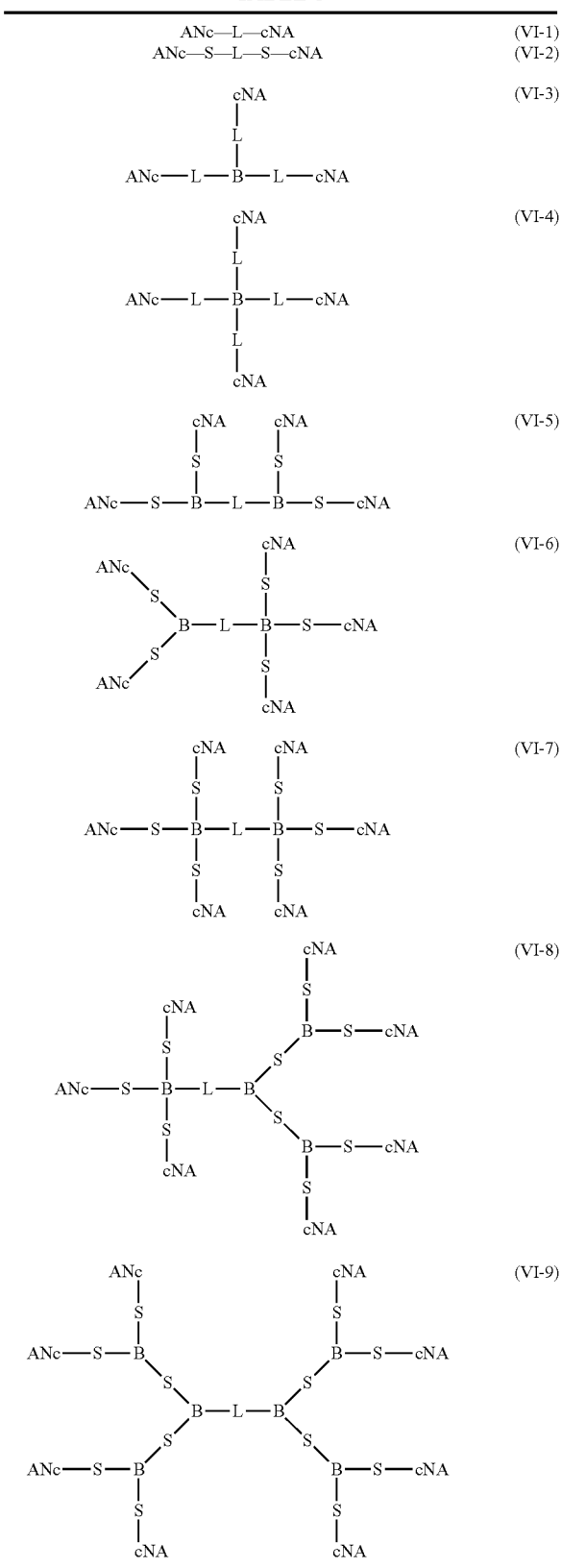

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9).

In an embodiment, the compound of formulas (VI) (including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a region of complementarity which is substantially complementary to a region of a target gene. Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 16 contiguous nucleotides. In an embodiment, each NA independently comprises 16-20 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (Va), (VI), and embodiments thereof described herein. In one embodiment, the delivery system has a structure selected from formulas (I), (II), (III), (IV), (V), (Va) (VI), and embodiments thereof described herein further comprising 2 therapeutic nucleic acids (NA). In another embodiment, the delivery system has a structure selected from formulas (I), (II), (III), (IV), (V), (Va) (VI), and embodiments thereof described herein further comprising 3 therapeutic nucleic acids (NA). In one embodiment, the delivery system has a structure selected from formulas (I), (II), (III), (IV), (V), (Va), (VI), and embodiments thereof described herein further comprising 4 therapeutic nucleic acids (NA). In one embodiment, the delivery system has a structure selected from formulas (I), (II), (III), (IV), (V), (Va), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (Va), (VI), and embodiments thereof described herein further comprising 7 therapeutic nucleic acids (NA). In one embodiment, the delivery system has a structure selected from formulas (I), (II), (III), (IV), (V), (Va), (VI), and embodiments thereof described herein further comprising 8 therapeutic nucleic acids (NA).

In one embodiment, the delivery system has a structure selected from formulas (I), (II), (III), (IV), (V), (Va), (VI), further comprising a linker of structure L1 or L2 wherein R is R3 and n is 2. In another embodiment, the delivery system has a structure selected from formulas (I), (II), (III), (IV), (V), (Va), (VI), further comprising a linker of structure L1 wherein R is R3 and n is 2. In another embodiment, the delivery system has a structure selected from formulas (I), (II), (III), (IV), (V), (Va), (VI), further comprising a linker of structure L2 wherein R is R3 and n is 2.

Pharmaceutical Compositions and Methods of Administration

In one aspect, provided herein is a pharmaceutical composition comprising a therapeutically effective amount of one or more RNA silencing agents (e.g., siRNAs) as described herein, and a pharmaceutically acceptable carrier. In another particular embodiment, the pharmaceutical composition comprises a compound of Formula I-VI as described herein, and a pharmaceutically acceptable carrier.

The invention pertains to uses of the above-described agents for prophylactic and/or therapeutic treatments as described herein. Accordingly, the modulators (e.g., siRNA agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are particularly suitable. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies typically within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

In one aspect, the present invention provides for both prophylactic and therapeutic methods of treating a subject at risk of (or susceptible to) a disease or disorder.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In certain embodiments, the invention provides a method of treating a disease or disorder of the central nervous system with the oligonucleotides of the disclosure. The oligonucleotides, such as the antisense strands of double-stranded nucleic acids, may possess sufficient complementarity to a target gene implicated in the disease or disorder of the central nervous system. In particular embodiments, the target gene is Htt, ApoE, or C9ORF72. In particular embodiments, the disease or disorder of the central nervous system is Huntington's disease, Amyotrophic lateral sclerosis (ALS), or Alzheimer's disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., an siRNA or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

An oligonucleotide modified for enhanced uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmol of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly suitable dosages are less than 2, 1, or 0.1 mg/kg of body weight.

Delivery of an oligonucleotide directly to an organ can be at a dosage on the order of about 0.00001 mg to about 3 mg per organ, or about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an oligonucleotide. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are typically administered no more than once every 5, 10, or 30 days. Further, the treatment regimen may last for a period of time which will vary depending upon the nature of the particular disease, its severity and the overall condition of the patient. In certain exemplary embodiments, the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

In another aspect, provided herein is a method of treating or managing a disease or disorder comprising administering to a patient in need of such treatment or management a therapeutically effective amount of a compound, oligonucleotide, or nucleic acid as described herein, or a pharmaceutical composition comprising said compound, oligonucleotide, or nucleic acid.

In certain exemplary embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. An exemplary route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. In addition to an siRNA of the invention, a patient can be administered a second therapy, e.g., a palliative therapy and/or disease-specific therapy. The secondary therapy can be, for example, symptomatic (e.g., for alleviating symptoms), protective (e.g., for slowing or halting disease progression), or restorative (e.g., for reversing the disease process).

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An siRNA of the invention can be further modified such that it is capable of traversing the blood brain barrier (BBB). For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent IL, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mäger I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mäger I, Wood M J. (2013). Exosomes for targeted siRNA delivery across biological barriers. Adv. Drug Deliv Rev. 2013 March; 65(3):391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeablizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration typically do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An oligonucleotide of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are particularly suitable. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A particularly suitable group of carbohydrates includes lactose, trehalose, raffinose maltodextrins, and mannitol. Suitable polypeptides include aspartame. Amino acids include alanine and glycine, with glycine being preferred.

pH adjusters or buffers include organic salts prepared from organic acids and bases, such as sodium citrate, sodium ascorbate, and the like; sodium citrate is preferred.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier. It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1. Efficacy of 2'-O-Methyl-Rich hsiRNAs Having Reduced 2' Fluoro Modifications O-Methyl-rich, asymmetric hsiRNAs having reduced 2'-fluoro modifications (2'-fluoro modifications at positions 2 and 14 (circles) or 2'-fluoro modifications at positions 2, 4, 6, 8 and 14 (squares)) (FIG. 4C) were analyzed for silencing efficacy compared to a control hsiRNA having an alternating 2'-O-methyl/2'-fluoro modification pattern (triangles) (FIG. 4C).

Figure 4A:
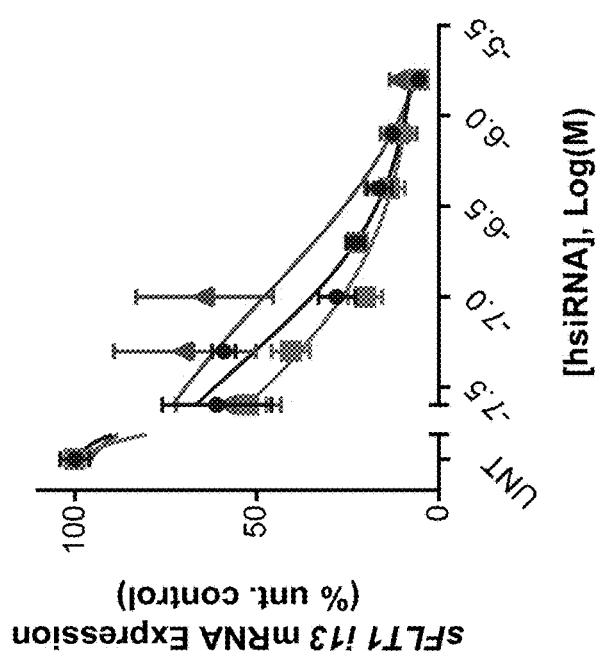
FIG. 4A-FIG. 4C depict increased efficacy of sFLT1i13 mRNA silencing with increased 2'-O'methyl content.
Figure 4B:
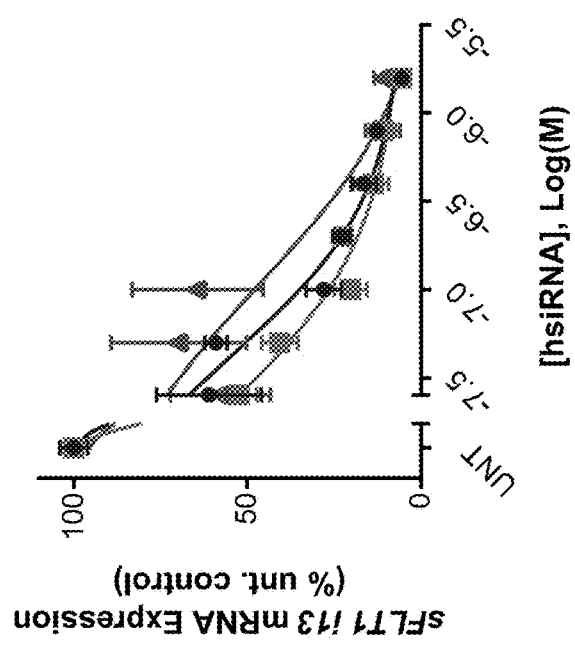
Figure 4C:
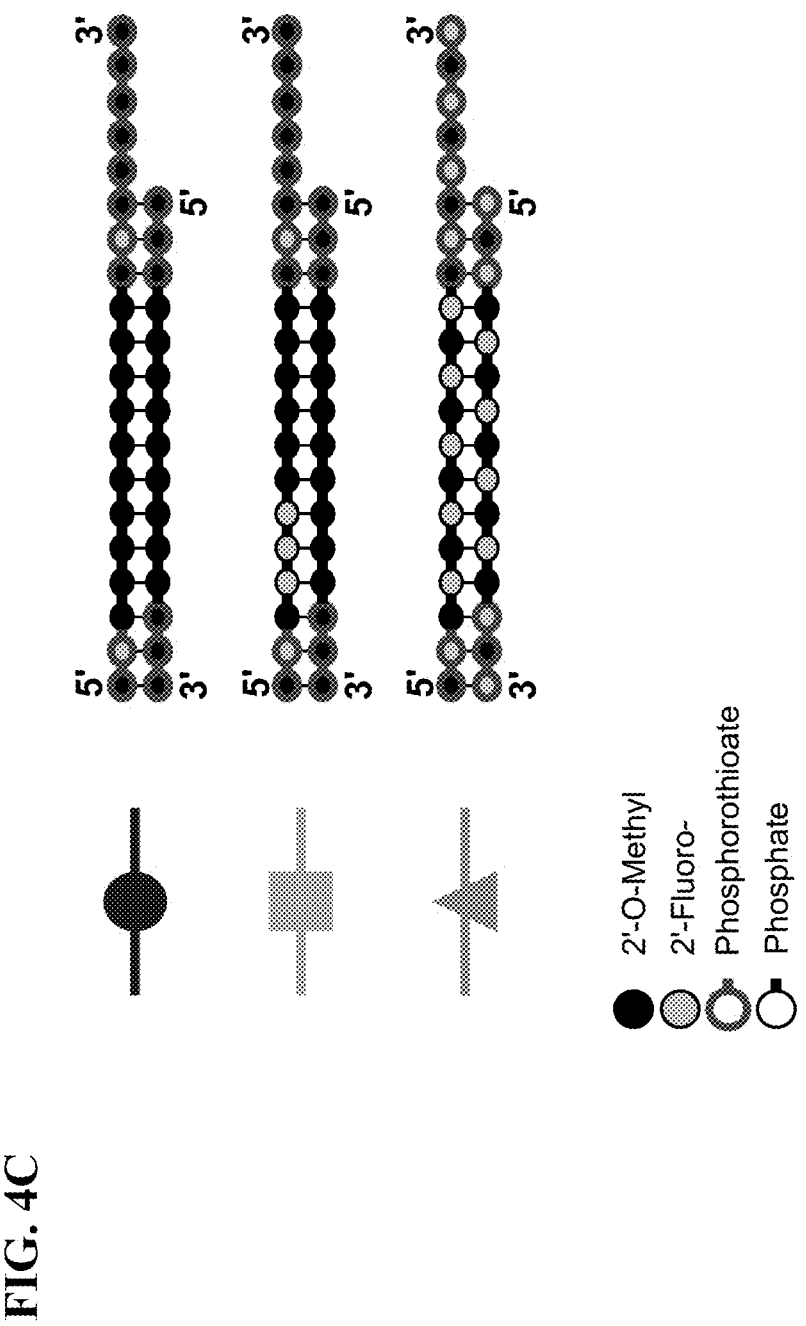
Figures 5A, 5B:
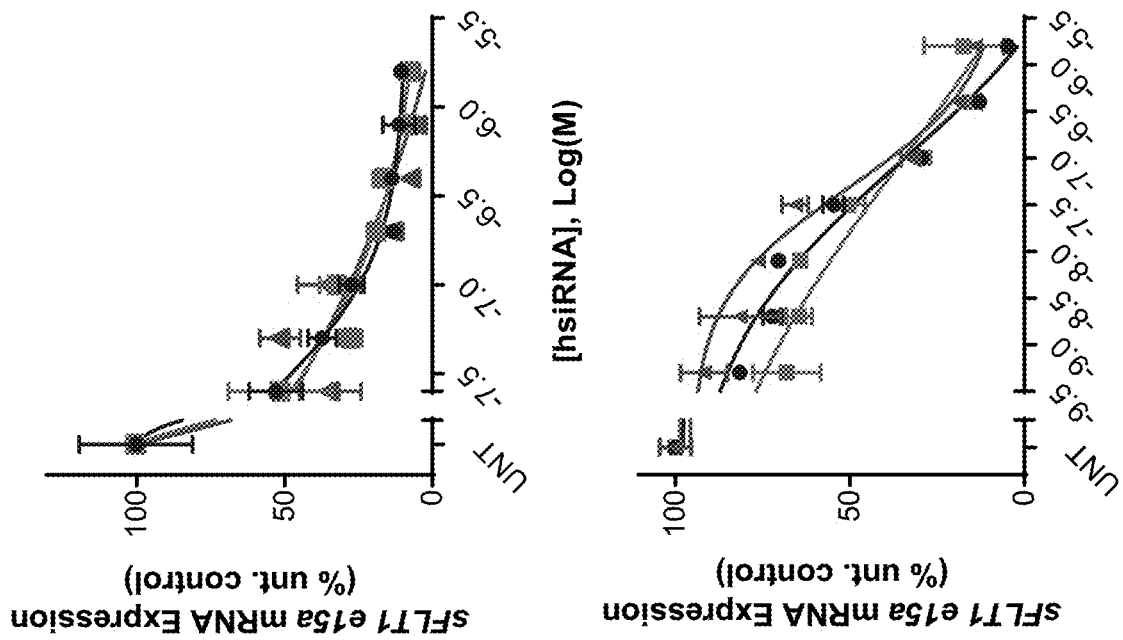
FIG. 5A-FIG. 5B depict increased efficacy of sFLTe15a mRNA silencing with increased 2'-O'methyl content.

The efficacies of individual hsiRNAs for silencing sFTL1 i13 mRNA was determined (FIG. 4A, FIG. 4B). The efficacies of individual hsiRNAs for silencing sFTL1 e15a mRNA was also determined (FIG. 5A, FIG. 5B). These data demonstrate that O-methyl rich, asymmetric, fully modified siRNAs having minimal 2'-fluoro modifications acquired unexpected improvements in efficacy properties in vitro, across two different cell lines using two different assays.

```
sFLT1 i13_2283 O-methyl-rich antisense strand:
                                       (SEQ ID NO: 10)
VP(mU)#(fA)#(mA)(fA)(fU)(fU)(mU)(mG)(mG)(mA)(mG)
(mA)(mU)#(fC)#(mC)#(mG)#(mA)#(mG)#(mA)#(mG)

sFLT1 i13_2283 O-methyl-rich sense strand:
                                       (SEQ ID NO: 11)
(mG)#(mG)#(mA)(mU)(mC)(mU)(mC)(mC)(mA)(mA)(mA)
(mU)(mU)#(mU)#(mA)

sFLT1 e15a_2519 OME antisense strand:
                                       (SEQ ID NO: 12)
VP(mU)#(fA)#(mU)(mA)(mA)(mA)(mU)(mG)(mG)(mU)(mA)
(mG)(mC)#(fU)#(mA)#(mU)#(mG)#(mA)#(mU)#(mG)

sFLT1 e15a_2519 OME sense strand:
                                       (SEQ ID NO: 13)
(mU)#(mA)#(mG)(mC)(mU)(mA)(mC)(mC)(mA)(mU)(mU)
(mU)(mA)#(mU)#(mA)
```

Example 2. Tissue Distribution of 2'-O-Methyl-Rich hsiRNAs Having Reduced 2' Fluoro Modifications O-Methyl-rich, asymmetric hsiRNAs comprising DCA or PC-DCA modifications were administered to CD1 pregnant mice, and their tissue distributions were assessed. O-methyl-rich-DCA and O-methyl-rich-PC-DCA hsiRNAs demonstrated increased or similar guide strand accumulation in the liver, kidney, and placenta compared to a non-methyl rich control hsiRNAs, despite half dosing (FIG. 6A, FIG. 6B, FIG. 6C).

Figure 7:
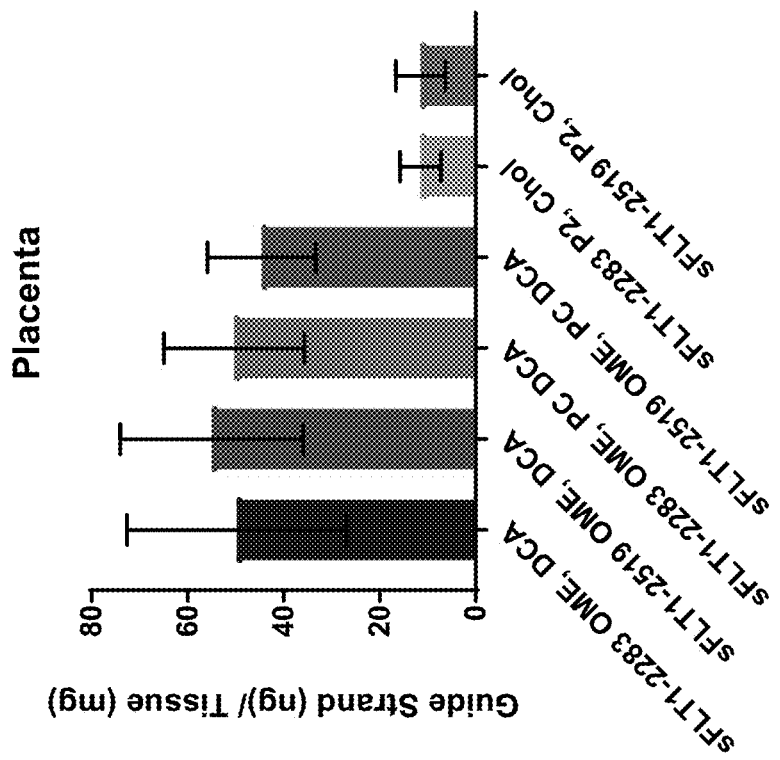
FIG. 7 depicts that O-methyl-rich DCA and PC DCA compounds showed increased or similar AS accumulation in the placenta compared to P2 Chol. CD1 pregnant mice were treated with O-methyl rich and P2 siRNAs at concentrations shown and tissues were harvested at indicated times. siRNA guide strands were measured in tissues using a peptide nucleic acid (PNA) hybridization assay. sFLT1-2283 O-methyl-rich: 20 mg/kg*, 120-hour dose; sFLT1-2519 O-methyl-rich: 20 mg/kg*, 120-hour dose; sFLT1-2283 P2: 10 mg/kg, 120-hour dose; sFLT1-2519 P2: 10 mg/kg, 120-hour dose. *40 mg/kg was the total dose of sFLT1-X siRNA (20 mg/kg sFLT1-2283+20 mg/kg sFLT1-2519a on E14). **20 mg/kg was the total dose of sFLT1-X siRNA (10 mg/kg sFLT1-2283+10 mg/kg sFLT1-2519).

CD1 pregnant mice were treated with O-methyl rich and P2 siRNAs, and their placental distributions were assessed. O-methyl-rich-DCA and O-methyl-rich E-PC DCA compounds demonstrated increased or similar guide strand accumulation in the placenta compared to P2-Chol hsiRNA (FIG. 7).

Figure 8C:
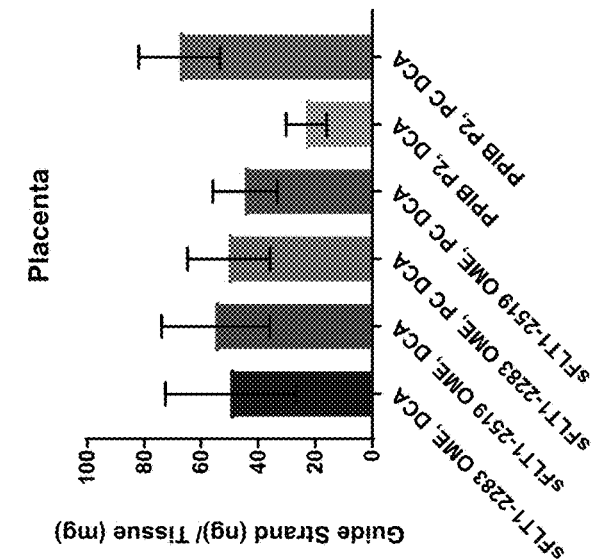
FIG. 8A-FIG. 8C depict O-methyl-rich compounds that show increased AS accumulation in the liver and placenta compared to PPIB P2, despite increased time to harvest. CD1 pregnant mice were treated with O-methyl rich sFLT1 and P2 PPIB siRNAs at concentrations shown and tissues were harvested at indicated times. siRNA guide strands were measured in tissues using a peptide nucleic acid (PNA) hybridization assay. PPIB P2: 20 mg/kg, 48-hour dose; sFLT1-X O-methyl-rich: 20 mg/kg*, 120-hour dose. *40 mg/kg was the total dose of sFLT1-X siRNA (20 mg/kg sFLT1-2283+20 mg/kg sFLT1-2519 on E14).
Figure 8A:
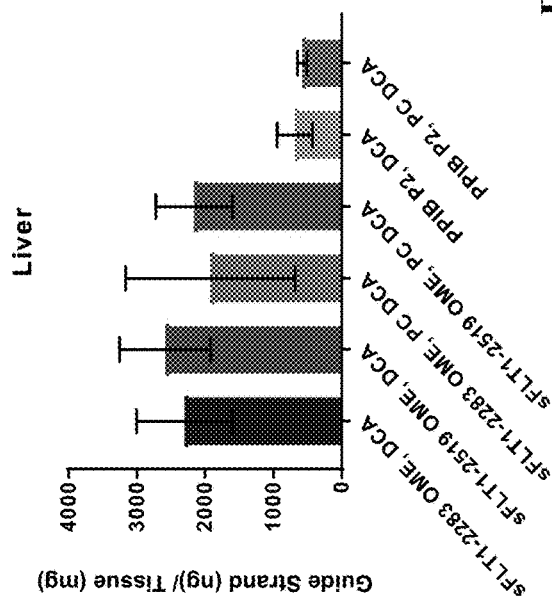
Figure 8B:
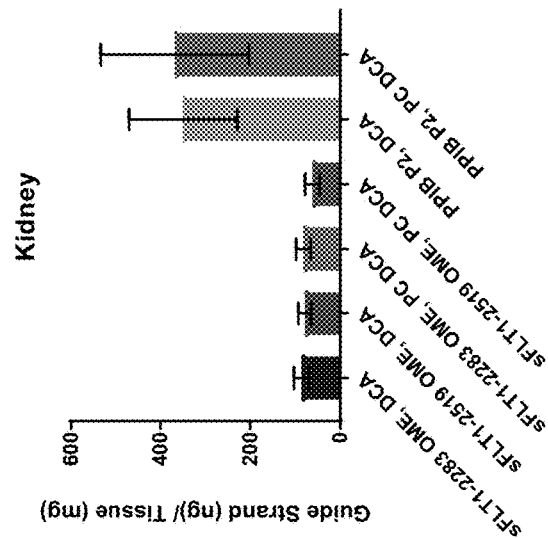
Figure 9A:
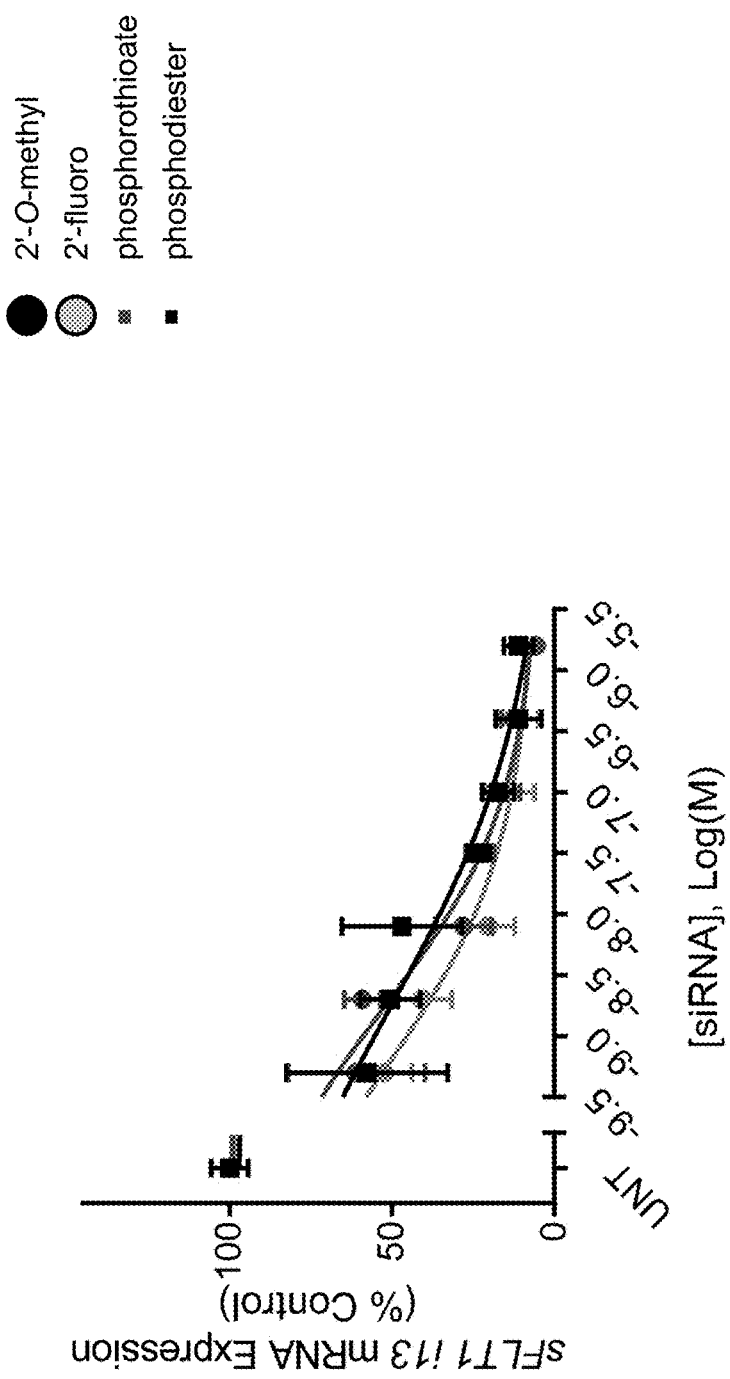
FIG. 9A-FIG. 9B depict in vitro efficacy of sFLT1i13 mRNA silencing with Pattern 1A.
Figure 9A:
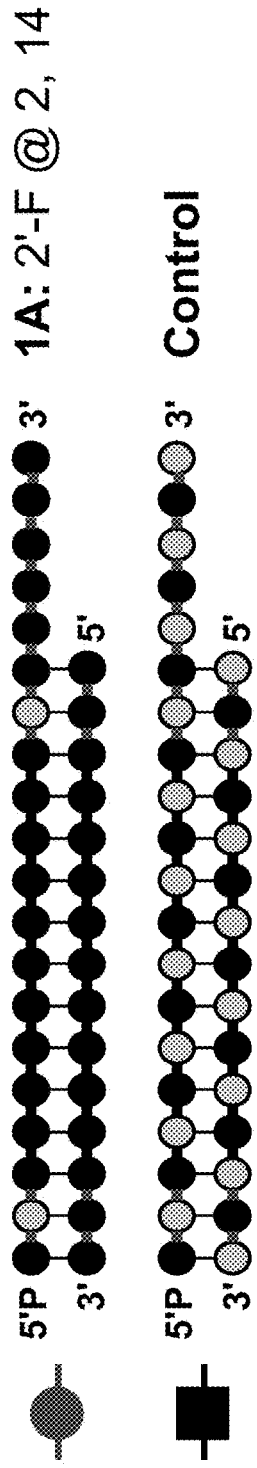
Figure 9B:
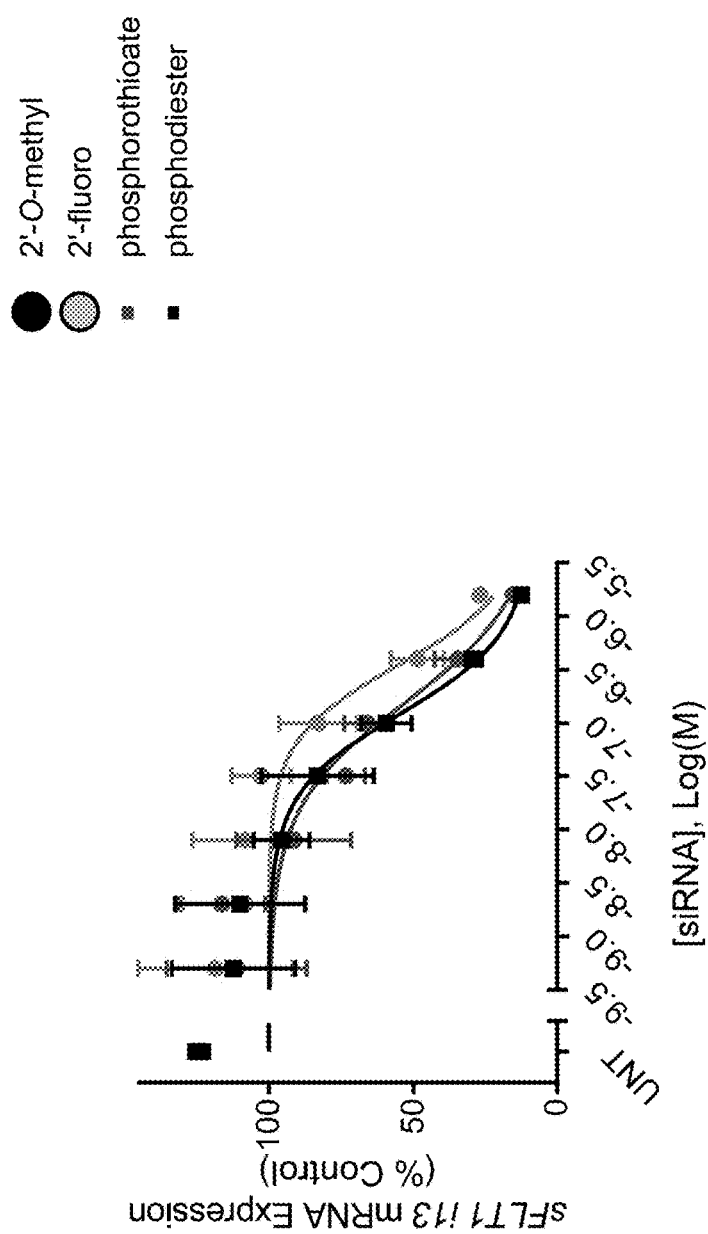
Figure 9B:
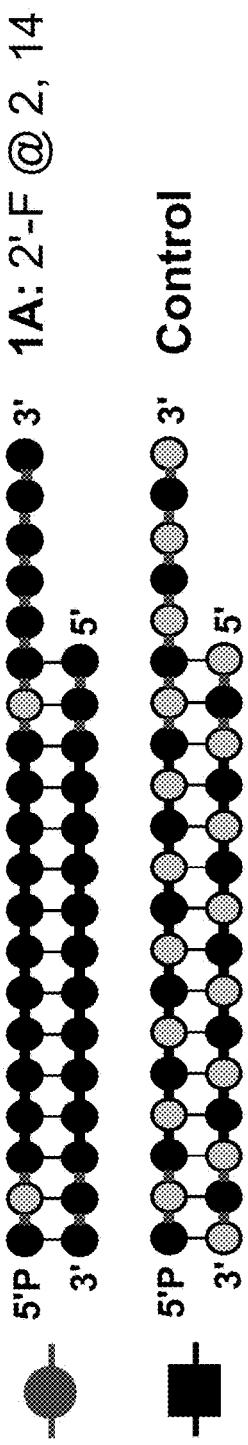
Figure 10A:
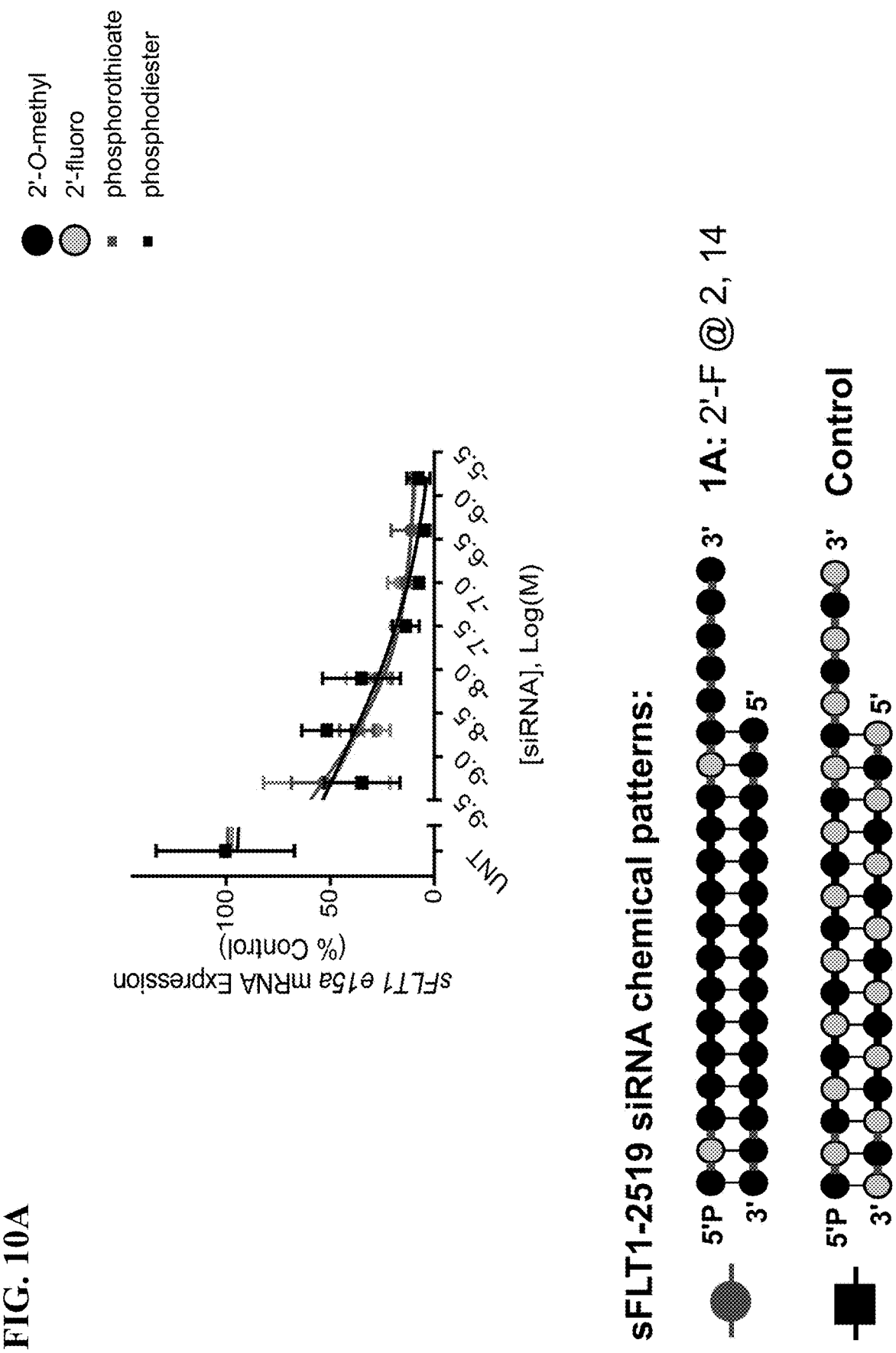
FIG. 10A-FIG. 10B depict in vitro efficacy of sFLTe15a mRNA silencing with Pattern 1A.
Figure 10B:
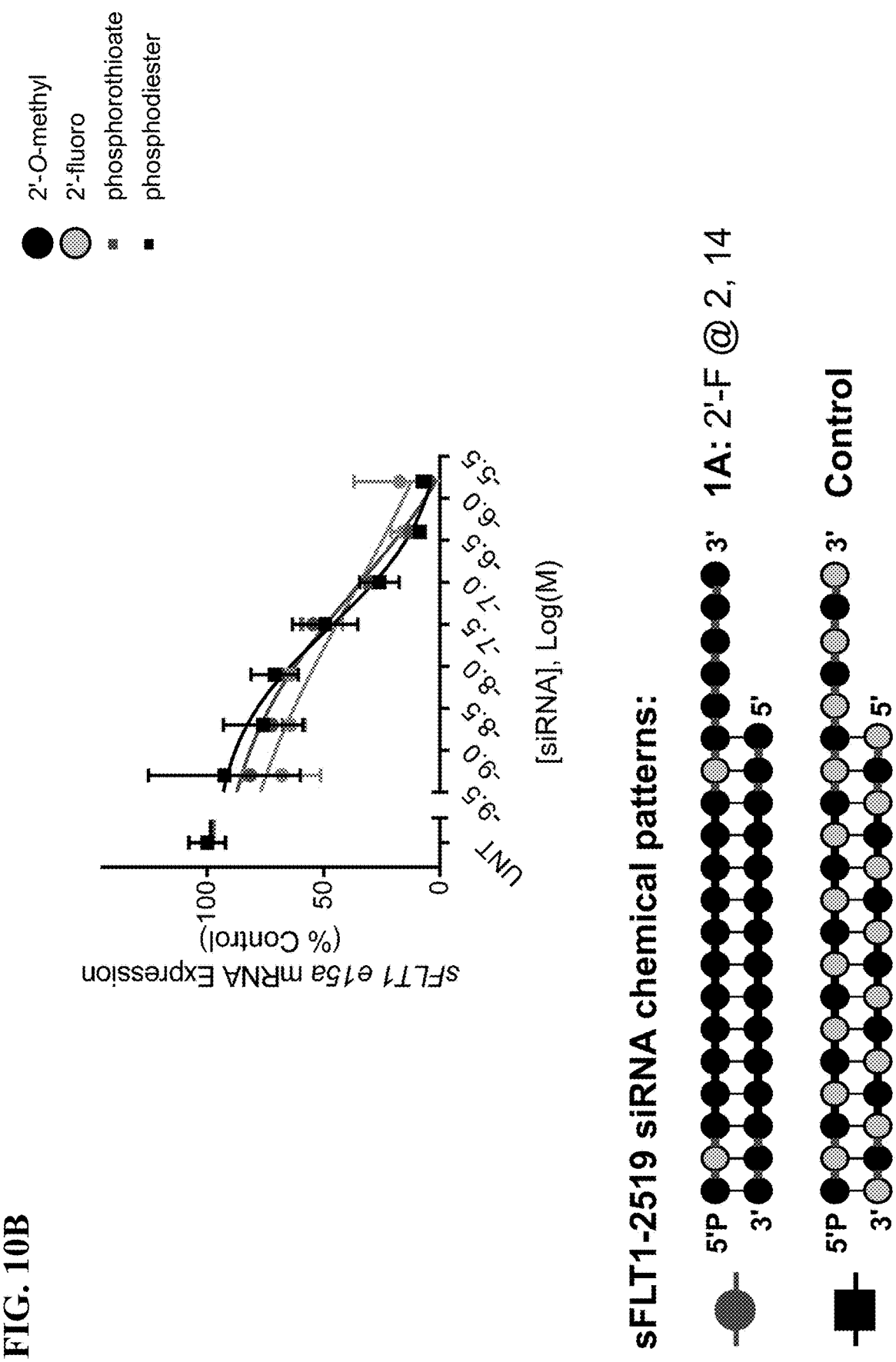
Figure 11A:
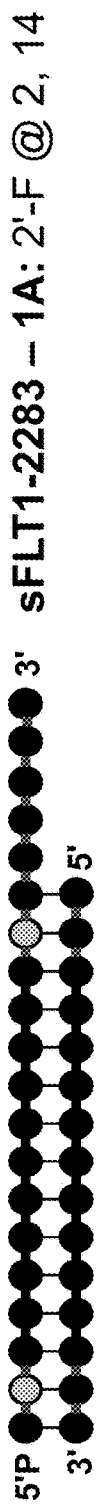
FIG. 11A-FIG. 11D depict that Pattern 1A DCA and PC DCA compounds show increased guide strand accumulation in the liver, kidney, and placenta compared to a control pattern with a cholesterol conjugate, despite ½ dosing.
Figure 11A:
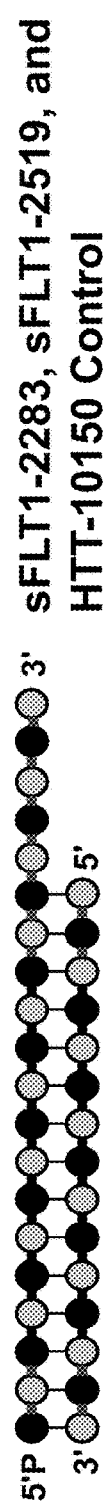
Figure 11A:
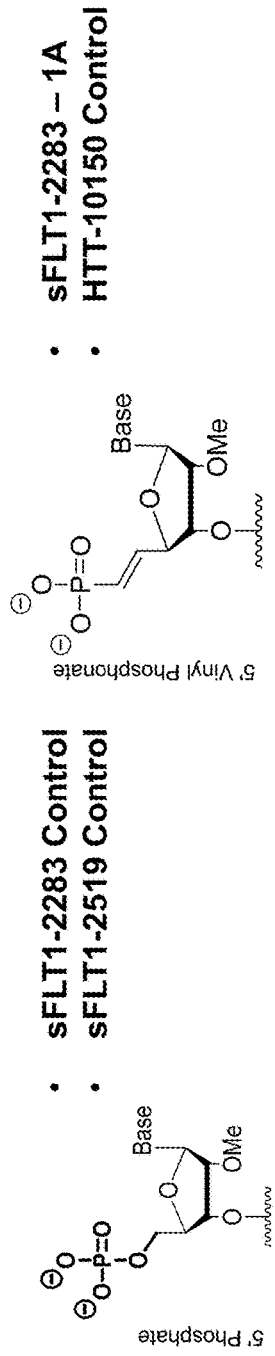
Figure 11A:
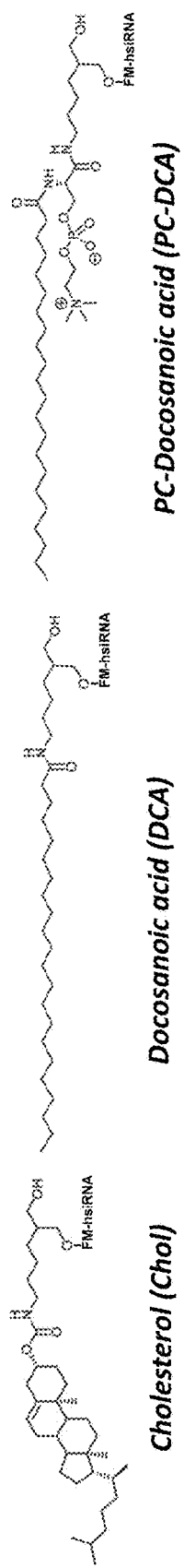
Figure 11B:
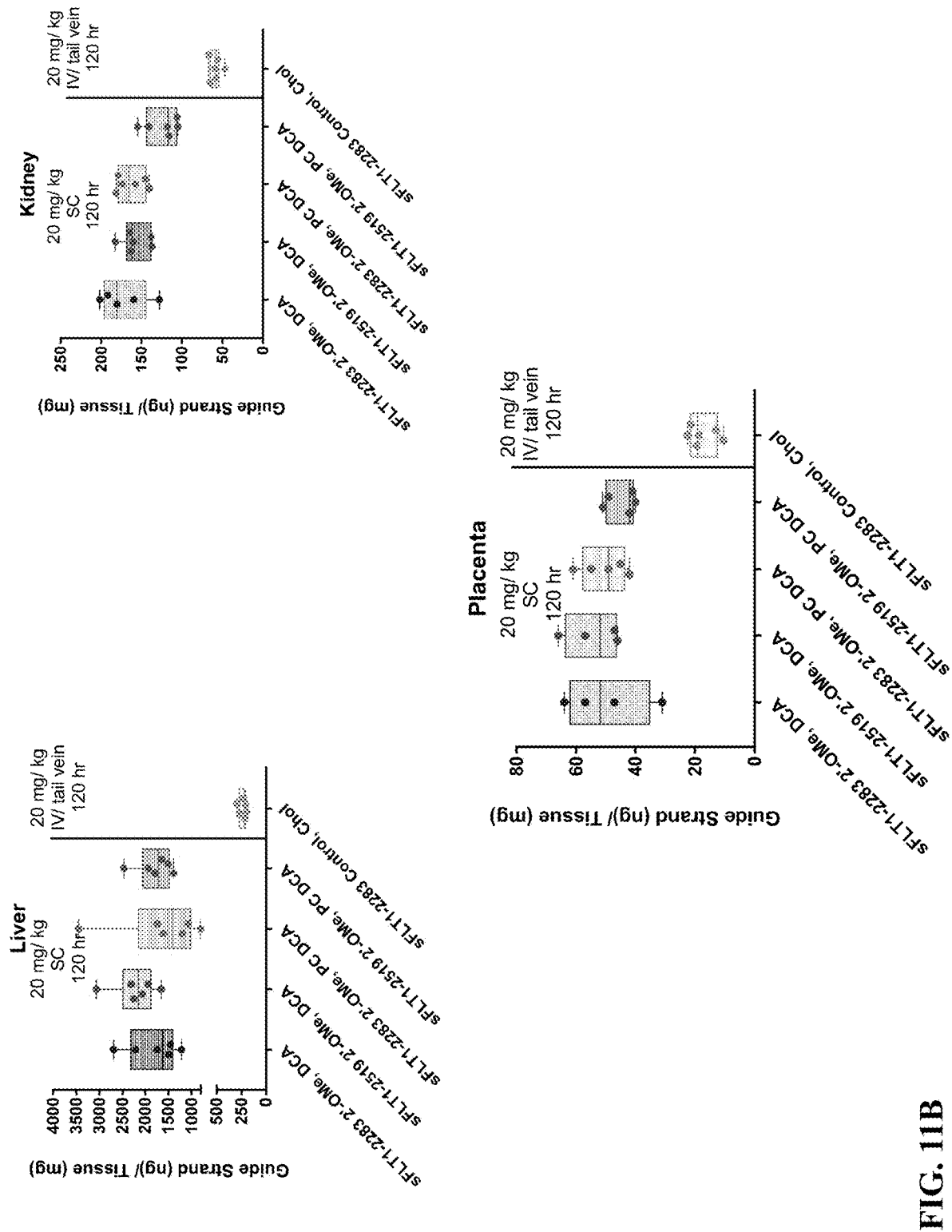
Figure 11C:
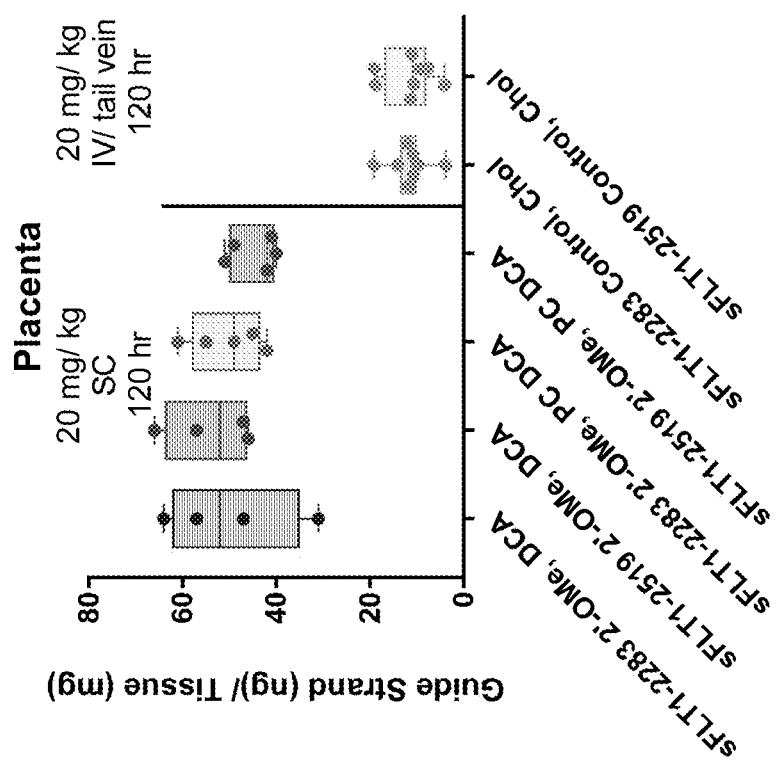
Figure 11D:
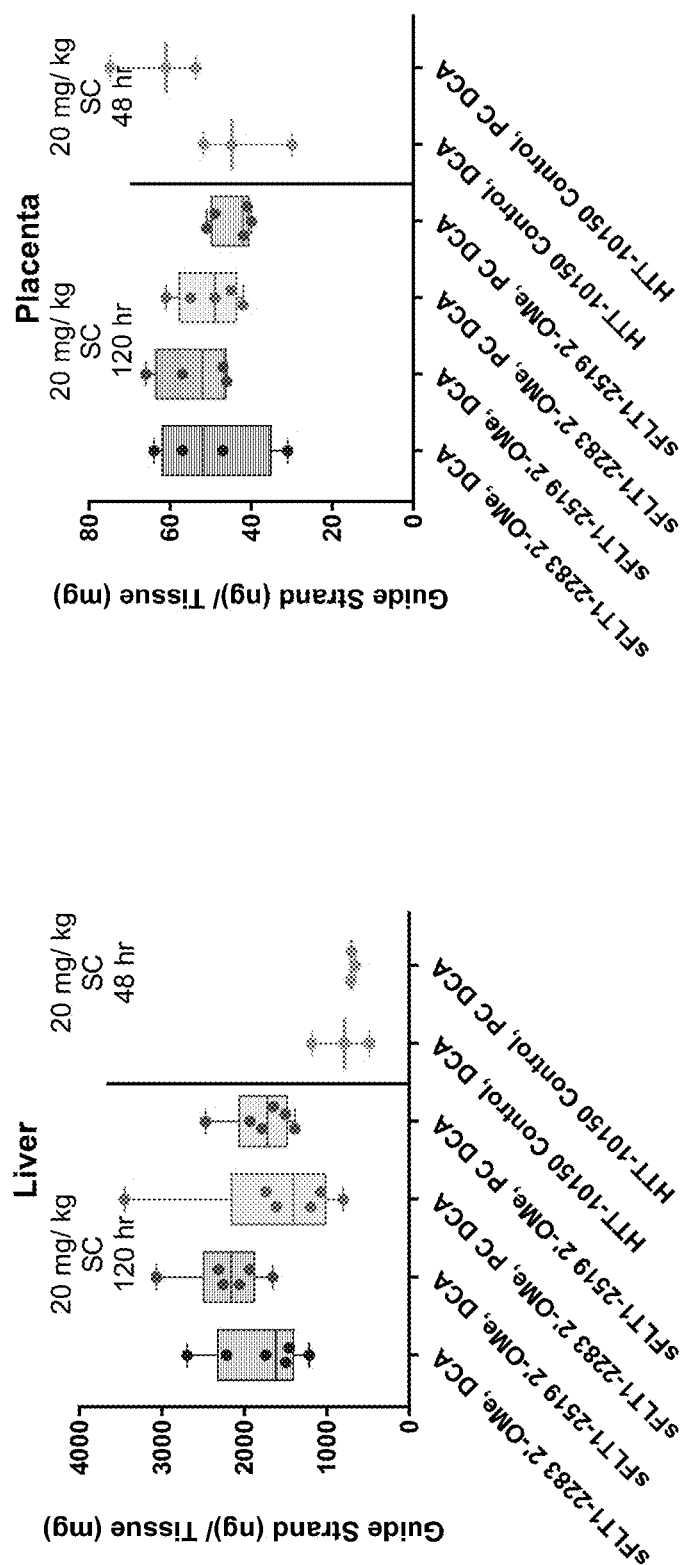

CD1 pregnant mice were treated with O-methyl rich sFLT1 and P2 PPIB siRNAs, and their tissue distributions were assessed. O-methyl-rich compounds demonstrated increased guide strand accumulation in the liver and placenta compared to PPIB P2 (FIG. 8A, FIG. 8B, FIG. 8C).

Example 3. Efficacy of 2'-O-Methyl-Rich hsiRNAs Having Reduced 2' Fluoro Modifications—Pattern 1

The O-methyl-rich, asymmetric hsiRNAs pattern of Example 1 was designed with an "A" variant, a "B" variant, a "C" variant, a "D" variant, a "E" variant, and a "F" variant (FIG. 1).

Pattern 1:

Pattern 1A—An siRNA with a 20-nucleotide guide (antisense) strand and a 15-nucleotide passenger (sense) strand. No 2'-O-methyl (2'-OMe) modification at positions 2 and 14 from the 5' end of the guide strand. 100% 2'-OMe modification of the passenger strand.

Pattern 1B—An siRNA with a 20-nucleotide guide (antisense) strand and a 15-nucleotide passenger (sense) strand. No 2'-OMe modification at positions 2, 14, and 20 from the 5' end of the guide strand. 100% 2'-OMe modification of the passenger strand.

Pattern 1C—An siRNA with a 20-nucleotide guide (antisense) strand and a 18-nucleotide passenger (sense) strand. No 2'-OMe modification at positions 2 and 14 from the 5' end of the guide strand. 100% 2'-OMe modification of the passenger strand.

Pattern 1D—An siRNA with a 20-nucleotide guide (antisense) strand and a 18-nucleotide passenger (sense) strand. No 2'-OMe modification at positions 2, 14, and 20 from the 5' end of the guide strand. 100% 2'-OMe modification of the passenger strand.

Pattern 1 is reproduced below, where "mN" is a 2'-O-methyl modified nucleotide, "fN" is a 2'-fluoro modified nucleotide, "#" is a phosphorothioate backbone modification, and "N" is a nucleotide selected from A, U, G, or C:

Pattern 1A
Antisense 5' to 3' (20 nucleotides)
(SEQ ID NO: 14)
(mN)#(xN)#(mN)(mN)(mN)(mN)(mN)(mN)(mN)(mN)(mN)
(mN)(mN)#(xN)#(mN)#(mN)#(mN)#(mN)#(mN)#(mN)

Sense 5' to 3' (15 nucleotides)
(SEQ ID NO: 4)
(mN)#(mN)#(mN)(mN)(mN)(mN)(mN)(mN)(mN)(mN)(mN)
(mN)(mN)#(mN)#(mN)

Pattern 1B
Antisense 5' to 3' (20 nucleotides)
(SEQ ID NO: 15)
(mN)#(xN)#(mN)(mN)(mN)(mN)(mN)(mN)(mN)(mN)(mN)
(mN)(mN)#(xN)#(mN)#(mN)#(mN)#(mN)#(mN)#(xN)

Sense 5' to 3' (15 nucleotides)
(SEQ ID NO: 4)
(mN)#(mN)#(mN)(mN)(mN)(mN)(mN)(mN)(mN)(mN)(mN)
(mN)(mN)#(mN)#(mN)

Pattern 1C
Antisense 5' to 3' (20 nucleotides)
(SEQ ID NO: 14)
(mN)#(xN)#(mN)(mN)(mN)(mN)(mN)(mN)(mN)(mN)(mN)
(mN)(mN)#(xN)#(mN)#(mN)#(mN)#(mN)#(mN)#(mN)

Sense 5' to 3' (18 nucleotides)
(SEQ ID NO: 6)
(mN)#(mN)#(mN)(mN)(mN)(mN)(mN)(mN)(mN)(mN)(mN)
(mN)(mN)(mN)(mN)#(mN)#(mN)

Pattern 1D
Antisense 5' to 3' (20 nucleotides)
(SEQ ID NO: 15)
(mN)#(xN)#(mN)(mN)(mN)(mN)(mN)(mN)(mN)(mN)(mN)
(mN)(mN)#(xN)#(mN)#(mN)#(mN)#(mN)#(mN)#(xN)

Sense 5' to 3' (18 nucleotides)
(SEQ ID NO: 6)
(mN)#(mN)#(mN)(mN)(mN)(mN)(mN)(mN)(mN)(mN)(mN)
(mN)(mN)(mN)(mN)#(mN)#(mN)

Pattern 1E
Antisense 5' to 3' (22 nucleotides)
(SEQ ID NO: 16)
(mN)#(xN)#(mN)(mN)(mN)(mN)(mN)(mN)(mN)(mN)(mN)
(mN)(mN)(xN)(mN)#(mN)#(mN)#(mN)#(mN)#(mN)#(mN)
(mN)

Sense 5' to 3' (20 nucleotides)
(SEQ ID NO: 8)
(mN)#(mN)#(mN)(mN)(mN)(mN)(mN)(mN)(mN)(mN)(mN)
(mN)(mN)(mN)(mN)(mN)(mN)#(mN)#(mN)

Pattern 1F
Antisense 5' to 3' (22 nucleotides)
(SEQ ID NO: 17)
(mN)#(xN)#(mN)(mN)(mN)(mN)(mN)(mN)(mN)(mN)(mN)
(mN)(mN)(xN)(mN)#(mN)#(mN)#(mN)#(mN)#(mN)#(mN)
(xN)

Sense 5' to 3' (20 nucleotides)
(SEQ ID NO: 8)
(mN)#(mN)#(mN)(mN)(mN)(mN)(mN)(mN)(mN)(mN)(mN)
(mN)(mN)(mN)(mN)(mN)(mN)#(mN)#(mN)

In Vitro Silencing—Pattern 1A:

The in vitro efficacies of Pattern 1A hsiRNAs for silencing sFTL1 i13 and sFTL1 e15a mRNA were determined (FIG. 9A, FIG. 9B, FIG. 10A, FIG. 10B). Pattern 1A (90% 2'O-Me content in guide strand) possess similar silencing efficacy to a control siRNA with 50% in guide strand. These data demonstrate that O-methyl rich, asymmetric, fully modified siRNAs having minimal 2'-fluoro modifications acquired unexpected improvements in efficacy properties in vitro, across two different cell lines, targeting two different mRNA target sequences, using two different assays.

In Vivo Tissue Accumulation—Pattern 1A and 1B:

The in vivo tissue accumulation of Pattern 1A hsiRNAs targeting sFTL1 i13 mRNA were determined (FIG. 11A-FIG. 11D). Pattern 1A hsiRNAs (sFlt1-2283 2'-OMe) comprising DCA or PC-DCA modifications and a 5' vinyl phosphonate were administered to CD1 pregnant mice, and their tissue distributions were assessed. O-methyl-rich-DCA and O-methyl-rich-PC-DCA hsiRNAs demonstrated increased or similar guide strand accumulation in the liver, kidney, and placenta compared to a non-methyl rich control hsiRNAs, despite half dosing. An additional control siRNA targeting Htt mRNA (HTT-10150) was included, with the sequence represented below.

```
HTT-10150 Antisense strand:
                                 (SEQ ID NO: 18)
UUAAUCUCUUUACUGAUAUA HTT-10150 mRNA target sequence:
                                 (SEQ ID NO: 19)
UAUAUCAGUAAAGAGAUUA
```

Figure 12B:
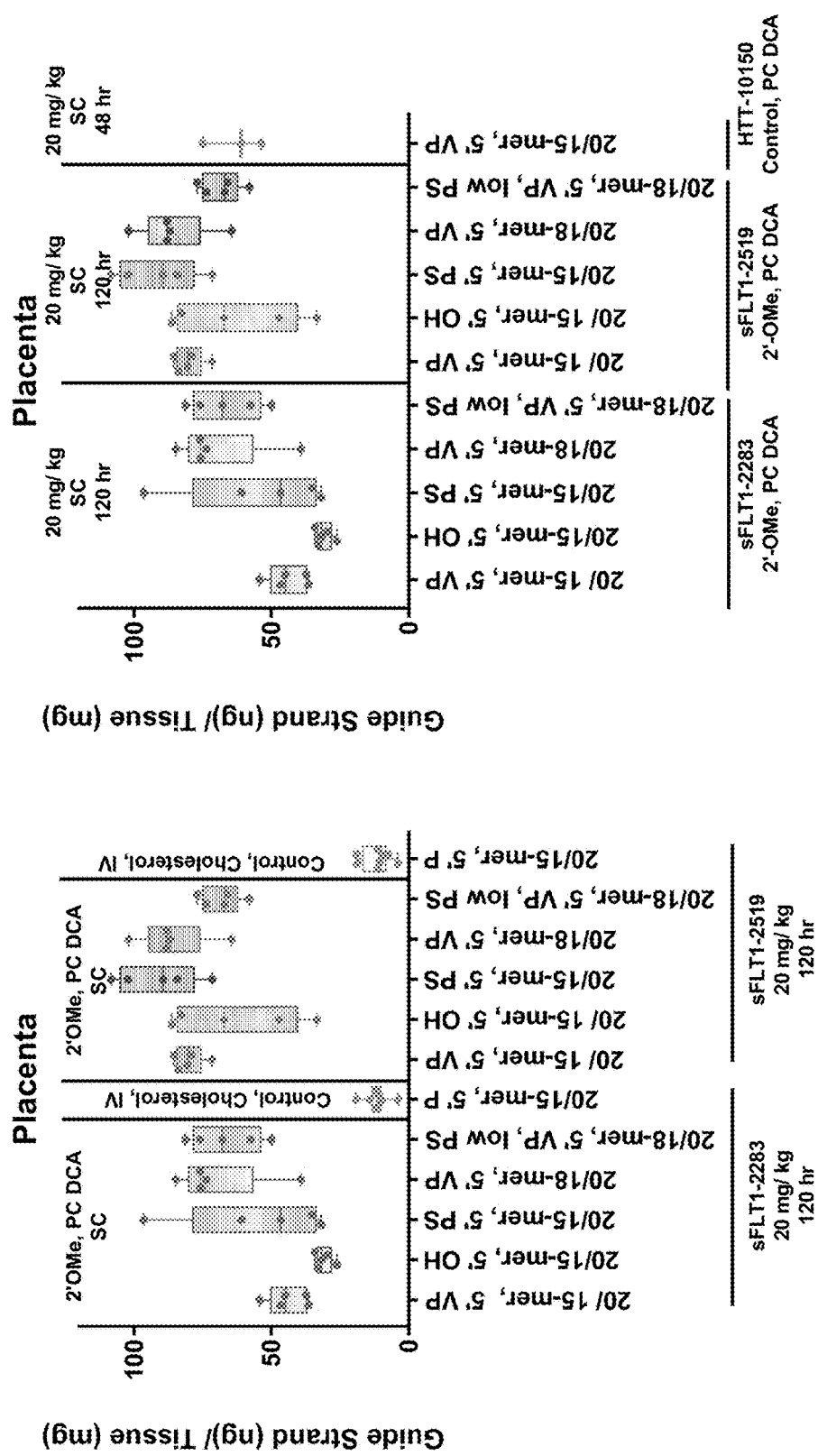

The in vivo tissue accumulation of Pattern 1B hsiRNAs targeting sFTL1 e15a mRNA were also determined (FIG. 12A, FIG. 12B). Pattern 1B O-methyl-rich-PC-DCA hsiR-NAs (sFlt1-2519 2'-OMe) demonstrated increased or similar guide strand accumulation in the placenta compared to a non-methyl rich control hsiRNAs. Different variants of the hsiRNAs were tested. As shown in FIG. 12B, "20/15 mer" represents 20 nucleotide antisense/15 nucleotide sense siR-NAs, "20/18 mer" represents 20 nucleotide antisense/18 nucleotide sense siRNAs, "5' VP" represents siRNAs with a 5' terminal vinyl phosphonate modification, "5' OH" represents siRNAs with a 5' terminal 2'-OH, "5' PS" represents siRNAs with a 5' terminal phosphorothioate, and "Low PS" represents siRNAs with phosphorothioate modifications at positions 1 and 2 from 5' and 3' end of antisense and sense strand.

Example 4. Efficacy of 2'-O-Methyl-Rich hsiRNAs Having Reduced 2' Fluoro Modifications—Role of Guide Strand Position 20

Figure 13A:
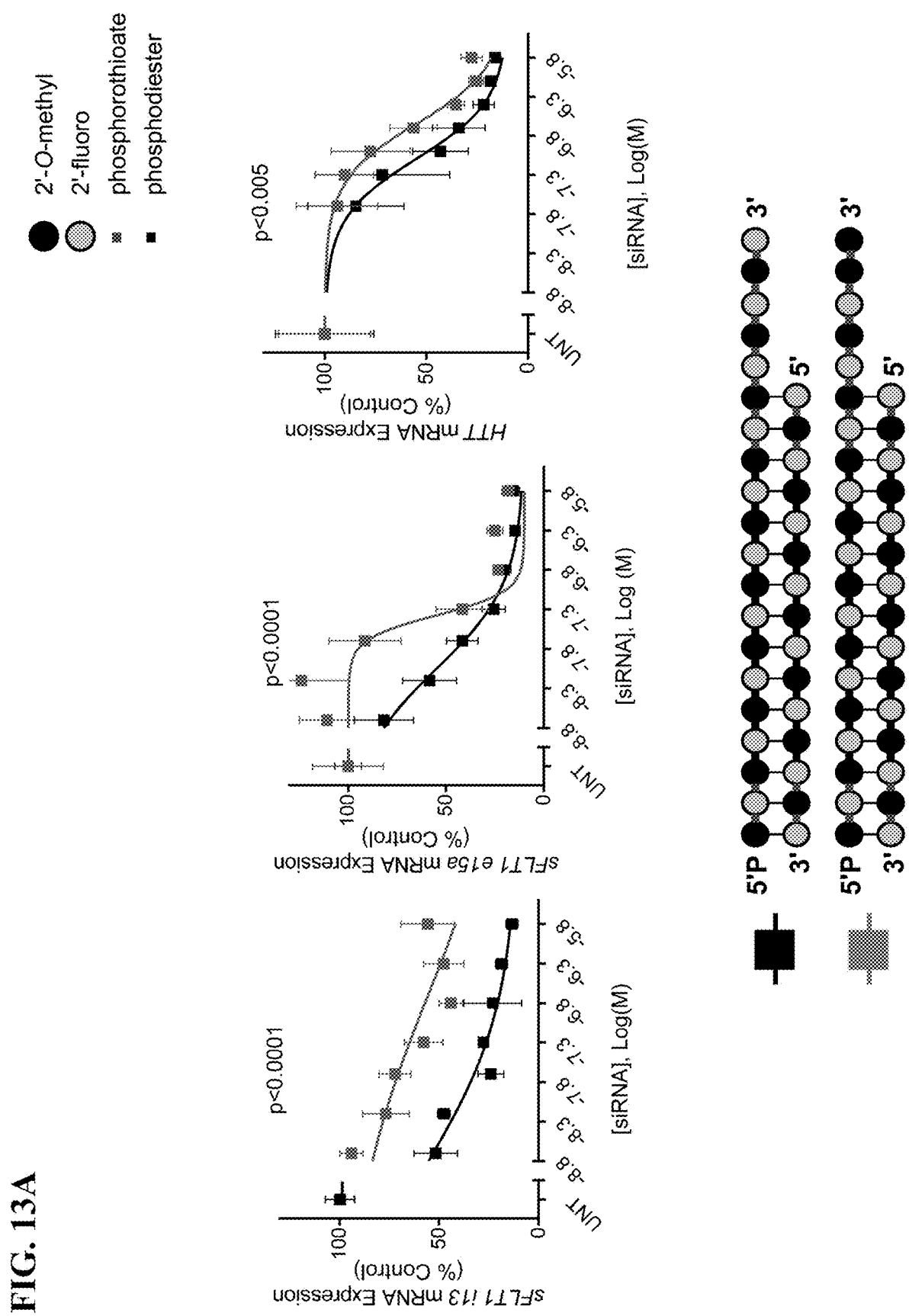
FIG. 13A-FIG. 13D depict in vitro efficacy of sFLT1i13, sFLT1e15a, and HTT mRNA silencing with siRNAs with or without a 2'-OMe at position 20 of the guide strand.
Figure 13B:
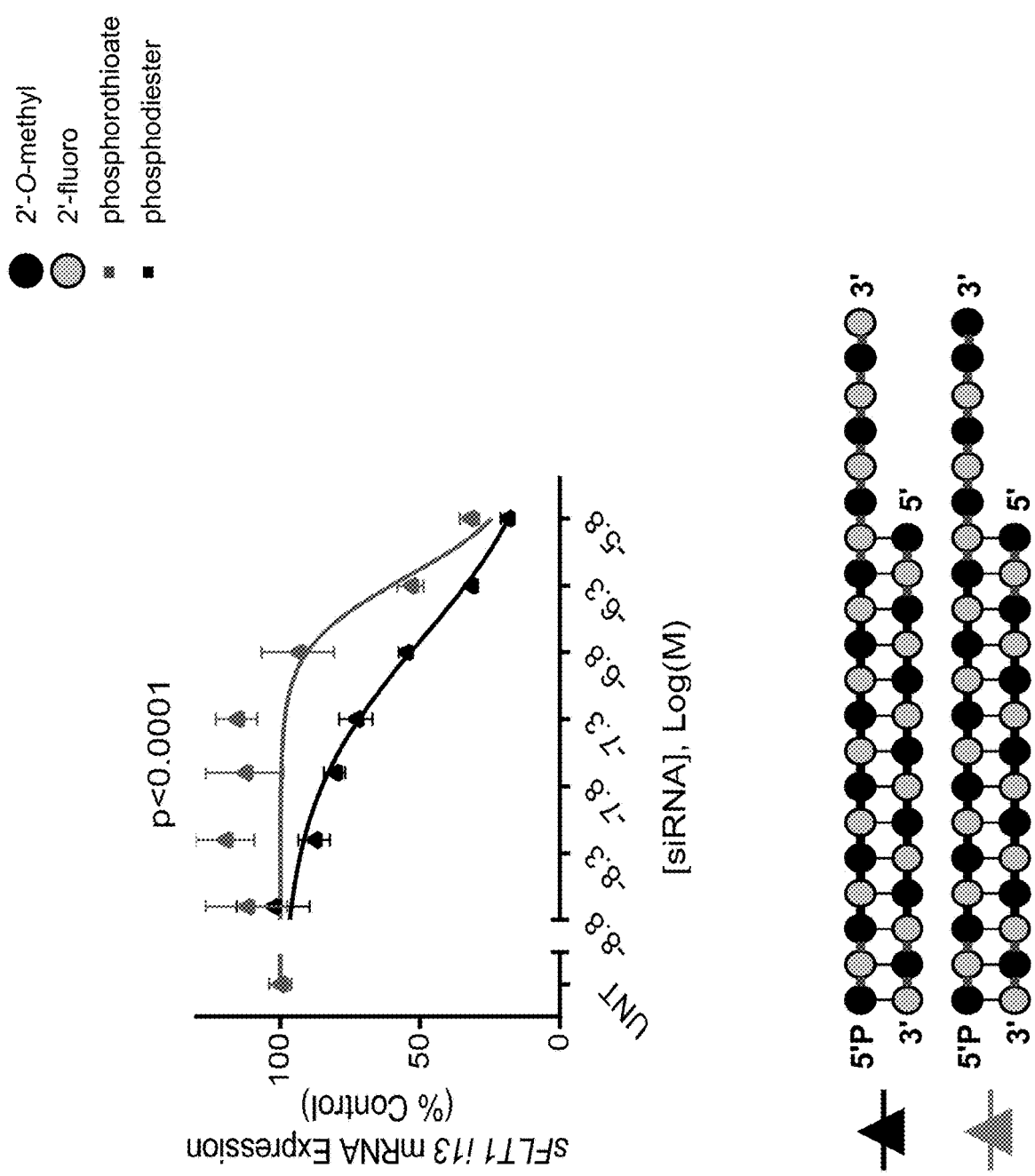
Figure 13C:
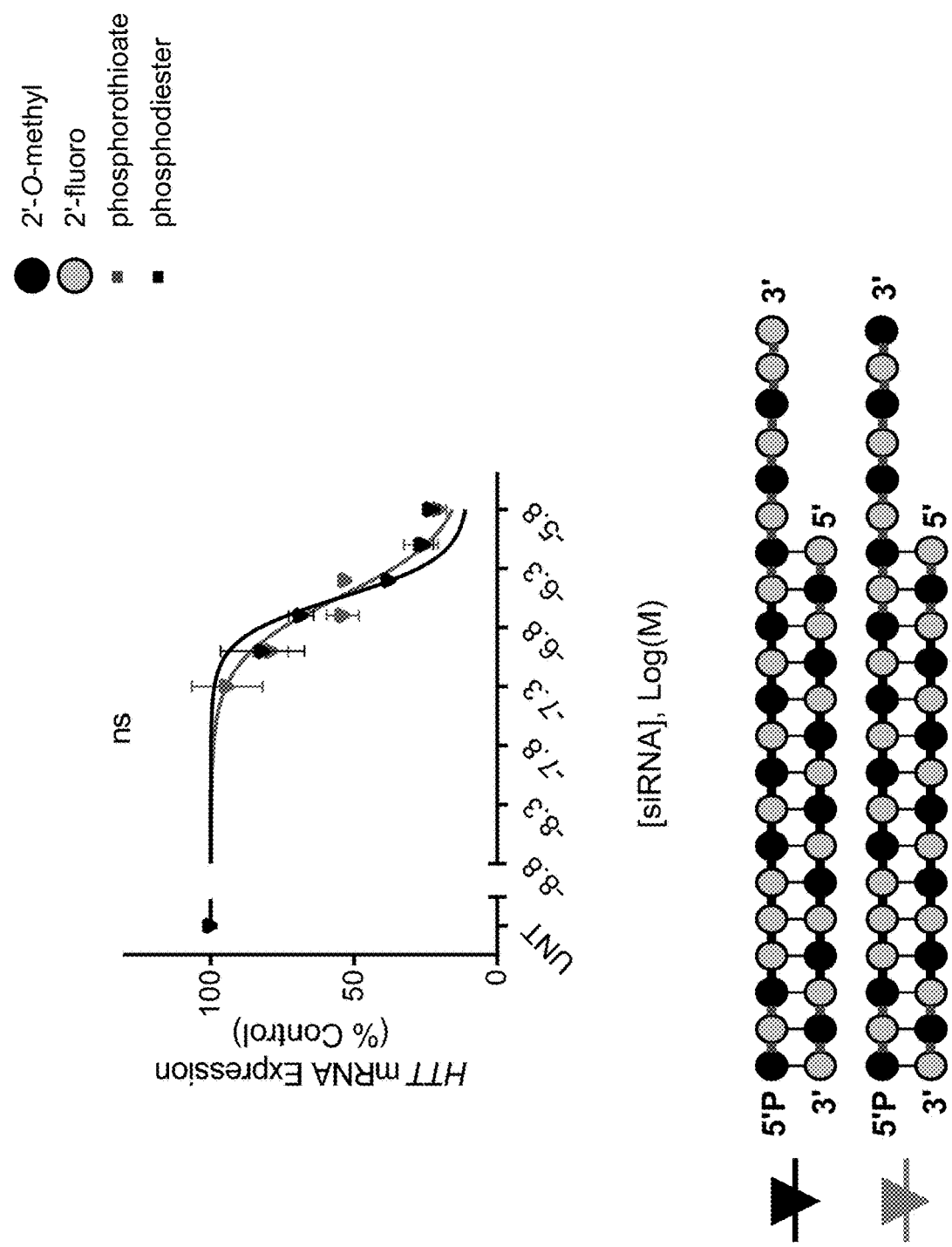
Figure 13D:
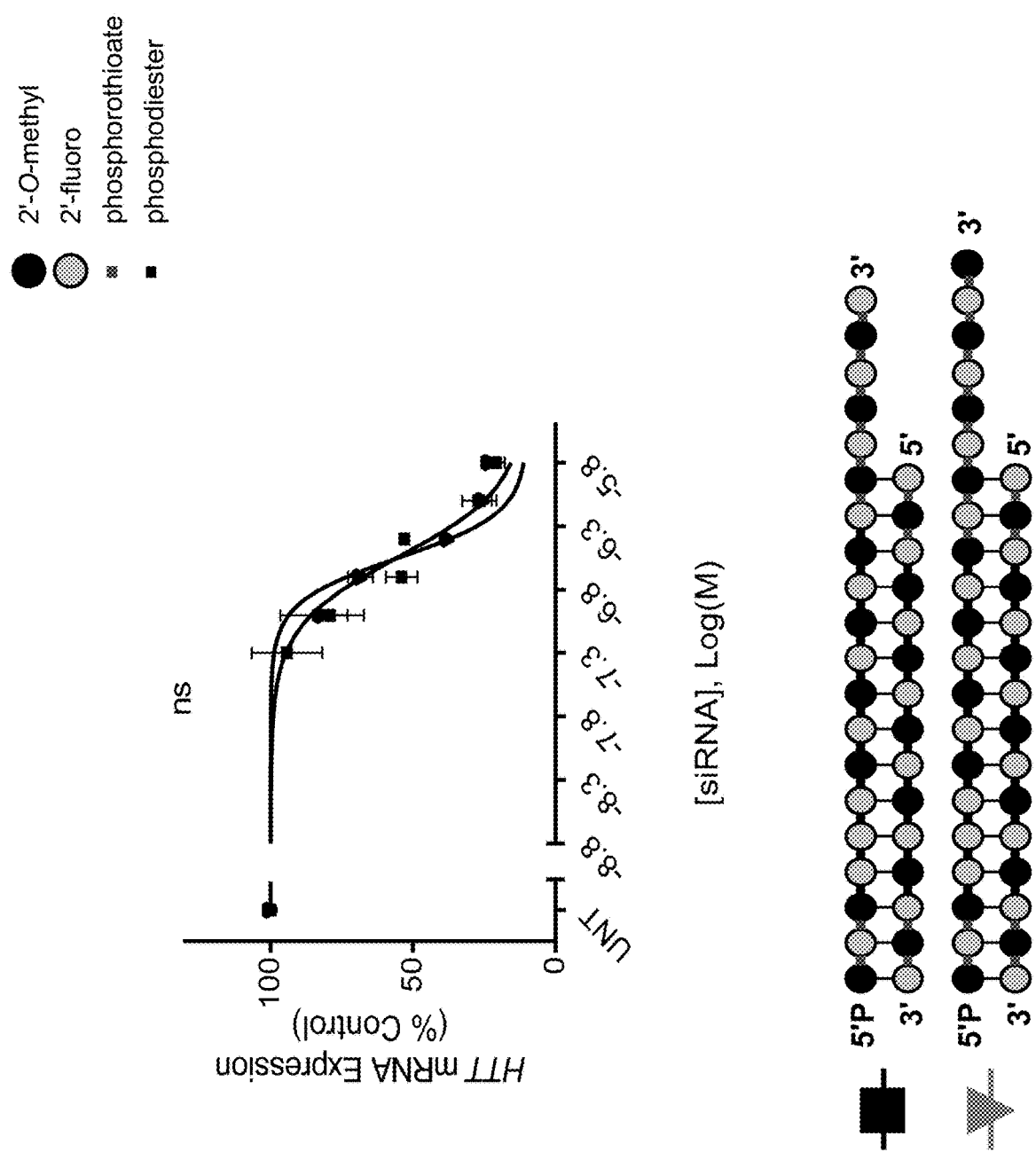

The in vitro efficacies of hsiRNAs with and without a 2'-O-Me modification at position 20 from the 5' end of the guide strand were determined (FIG. 13A-FIG. 13D).

hsiRNAs with 50-55% 2'-O-Me content in the guide strand for silencing sFTL1 i13, sFTL1 e15a, and Htt mRNA were used in Hela cells (FIG. 13A, FIG. 13C, and FIG. 13D) and WM-115 cells (FIG. 13B). These data demonstrate that when 2'-O-Me content is 50-55%, the lack of a 2'-O-Me at position 20 from the 5' end of the guide strand increases silencing efficacy. This was demonstrated with a 2'-fluoro modification at position 20, but may be applicable to other types of nucleotide modifications, including, but not limited to, 2'-H or an unmodified ribose with a 2'-OH. This increased silencing effect was demonstrated with two different chemical modification patterns, each with 50-55% 2'-O-Me content. FIG. 13D demonstrates the role of a 2'-flouro at position 20 in the context of a siRNA with a 21-nucleotide antisense strand, displaying similar results as a 20-nucleotide antisense strand.

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A double-stranded nucleic acid comprising an antisense strand and a sense strand, wherein:
the antisense strand comprises at least 14 contiguous nucleotides, a 5' end and a 3' end, and has complementarity to a target;
the sense strand comprises at least 13 contiguous nucleotides, a 5' end and a 3' end, and has complementarity to the antisense strand;
the antisense strand comprises at least 85% 2'-O-methyl modifications;
the nucleotides at positions 2 and 14 from the 5' end of the antisense strand comprise a non-2'-O-methyl modification; and
the nucleotides at positions 7, 9, 10, and 11 from the 3' end of the sense strand comprise a non-2'-O-methyl modification or the nucleotides at positions 7, 10, and 11 from the 3' end of the sense strand comprise a non-2'-O-methyl modification.

2. The double-stranded nucleic acid of claim 1, wherein the antisense strand comprises perfect or less than perfect complementarity to the target, optionally wherein the target comprises mammalian or viral mRNA.

3. The double-stranded nucleic acid of claim 2, wherein the antisense strand comprises 20 contiguous nucleotides or 22 contiguous nucleotides.

4. The double-stranded nucleic acid of claim 2, wherein the antisense strand comprises a 5' vinyl phosphonate.

5. The double-stranded nucleic acid of claim 1, wherein the antisense strand comprises at least 90% 2'-O-methyl modified nucleotides.

6. The double-stranded nucleic acid of claim 2, wherein one or more nucleotide mismatches are present at positions 2, 6, and 12 from the 5' end of sense strand.

7. The double-stranded nucleic acid of claim 1, wherein the nucleotide at position 20 from the 5' end of the antisense strand comprises a non-2'-O-methyl modification.

8. The double-stranded nucleic acid of claim 1, wherein one or more nucleotides at positions 1-7 from the 3' end of the antisense strand are connected to adjacent nucleotides via phosphorothioate linkages.

9. The double-stranded nucleic acid of claim 1, wherein the nucleotides at positions 1-6 from the 3' end or 1-7 from the 3' end of the antisense strand are connected to adjacent nucleotides via phosphorothioate linkages.

10. The double-stranded nucleic acid of claim 1, wherein the nucleotides at positions 2 and 14 from the 5' end of the antisense strand comprise a 2'-F modification or 2'-H modification, or a 2'-OH moiety.

11. The double-stranded nucleic acid of claim 1, wherein the antisense strand comprises between 15 and 22 contiguous nucleotides.

12. The double-stranded nucleic acid of claim 1, wherein the sense strand comprises between 15 and 20 contiguous nucleotides.

13. The double-stranded nucleic acid of claim 1, wherein the nucleotides at positions 1 and 2 from the 3' end of sense strand and/or the nucleotides at positions 1 and 2 from the 5' end of sense strand are connected to adjacent nucleotides via phosphorothioate linkages.

14. The double-stranded nucleic acid of claim 1, wherein the sense strand comprises a hydrophobic molecule at the 3' end of the sense strand.

15. The double-stranded nucleic acid of claim 1, wherein the sense strand comprises one or more nucleotide mismatches between the antisense strand and the sense strand.

16. The double-stranded nucleic acid of claim 1, wherein the antisense strand comprises a 5' phosphate, a 5'-alkyl phosphonate, a 5' alkylene phosphonate, or a 5' alkenyl phosphonate.

17. The double-stranded nucleic acid of claim 1, wherein the double-stranded nucleic acid comprises 4-16 phosphorothioate linkages or 8-13 phosphorothioate linkages.

18. The double-stranded nucleic acid of claim 1, wherein the double-stranded nucleic acid comprises double-stranded region of 15 base pairs to 20 base pairs.

19. The double-stranded nucleic acid of claim 1, wherein the sense strand comprises at least 80% 2'-O-methyl modified nucleotides, at least 90% 2'-O-methyl modified nucleotides, or 100% 2'-O-methyl modified nucleotides.

20. The double-stranded nucleic acid of claim 1, wherein the sense strand comprises 15 contiguous nucleotides, 18 contiguous nucleotides, or 20 contiguous nucleotides.

21. A pharmaceutical composition comprising one or more double-stranded nucleic acids of claim 1, and a pharmaceutically acceptable carrier.

22. A double-stranded nucleic acid comprising an antisense strand and a sense strand, wherein:
the antisense strand comprises at least 14 contiguous nucleotides, a 5' end and a 3' end, and has complementarity to a target;
the sense strand comprises at least 13 contiguous nucleotides, a 5' end and a 3' end, and has complementarity to the antisense strand;
the antisense strand comprises at least 85% 2'-O-methyl modifications;
the nucleotides at positions 2 and 14 from the 5' end of the first oligonucleotide are modified with 2'-F;
the sense strand comprises 100% 2'-O-methyl modifications; and
the nucleotides at positions 1-6 from the 3' end, or positions 1-7 from the 3' end, of the antisense strand are connected to adjacent nucleotides via phosphorothioate linkages.

23. A branched oligonucleotide compound capable of mediating RNA silencing in a cell, comprising two or more double-stranded nucleic acids, wherein the nucleic acids (N) are connected to one another by one or more moieties selected from a linker (L), a spacer (S) and optionally a branching point (B), wherein:

each double-stranded nucleic acid comprises an antisense strand and a sense strand, wherein each antisense strand comprises at least 14 contiguous nucleotides, a 5' end and a 3' end, and at least one antisense strand comprises at least 85% 2'-O-methyl modifications;

wherein the nucleotides at positions 2 and 14 from the 5' end of the at least one antisense strand comprise a non-2'-O-methyl modification; and wherein one or more nucleotides at positions 1-7 from the 3' end of at least one antisense strand are connected to adjacent nucleotides via phosphorothioate linkages.

24. The branched oligonucleotide compound of claim 23, wherein:

each antisense strand comprises at least 85% 2'-O-methyl modifications;

the nucleotides at positions 2 and 14 from the 5' end of each antisense strand comprise a non-2'-O-methyl modification;

one or more nucleotides at positions 1-7 from the 3' end of each antisense strand are connected to adjacent nucleotides via phosphorothioate linkages;

the nucleotides at positions 1 and 2 from the 5' end of the sense and antisense strands are connected to adjacent nucleotides via phosphorothioate linkages;

each double-stranded nucleic acid is independently connected to a linker, spacer or branching point at the 3' end or at the 5' end of the sense strand or the antisense strand;

the compound further comprises a hydrophobic moiety attached to the terminal 5' position of the branched oligonucleotide compound;

the nucleotide at position 20 from the 5' end of the antisense strand comprises a non-2'-O-methyl modification;

the antisense strand comprises 15, 16, 17, 18, 19, 20, 21, or 22 contiguous nucleotides; and the sense strand comprises 15, 16, 17, 18, 19, or 20 contiguous nucleotides.

25. The branched oligonucleotide compound of claim 24, wherein the hydrophobic moiety comprises an alkyl, alkenyl, or aryl moiety; a vitamin or cholesterol derivative; a lipophilic amino acid; or a combination thereof.

26. The branched oligonucleotide compound of claim 23, wherein each linker is independently selected from an ethylene glycol chain, an alkyl chain, a peptide, RNA, DNA, a phosphate, a phosphonate, a phosphoramidate, an ester, an amide, a triazole, or combinations thereof; and wherein any carbon or oxygen atom of the linker is optionally replaced with a nitrogen atom, bears a hydroxyl substituent, or bears an oxo substituent.

27. The branched oligonucleotide compound of claim 23, wherein the nucleotides at position 7, 10, and 11 from the 3' end of the sense strand comprise a non-2'-O-methyl modification.

28. The branched oligonucleotide compound of claim 23, wherein the non-2'-O-methyl modification comprises a 2'-F modification or 2'-H modification, or 2'-OH moiety.

29. The branched oligonucleotide compound of claim 23, wherein:

the antisense strand comprises at least 90% 2'-O-methyl modified nucleotides; and/or the sense strand comprises at least 80% 2'-O-methyl modified nucleotides, at least 90% 2'-O-methyl modified nucleotides, or 100% 2'-O-methyl modified nucleotides.

* * * * *

SEQUENCE LISTING

```
<160> NUMBER OF SEQ ID NOS: 19

<210> SEQ ID NO 1
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(20)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a non-2'-O-methyl modified
      nucleotide.
<220> FEATURE:
<221> NAME/KEY: misc_feature
<222> LOCATION: (3)..(3)
<223> OTHER INFORMATION: This nucleotide is a 2'-O-methyl modified
      nucleotide.
```

```
-continued

<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a non-2'-O-methyl modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (19)..(19)
<223> OTHER INFORMATION: This nucleotide is a 2'-O-methyl modified
```

```
            nucleotide.
<220> FEATURE:
<221> NAME/KEY: misc_feature
<222> LOCATION: (20)..(20)
<223> OTHER INFORMATION: This nucleotide is a 2'-O-methyl modified
      nucleotide.

<400> SEQUENCE: 1
nnnnnnnnnn nnnnnnnnnn                                               20

<210> SEQ ID NO 2
<211> LENGTH: 15
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(15)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-O-methyl modified
      nucleotide.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
```

```
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a 2'-O-methyl modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.

<400> SEQUENCE: 2
nnnnnnnnnn nnnnn                                                    15

<210> SEQ ID NO 3
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate
      linkage.
<220> FEATURE:
<221> NAME/KEY: misc_feature
<222> LOCATION: (1)..(20)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a non-2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
```

```
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate
      linkage.
<220> FEATURE:
<221> NAME/KEY: misc_feature
<222> LOCATION: (14)..(14)
<223> OTHER INFORMATION: This nucleotide is a non-2'-O-methyl modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate
      linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
```

-continued

```
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.

<400> SEQUENCE: 3
nnnnnnnnnn nnnnnnnnnn                                             20

<210> SEQ ID NO 4
<211> LENGTH: 15
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(15)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
```

```
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-O-methyl modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.

<400> SEQUENCE: 4
nnnnnnnnnn nnnnn                                                    15

<210> SEQ ID NO 5
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
```

```
<223> OTHER INFORMATION: These two nucleotides are connected by a
     phosphorothioate linkage.
<220> FEATURE:
<221> NAME/KEY: misc_feature
<222> LOCATION: (1)..(20)
<223> OTHER INFORMATION: N can be any nucleotide selected from A, U, G,
     or C.
<220> FEATURE:
<221> NAME/KEY: misc_feature
<222> LOCATION: (2)..(2)
<223> OTHER INFORMATION: This nucleotide is a non-2'-O-methyl modified
     nucleotide.
<220> FEATURE:
<221> NAME/KEY: misc_feature
<222> LOCATION: (2)..(3)
<223> OTHER INFORMATION: These two nucleotides are connected by a
     phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
     nucleotide.
<220> FEATURE:
<221> NAME/KEY: misc_feature
<222> LOCATION: (4)..(4)
<223> OTHER INFORMATION: This nucleotide is a 2'-O-methyl modified
     nucleotide.
<220> FEATURE:
<221> NAME/KEY: misc_feature
<222> LOCATION: (5)..(5)
<223> OTHER INFORMATION: This nucleotide is a 2'-O-methyl modified
     nucleotide.
<220> FEATURE:
<221> NAME/KEY: misc_feature
<222> LOCATION: (6)..(6)
<223> OTHER INFORMATION: This nucleotide is a 2'-O-methyl modified
     nucleotide.
<220> FEATURE:
<221> NAME/KEY: misc_feature
<222> LOCATION: (7)..(7)
<223> OTHER INFORMATION: This nucleotide is a 2'-O-methyl modified
     nucleotide.
<220> FEATURE:
<221> NAME/KEY: misc_feature
<222> LOCATION: (8)..(8)
<223> OTHER INFORMATION: This nucleotide is a 2'-O-methyl modified
     nucleotide.
<220> FEATURE:
<221> NAME/KEY: misc_feature
<222> LOCATION: (9)..(9)
<223> OTHER INFORMATION: This nucleotide is a 2'-O-methyl modified
     nucleotide.
<220> FEATURE:
<221> NAME/KEY: misc_feature
<222> LOCATION: (10)..(10)
<223> OTHER INFORMATION: This nucleotide is a 2'-O-methyl modified
     nucleotide.
<220> FEATURE:
<221> NAME/KEY: misc_feature
<222> LOCATION: (11)..(11)
<223> OTHER INFORMATION: This nucleotide is a 2'-O-methyl modified
     nucleotide.
<220> FEATURE:
<221> NAME/KEY: misc_feature
<222> LOCATION: (12)..(12)
<223> OTHER INFORMATION: This nucleotide is a 2'-O-methyl modified
     nucleotide.
<220> FEATURE:
<221> NAME/KEY: misc_feature
<222> LOCATION: (13)..(13)
<223> OTHER INFORMATION: This nucleotide is a 2'-O-methyl modified
     nucleotide.
<220> FEATURE:
<221> NAME/KEY: misc_feature
<222> LOCATION: (13)..(14)
<223> OTHER INFORMATION: These two nucleotides are connected by a
     phosphorothioate linkage.
<220> FEATURE:
<221> NAME/KEY: misc_feature
```

```
<222> LOCATION: (14)..(14)
<223> OTHER INFORMATION: This nucleotide is a non-2'-O-methyl modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a non-2'-O-methyl modified
      nucleotide.

<400> SEQUENCE: 5
nnnnnnnnnn nnnnnnnnnn                                              20

<210> SEQ ID NO 6
<211> LENGTH: 18
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
```

```
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(18)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
```

```
<223> OTHER INFORMATION: This nucleotide is a 2'-O-methyl modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.

<400> SEQUENCE: 6 nnnnnnnnn nnnnnnnn                                                    18

<210> SEQ ID NO 7
<211> LENGTH: 22
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(22)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a non-2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
```

-continued

```
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a non-2'-O-methyl modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
``` phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.
<220> FEATURE:
<221> NAME/KEY: misc_feature
<222> LOCATION: (20)..(21)
<223> OTHER INFORMATION: These two nucleotides are connected by a
      phosphorothioate linkage.
<220> FEATURE:
<221> NAME/KEY: misc_feature
<222> LOCATION: (21)..(21)
<223> OTHER INFORMATION: This nucleotide is a 2'-O-methyl modified
      nucleotide.
<220> FEATURE:
<221> NAME/KEY: misc_feature
<222> LOCATION: (21)..(22)
<223> OTHER INFORMATION: These two nucleotides are connected by a
      phosphorothioate linkage.
<220> FEATURE:
<221> NAME/KEY: misc_feature
<222> LOCATION: (22)..(22)
<223> OTHER INFORMATION: This nucleotide is a 2'-O-methyl modified
      nucleotide.

<400> SEQUENCE: 7
nnnnnnnnnn nnnnnnnnnn nn                                               22

<210> SEQ ID NO 8
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(20)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-O-methyl modified
      nucleotide.
<220> FEATURE:

```
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a 2'-O-methyl modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (17)..(17)
<223> OTHER INFORMATION: This nucleotide is a 2'-O-methyl modified
      nucleotide.
```

```
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.

<400> SEQUENCE: 8
nnnnnnnnnn nnnnnnnnnn                                              20

<210> SEQ ID NO 9
<211> LENGTH: 22
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(22)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a non-2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
```

```
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a non-2'-O-methyl modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
```

<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.
<220> FEATURE:
<221> NAME/KEY: misc_feature
<222> LOCATION: (20)..(21)
<223> OTHER INFORMATION: These two nucleotides are connected by a
      phosphorothioate linkage.
<220> FEATURE:
<221> NAME/KEY: misc_feature
<222> LOCATION: (21)..(21)
<223> OTHER INFORMATION: This nucleotide is a 2'-O-methyl modified
      nucleotide.
<220> FEATURE:
<221> NAME/KEY: misc_feature
<222> LOCATION: (21)..(22)
<223> OTHER INFORMATION: These two nucleotides are connected by a
      phosphorothioate linkage.
<220> FEATURE:
<221> NAME/KEY: misc_feature
<222> LOCATION: (22)..(22)
<223> OTHER INFORMATION: This nucleotide is a non-2'-O-methyl modified
      nucleotide.

<400> SEQUENCE: 9
nnnnnnnnnn nnnnnnnnnn nn                                             22

<210> SEQ ID NO 10
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(1)
<223> OTHER INFORMATION: This nucleotide comprises a vinyl phosphonate
      modification.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (2)..(2)
<223> OTHER INFORMATION: This nucleotide is a 2'-fluoro modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)

```
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-fluoro modified
      nucleotide.
<220> FEATURE:
<221> NAME/KEY: misc_feature
<222> LOCATION: (5)..(5)
<223> OTHER INFORMATION: This nucleotide is a 2'-fluoro modified
      nucleotide.
<220> FEATURE:
<221> NAME/KEY: misc_feature
<222> LOCATION: (6)..(6)
<223> OTHER INFORMATION: This nucleotide is a 2'-fluoro modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-fluoro modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
```

```
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.

<400> SEQUENCE: 10
uaaauuugga gauccgagag                                                   20

<210> SEQ ID NO 11
<211> LENGTH: 15
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (2)..(2)
<223> OTHER INFORMATION: This nucleotide is a 2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
```

```
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-O-methyl modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.

<400> SEQUENCE: 11
ggaucuccaa auuua                                                     15

<210> SEQ ID NO 12
<211> LENGTH: 20
```

```
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(1)
<223> OTHER INFORMATION: This nucleotide comprises a vinyl phosphonate
      modification.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (2)..(2)
<223> OTHER INFORMATION: This nucleotide is a 2'-fluoro modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
```

```
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-fluoro modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.

<400> SEQUENCE: 12
uauaaauggu agcuaugaug                                               20
```

```
<210> SEQ ID NO 13
<211> LENGTH: 15
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (2)..(2)
<223> OTHER INFORMATION: This nucleotide is a 2'-O-methyl modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
```

```
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-O-methyl modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.

<400> SEQUENCE: 13
uagcuaccau uuaua                                                       15

<210> SEQ ID NO 14
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(20)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-fluoro modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
```

```
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-fluoro modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
```

```
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.

<400> SEQUENCE: 14
nnnnnnnnnn nnnnnnnnnn                                                   20

<210> SEQ ID NO 15
<211> LENGTH: 20
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(20)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-fluoro modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
```

```
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (13)..(14)
<223> OTHER INFORMATION: These two nucleotides are connected by a
      phosphorothioate linkage.
<220> FEATURE:
<221> NAME/KEY: misc_feature
<222> LOCATION: (14)..(14)
<223> OTHER INFORMATION: This nucleotide is a 2'-fluoro modified
      nucleotide.
<220> FEATURE:
<221> NAME/KEY: misc_feature
<222> LOCATION: (14)..(15)
<223> OTHER INFORMATION: These two nucleotides are connected by a
      phosphorothioate linkage.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
```

```
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-fluoro modified
      nucleotide.

<400> SEQUENCE: 15
nnnnnnnnnn nnnnnnnnnn                                           20

<210> SEQ ID NO 16
<211> LENGTH: 22
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(22)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-fluoro modified
      nucleotide.
<220> FEATURE:
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
```

-continued

```
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a 2'-fluoro modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
```

```
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.
<220> FEATURE:
<221> NAME/KEY: misc_feature
<222> LOCATION: (20)..(21)
<223> OTHER INFORMATION: These two nucleotides are connected by a
      phosphorothioate linkage.
<220> FEATURE:
<221> NAME/KEY: misc_feature
<222> LOCATION: (21)..(21)
<223> OTHER INFORMATION: This nucleotide is a 2'-O-methyl modified
      nucleotide.
<220> FEATURE:
<221> NAME/KEY: misc_feature
<222> LOCATION: (21)..(22)
<223> OTHER INFORMATION: These two nucleotides are connected by a
      phosphorothioate linkage.
<220> FEATURE:
<221> NAME/KEY: misc_feature
<222> LOCATION: (22)..(22)
<223> OTHER INFORMATION: This nucleotide is a 2'-O-methyl modified
      nucleotide.

<400> SEQUENCE: 16
nnnnnnnnnn nnnnnnnnnn nn                                              22

<210> SEQ ID NO 17
<211> LENGTH: 22
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(1)
<223> OTHER INFORMATION: This nucleotide is a 2'-O-methyl modified
      nucleotide.
<220> FEATURE:
<221> NAME/KEY: misc_feature
<222> LOCATION: (1)..(2)
<223> OTHER INFORMATION: These two nucleotides are connected by a
      phosphorothioate linkage.
<220> FEATURE:
<221> NAME/KEY: misc_feature
<222> LOCATION: (1)..(22)
<223> OTHER INFORMATION: N can be any nucleotide selected from A, U, G,
      or C.
<220> FEATURE:
<221> NAME/KEY: misc_feature
<222> LOCATION: (2)..(2)
<223> OTHER INFORMATION: This nucleotide is a 2'-fluoro modified
      nucleotide.
<220> FEATURE:
```

```
<221> NAME/KEY: misc_feature
<222> LOCATION: (2)..(3)
<223> OTHER INFORMATION: These two nucleotides are connected by a
      phosphorothioate linkage.
<220> FEATURE:
<221> NAME/KEY: misc_feature
<222> LOCATION: (3)..(3)
<223> OTHER INFORMATION: This nucleotide is a 2'-O-methyl modified
      nucleotide.
<220> FEATURE:
<221> NAME/KEY: misc_feature
<222> LOCATION: (4)..(4)
<223> OTHER INFORMATION: This nucleotide is a 2'-O-methyl modified
      nucleotide.
<220> FEATURE:
<221> NAME/KEY: misc_feature
<222> LOCATION: (5)..(5)
<223> OTHER INFORMATION: This nucleotide is a 2'-O-methyl modified
      nucleotide.
<220> FEATURE:
<221> NAME/KEY: misc_feature
<222> LOCATION: (6)..(6)
<223> OTHER INFORMATION: This nucleotide is a 2'-O-methyl modified
      nucleotide.
<220> FEATURE:
<221> NAME/KEY: misc_feature
<222> LOCATION: (7)..(7)
<223> OTHER INFORMATION: This nucleotide is a 2'-O-methyl modified
      nucleotide.
<220> FEATURE:
<221> NAME/KEY: misc_feature
<222> LOCATION: (8)..(8)
<223> OTHER INFORMATION: This nucleotide is a 2'-O-methyl modified
      nucleotide.
<220> FEATURE:
<221> NAME/KEY: misc_feature
<222> LOCATION: (9)..(9)
<223> OTHER INFORMATION: This nucleotide is a 2'-O-methyl modified
      nucleotide.
<220> FEATURE:
<221> NAME/KEY: misc_feature
<222> LOCATION: (10)..(10)
<223> OTHER INFORMATION: This nucleotide is a 2'-O-methyl modified
      nucleotide.
<220> FEATURE:
<221> NAME/KEY: misc_feature
<222> LOCATION: (11)..(11)
<223> OTHER INFORMATION: This nucleotide is a 2'-O-methyl modified
      nucleotide.
<220> FEATURE:
<221> NAME/KEY: misc_feature
<222> LOCATION: (12)..(12)
<223> OTHER INFORMATION: This nucleotide is a 2'-O-methyl modified
      nucleotide.
<220> FEATURE:
<221> NAME/KEY: misc_feature
<222> LOCATION: (13)..(13)
<223> OTHER INFORMATION: This nucleotide is a 2'-O-methyl modified
      nucleotide.
<220> FEATURE:
<221> NAME/KEY: misc_feature
<222> LOCATION: (14)..(14)
<223> OTHER INFORMATION: This nucleotide is a 2'-fluoro modified
      nucleotide.
<220> FEATURE:
<221> NAME/KEY: misc_feature
<222> LOCATION: (15)..(15)
<223> OTHER INFORMATION: This nucleotide is a 2'-O-methyl modified
      nucleotide.
<220> FEATURE:
<221> NAME/KEY: misc_feature
<222> LOCATION: (15)..(16)
<223> OTHER INFORMATION: These two nucleotides are connected by a
      phosphorothioate linkage.
<220> FEATURE:
<221> NAME/KEY: misc_feature
<222> LOCATION: (16)..(16)
<223> OTHER INFORMATION: This nucleotide is a 2'-O-methyl modified
      nucleotide.
```

```
<220> FEATURE:
<221> NAME/KEY: misc_feature
<222> LOCATION: (16)..(17)
<223> OTHER INFORMATION: These two nucleotides are connected by a
      phosphorothioate linkage.
<220> FEATURE:
<221> NAME/KEY: misc_feature
<222> LOCATION: (17)..(17)
<223> OTHER INFORMATION: This nucleotide is a 2'-O-methyl modified
      nucleotide.
<220> FEATURE:
<221> NAME/KEY: misc_feature
<222> LOCATION: (17)..(18)
<223> OTHER INFORMATION: These two nucleotides are connected by a
      phosphorothioate linkage.
<220> FEATURE:
<221> NAME/KEY: misc_feature
<222> LOCATION: (18)..(18)
<223> OTHER INFORMATION: This nucleotide is a 2'-O-methyl modified
      nucleotide.
<220> FEATURE:
<221> NAME/KEY: misc_feature
<222> LOCATION: (18)..(19)
<223> OTHER INFORMATION: These two nucleotides are connected by a
      phosphorothioate linkage.
<220> FEATURE:
<221> NAME/KEY: misc_feature
<222> LOCATION: (19)..(19)
<223> OTHER INFORMATION: This nucleotide is a 2'-O-methyl modified
      nucleotide.
<220> FEATURE:
<221> NAME/KEY: misc_feature
<222> LOCATION: (19)..(20)
<223> OTHER INFORMATION: These two nucleotides are connected by a
      phosphorothioate linkage.
<220> FEATURE:
<221> NAME/KEY: misc_feature
<222> LOCATION: (20)..(20)
<223> OTHER INFORMATION: This nucleotide is a 2'-O-methyl modified
      nucleotide.
<220> FEATURE:
<221> NAME/KEY: misc_feature
<222> LOCATION: (20)..(21)
<223> OTHER INFORMATION: These two nucleotides are connected by a
      phosphorothioate linkage.
<220> FEATURE:
<221> NAME/KEY: misc_feature
<222> LOCATION: (21)..(21)
<223> OTHER INFORMATION: This nucleotide is a 2'-O-methyl modified
      nucleotide.
<220> FEATURE:
<221> NAME/KEY: misc_feature
<222> LOCATION: (21)..(22)
<223> OTHER INFORMATION: These two nucleotides are connected by a
      phosphorothioate linkage.
<220> FEATURE:
<221> NAME/KEY: misc_feature
<222> LOCATION: (22)..(22)
<223> OTHER INFORMATION: This nucleotide is a 2'-fluoro modified
      nucleotide.

<400> SEQUENCE: 17
nnnnnnnnnn nnnnnnnnnn nn                                          22

<210> SEQ ID NO 18
<211> LENGTH: 20
<212> TYPE: RNA
<213> ORGANISM: Artificial Sequence
<220> FEATURE:
<223> OTHER INFORMATION: Synthetic nucleic acid sequence

<400> SEQUENCE: 18
uuaaucucuu uacugauaua                                             20

<210> SEQ ID NO 19
```

```
<211> LENGTH: 19
<212> TYPE: RNA
<213> ORGANISM: Artificial Sequence
<220> FEATURE:
<223> OTHER INFORMATION: Synthetic nucleic acid sequence

<400> SEQUENCE: 19
uauaucagua aagagauua                                                    19
```